US007052837B2

(12) United States Patent
Johnson et al.

(10) Patent No.: US 7,052,837 B2
(45) Date of Patent: May 30, 2006

(54) HISTOPLASMA CAPSULATUM CATALASE SEQUENCES AND THEIR USE IN THE DETECTION OF HISTOPLAMSA CAPSULATUM AND HISTOPLASMOSIS

(75) Inventors: Clayton H. Johnson, Little Rock, AR (US); J. Lyndal York, Little Rock, AR (US); Joan E. McEwen, Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 360 days.

(21) Appl. No.: 10/099,352

(22) Filed: Mar. 13, 2002

(65) Prior Publication Data

US 2003/0082569 A1    May 1, 2003

Related U.S. Application Data

(60) Provisional application No. 60/275,353, filed on Mar. 13, 2001.

(51) Int. Cl.
C12Q 1/68 (2006.01)
C12P 19/34 (2006.01)
C07H 21/04 (2006.01)

(52) U.S. Cl. .......... 435/6; 435/91.1; 435/91.2; 536/23.1; 536/23.7; 536/24.1; 536/24.3; 536/24.32

(58) Field of Classification Search ........ 536/23.1, 536/24.32
See application file for complete search history.

(56) References Cited

U.S. PATENT DOCUMENTS 4,946,777 A    8/1990   Laméris et al.

| | | |
|---|---|---|
| 5,242,800 A | 9/1993 | Jimenez et al. |
| 5,324,632 A | 6/1994 | Weisberg et al. |
| 5,352,579 A | 10/1994 | Milliman |
| 5,360,732 A | 11/1994 | Berka et al. |
| 5,360,901 A | 11/1994 | Berka et al. |
| 5,580,971 A | 12/1996 | Mitsuhashi |
| 5,693,501 A | 12/1997 | Lee et al. |
| 5,707,802 A | 1/1998 | Sandhu et al. |
| 5,734,035 A * | 3/1998 | Sharp et al. ............ 536/23.1 |
| 5,763,169 A | 6/1998 | Sandhu et al. |
| 5,859,224 A * | 1/1999 | Maoka et al. ............ 536/23.72 |

(Continued)

FOREIGN PATENT DOCUMENTS

EP    0272009    6/1988

(Continued)

OTHER PUBLICATIONS

GenBank Accession AL449104.*

(Continued)

Primary Examiner—Jehanne Sitton
Assistant Examiner—Sarae Bausch
(74) Attorney, Agent, or Firm—Kilpatrick Stockton LLP; Cynthia B. Rothschild; Charles W. Calkins

(57) ABSTRACT

The present invention describes Histoplasmosis capsulatum catalase A and catalase P nucleic acid and protein sequences as reagents for the detection of H. capsulatum infection. Specifically, the invention describes intron sequences from the H. capsulatum catalase A (CATA) and catalase P (CATP) genes which can be used for hybridization and PCR based detection of H. capsulatum infection. In another embodiment, assays for H. capsulatum catalase P or catalase A polypeptides are used as diagnostic tests for H. capsulatum infection and histoplasmosis, respectively. Also described is the differentiation of H. capsulatum from Blastomyces dermititidis based on a H. capsulatum catalase P PCR based assay.

29 Claims, 20 Drawing Sheets

U.S. PATENT DOCUMENTS

| | | | |
|---|---|---|---|
| 5,869,241 A * | 2/1999 | Edwards et al. | 435/6 |
| 5,914,265 A * | 6/1999 | Roop et al. | 435/320.1 |
| 5,919,617 A | 7/1999 | Bhattacharjee et al. | |
| 5,922,563 A * | 7/1999 | Alderete | 435/69.1 |
| 5,994,066 A | 11/1999 | Bergeron et al. | |
| 5,997,912 A | 12/1999 | Schlesinger et al. | |
| 6,001,564 A | 12/1999 | Bergeron et al. | |
| 6,117,641 A | 9/2000 | Berlin et al. | |
| 6,180,339 B1 | 1/2001 | Sandhu et al. | |
| 6,228,575 B1 | 5/2001 | Gingeras et al. | |
| 6,261,768 B1 * | 7/2001 | Todd et al. | 435/6 |

FOREIGN PATENT DOCUMENTS

| | | |
|---|---|---|
| EP | 804619 A1 | 11/1997 |
| WO | WO 96/21741 | 7/1996 |
| WO | WO 98/46738 | 10/1998 |
| WO | WO 99/54508 | 10/1999 |
| WO | WO 99/55874 | 11/1999 |

OTHER PUBLICATIONS

Sequence alignments.*

GenBank Accession AC036149, M88342.*

Williams et al. "mucK, a gene in *Acinetobacter calcoaceticus* ADP1 Encodes the Ability to Grow an Exogenous Cis, Cis-muconate as the sole carbon source", J. Bacteriol. 1997 179(18) 5935-42.*

Sasaki et al. "The genome sequence and structure of rice chromosome 1", Nature (2002) vol. 420 (6913) pp. 312-316.*

Ampel, Emerging Disease Issues and Fungal Pathogens Associated with HIV Infection, *Emerg. Infect. Dis.*, 2:109-116, 1996.

Beaman, B. L. et al., Purification and Properties of a Unique Superoxide Dismutase from *Nocardia asteroides*, *J. Biol. Chem.*, 258:91-96, 1983.

Bird, Single-Chain Antigen-Binding Proteins, *Science*, 242:423-426, 1988.

Broaddus et al., Bronchoalveolar Lavage and Transbronchial Biopsy for the Diagnosis of Pulmonary Infections in the Acquired Immunodeficiency Syndrom, *Ann. Intern. Med.*, 102(6):747-752, Jun. 1985.

Brummer et al., Antifungal Mechanisms of Activated Murine Bronchoalveolar or Peritoneal Macrophages for *Histoplasma capsulatum*, *Clin. Exp. Immunol.*, 102(1):65-70, Oct. 1995.

Bullock, W. E. et al., Role of the Adherence-Promoting Receptors, CR3, LFA-1, and p150,95, in Binding of *Histoplasma capsulatum* by Human Macrophages, *Journal of Experimental Medicine*, 165:195-210, 1987.

Castro et al., 1993 Revised Classification System for HIV Infection and Expanded Surveillance Case Definition for AIDS among Adolescents and Adults, *MMRW* 41:1-14, 1992.

Chomczynski, P. et al., Single-Step Method of RNA Isolation by Acid Guanidinium Thiocyanate-Phenol-Chloroform Extraction, *Anal. Biochem.*, 162:156-159, 1987.

Church, G.M. et al., Genomic Sequencing, *Proc. Natl. Acad. Sci., USA*, 81:1991-1995, 1984.

Cockerill, F.R. et al., Rapid-Cycle Real-Time PCR: a Revolution for Clinical Microbiology, *ASM News*, 68:77-83, 2002.

Cohen et al., Sequence of the *Saccharomyces cerevisiae* CTA1 Gene and Amino Acid Sequence of Catalase A Derived from It, *Eur. J. Biochem.*, 176(1):159-163, Sep. 1988.

Cohen et al., Isolation of the Catalase A Gene of *Saccharomyces cerevisiae* by Complementation of the ctal Mutation, *Mol. Gen. Genet.*, 200(1):74-79, 1985.

Crowele, A. J. et al., Evidence that Vesicles Containing Living, Virulent *Mycobacterium tuberculois* or *Mycobacterium avium* in Cultured Human Macrophages Are Not Acidic, *Infect. Immun.*, 59:1823-1831, 1991.

Davies et al., Disseminated Histoplasmosis in Immunologically Suppressed Patients, *Am. J. Med.*, 64:94-100, 1978.

DeGroote, M. A. et al., Periplasmic Superoxide Dismutase Protects *Salmonella* from Products of Phagoctye NADPH-Oxidase and Nitric Oxide Synthase, *Proc. Natl. Acad. Sci. (USA)*, 94:13997-14001, 1997.

Deepe, G. S., The Immune Response to *Histoplasma Capsulatum*: Unearthing Its Secrets, *J. Lab. Clin. Med.*, 123:201-205, 1998.

Deretic, V. et al., *Mycobacterium tuberculosis* Phagosome, *Mol. Microbiol.*, 31:1603-1609, 1999.

Desai et al., Killing of *Histoplasma Capsulatum* by Macrophage Colony Stimulating Factor-Treated Human Monocyte-Derived Macrophages: Role for Reactive Oxygen Intermediates, *J. Med. Microbiol.*, 43(3):224-229, Sep. 1995.

Eissenberg, L. G. et al., The Interplay between Histoplasma Capsulatum and Its Host Cells, vol. I, Ch. 6, W. B. Saunders Company, Ltd. London, UK, 1994.

Eissenberg, L. G. et al., *Histoplasma Capsulatum* Modulates the Acidification of Phagolysosomes, *J. Exp. Med.*, 177:1605-1611, 1993.

Evard et al., The Cyanelle Genome of *Cyanophora Paradoxa*, Unlike the Chloroplast Genome, Codes for the Ribosomal L3 Protein, *Nucleic Acid Res.*, 18:1115-1119, 1990.

Fang, F. C. et al., Virulent *Salmonella Typhimurium* Has Two Periplasmic Cu, Zn-Superoxide Dismutases, *Proc. Natl. Acad. Sci. (USA)*, 96:7502-7507, 1999.

Frugoli, J. A. et al., Catalase Is Encoded by a Multigene Family in *Arabidopsis thaliana* (L.) Heynh, *Plant Physiol.*, 112:327-336, 1996.

Frugoli, J. A. et al., Intron Loss and Gain during Evolution of the Catalase Gene Family in Angiosperms, *Genetics*, 149:355-365, 1998.

Garcia, E. et al., Molecular Characterization of KatY (Antigen 5), a Thermoregulated Chromosomally Encoded Catalase-Peroxidase of *Yersinia Pestis*, *J. Bacteriol.*, 181:3114-3122, 1999.

George et al., Radioimmunoassay: A Sensitive Screening Test for Histoplasmosis and Blastomycosis, *Am. Rev. Respir. Dis.*, 124(4):407-10, Oct. 1981.

Goffeau, A. et al., Life with 6000 Genes, *Science*, 274:563-567.

Goodwin, R. A. et al., Histoplasmosis in Normal Hosts, *Medicine* (Baltimore), 60:231-266, 1981.

Goodwin, R. A., Jr. et al, Disseminated Histoplasmosis: Clinical and Pathalogic Correlations, *Medicine*, 59:1-33, 1980.

Guan, L. et al., Molecular Evolution of Maize Catalases and Their Relationship to Other Eukaryotic and Prokaryotic Catalases, *J. Mol. Evol.*, 42:570-579, 1996.

Hamilton, A.J. et al., Evidence That the M Antigen of *Histoplasma Capsulatum* var. *Capsulatum* Is a Catalase Which Exhibits Cross-Reactivity with Other Dimorphic Fungi, *J. Med. Vet. Mycol.,* 28:479-485, 1990.

Hansen et al., Functional Complementation of Catalase-Defective Peroxisomes in a Methoylotrophic Yeast by Import of the Catalase A from *Saccharomyces cerevisiae*, *Eur. J. Biochem.*, 184(1):173-179, Sep. 1989.

Hartman, P. et al., Immunological Defense Mechanisms in Tuberculosis and MAC-Infection, *Diag. Microbiol. Infect. Dis.*, 34:147-152, 1999.

Hochman et al., Purification and Characterization of a Catalase-Peroxidase and a Typical Catalase from the Bacterium *Klebsiella pneumoniae*, *Biochim. Biophys. Act*, 1077(3):299-307, Apr. 1991.

Howard, Studies on the Catalase of *Histoplasma Capsulatum*, *Infect. Immun.*, 39(3):1161-1166, Mar. 1983.

Howard, Comparative Sensitivity of *Histoplasma Capsulatum* Conidiospores and Blastospores to Oxidative Antifungal Systems, *Infect. Immun.,* 32(1):381-387, Apr. 1981.
Izawa et al., Importance of Catalase in the Adaptive Response to Hydrogen Peroxide: Analysis of Acatalasaemic *Saccharomyces cerevisiae, Biochem. J,* 320(Pt. 1):61-67, Nov. 15, 1996.
Jacoboson et al., Reevaluation of Diagnostic Histoplasma Serologies, *Am. J. Med. Sci.,* 281(3): 143-51, Jun. 1981.
Jeavons, L. et al. Identification and Purification of Specific *Penicillium marneffei* Antigens and Their Recognition by Human Immune Sera, *J. Clin. Microbiol.,* 36:949-954, 1998.
Johnson, C. H. et al., Redunancy, Phylogeny and Differential Expression of *Histoplasma Capsulatum* Catalases, *Microbiology,* 148:1129-1142, 2002.
Johnson, C. et al., Catalase Isozymes and Genes of *Histoplasma Capsulatum,* Abstract I-73, Abstracts of the *Amer. Soc. for Microbiol.,* 100:397, 2000.
Johnson, C. H. et al., Isolation of a *Histoplasma Capsulatum* cDNA that Complements a Mitochondrial NAD(+)-Isocitrate Dehydrogenase Subunit I-Deficient Mutant of *Saccharomyces cereviasiae, Yeast,* 15:799-804, 1999.
Johnson, et al., Characterization of the Differentially Expressed Catalase Isozymes and Genes of Histoplasma Capsulatum, *Abstracts of the General Meeting of the Amer. Soc. Microbiol.,* 99:298-299, 1999.
Johnson, C.H. et al., The *psbB* Gene Cluster of the *Chlamydomonas Reinhardtii* Chloroplast: Sequence and Transcriptional Analysis of *psbN* and *psbH,* Plant *Mol. Biol.,* 22:645-658, 1993.
Johnson, S. M. et al., Preparation and ELISA Evaluation of *Blastomyces Dermatitidis* Yeast Phase Lysate Antigens, *Diagn. Microbiol. Infect. Dis.,* 11(2):81-86, Oct. 1998.
Kamei et al., Induction of Stress Protein Synthesis in *Histoplasma Capsulatum* by Heat, Low pH and Hydrogen Peroxide, *J. Med. Vet. Mycol.,* 30(5):385-393, 1992.
Kasuga, T. et al., Phylogenetic Relationships of Varieties and Geographical Groups of the Human Pathogenic Fungus *Histoplasma Capsulatum* Darling, *J. Clin. Micro.,* 37:653-663, 1999.
Kawasaki et al., Two Divergent Catalase Genes Are Differentially Regulated during *Aspergillus Nidulans* Development and Oxidative Stress, *J. Bacteriol.,* 179(10):3284-3292, May 1997.
Keath et al., Typing of *Histoplasma Capsulatum* by Restriction Fragment Length Polymorphisms in a Nuclear Gene, *J. Clin. Microbiol.,* 30(8):2104-2107, Aug. 1992.
Kersulyte et al., Diversity among Clinical Isolates of *Histoplasma Capsulatum* Detected by Polymerase Chain Reaction with Arbitrary Primers, *J. Bacteriol.,* 174(22):7075-7079, Nov. 1992.
Klein, et al., Isolation, Purification, and Radiolabeling of a Novel 120-κD Surface Protein on *Blastomyces Dermatitidis* Yeasts to Detect Antibody in Infected Patients, *J. Clin. Invest.,* 85(1):152-161, Jan. 1990.
Klotz, M. G., Catalase Genes Are of Bacterial Origin and Have Evolved in Eukaryotes by Intron Acquisition, *American Society for Microbiology,* 101st Annual Meeting, Abstract H-18, 2000.
Johnson, C. et al., The Catalase Isozymes and Genes of *Histoplasma Capsulatum, Abstract #361, XXI Fungal Genetics Conference, at* http://www.fgsc.net/fungalgenetics2001/generega, htm, Asitomar, CA, Mar. 2001.
Klotz, M. G., On the Molecular Evolution of Catalatic Hydroperoxidases, University of Louisville, KY and University of Manitoba, Winnipeg, MB, Canada.
Klotz, M. G. et al., Phylogenetic Relationships among Prokaryotic and Eukaryotic Catalases, *Mol. Biol. Evol.,* 14:951-958, 1997.
Kragler et al., Two Independent Peroxisomal Targeting Signals in Catalase A of *Saccharomyces cerevisiae, J. Cell. Biol.,* 120(3):665-673, Feb. 1993.
Kurita, N. et al., Resistance of *Histoplasma Capsulatum* to Killing by Human Neutrophils, *Mycopathologia,* 115:207-213, 1991.
Lardinois et al., Characterization of Hydrogen Perioxide and Superoxide Degrading Pathways of Aspergillus Niger Catalase: A Steady-State Analysis, *Free Radic. Res.,* 20(1):29-50, Jan. 1994.
Leutenegger, C.M. et al., Real-Time TaqMan PCR as a Specific and More Sensitive Alternative to the Branched-chain DNA Assay for Quantitation of Simian Immunodeficiency Virus RNA, *AIDS Res. Hum. Retroviruses,* 17:243-251, 2001.
Li, R-K et al., In Vitro Activities of Voriconazole, Intraconazole, and Amphotericin B against *Blastomyces Dermatitidis, Coccidioides Immitis,* and *Histoplasma Capsulatum, Antimicrobial Agents and Chemotherapy,* 44:1734-1736, 2000.
Li, et al., Expression of *kat*G in *Mycobacterium tuberculosis* Is Associated with Its Growth and Persistence in Mice and Guinea Pigs, *J. Infect. Dis.,* 177:1030-1035, 1998.
Loewen, P.C. et al., Catalase—and "Old" Enzyme That Continues to Surprise Us, *ASM News,* 66:76-82, 2002.
Lopez-Medrano, R., An Immunodominant 90-Kilodalton *Aspergillus fumigatus* Antigen Is the Subunit of a Catalase, *Infection & Immunity,* 63:4774-4780, 1995.
Ma et al., Bacterioferritin A Modulates Catalase A (KatA) Activity and Resistance to Hydrogen Peroxide in *Pseudomonas aeruginosa, J. Bacteriol.,* 181(12):3730-3742, Jun. 1999.
Mangala, A.N. et al., Determination of bacterial load by real-time PCR using a broad-range (universal) probe and primers set, *Microbiology* 148, 257-266, 2002.
Marchler, G. et al., A *Saccharomyces cereviisiae* Element Controlled by Protein Kinase A Activates Transcription in Response to a Variety of Stress Conditions, UAS *EMBO Journal,* 12:1997-2003, 1993.
Maresca et al., Morphological Transitiion in the Human Fungal Pathogen *Histoplasma Capsulatum, Trends Microbiol.,* 2:110-114, 1994.
Maresca, B. et al., Respiration in the Yeast and Mycelial Phases of *Histoplasma Capsulatum, Journal of Bacteriology,* 138:647-649, 1979.
Miyashiro et al., Immunofluorescent Detection of *Histoplasma Capsulatum* in Primate Experimental Ocular Histoplasmosis, *Curr. Eye. Res.,* 5(11):833-840, Nov. 1986.
Murray, et al., Nucleotide Sequence of Peroxisomal Catalase from the Yeast *Candida tropicalis* pK223; Identification of an Upstream BamHI Site Polymorphism, *Nucleic Acids Res.*, 17(9):3600, May 1989.

Murray, et al., The Nucleotide Sequence of Complementary DNA and the Deduced Amino Acid Sequence of Peroxisomal Catalase of the Yeast *Candida tropicalis* pK223, *Gene*, 61(3):401-413, 1987.

Nadkarni, M.A. et al., Determination of Bacterial Load by Real-Time PCR Using a Broad-Range (Universal) Probe and Primers Set, *Microbiology*, 148:257-266, 2002.

Navarro et al., Posttranscriptional Control Mediates Cell Type-Specific Localization of Catalase A during *Aspergillus nidulans* Development, *J. Bacteriol.*, 180(21):5733-5738, Nov. 1998.

Newman, S. L. et al., Phagocytosis of *Histoplasma Capsulatum* Yeasts and Microconidia by Human Cultured Macrophages and Alveolar Macrophages, *Journal of Clinical Investigation*, 85:223-230, 1990.

Newman, S. L. et al, Digestion of *Histoplasma Capsulatum* Yeasts by Human Macrophages, *J. Immunol.*, 149:574-580, 1992.

Newman, S. L. et al., Human Neutrophil-Mediated Fungistasis against *Histoplasma Capsulatum*, *J. Clinical Investigation*, 92:624-631, 1993.

Newman, S. L., Macrophages in Host Defense against *Histoplasma Capsulatum*, *Trends Microbiol.*, 7:67-71, 1999.

Okada et al., Catalase Gene of Yeast *Candida tropicalis*: Sequence Analysis and Comparison with Peroxisomal and Cytosolic Catalases from Other Sources, *Eur. J. Biochem.*, 170(1-2):105-10, Dec. 1987.

Padhye et al., Comparative Evaluation of a Chemiluminescent DNA Probe and an Exoantigen Test for Rapid Identification of *Histoplasma Capsulatum*, *J. Clin. Microbiol.*, 30(12):3108-3111, Dec. 1992.

Patriarca, E. J. et al., Mitochondrial Activity and Heat-Shock Response during Morphogenesis in the Pathogenic Fungus *Histoplasma Capsulatum*, *Biochemistry & Cell Biology*, 70:207-214, 1992.

Pitkin, J. W., et al., A Putative Cyclic Peptide Efflus Pump Encoded by the *TOXA* Gene of the Plant-Pathogenic Fungus *Cochliobolus carbonum*, *Microbiology*, 142:1557-1565, 1996.

Radcliff et al., Catalase, a Novel Antigen for *Helicobacter pylori* Vaccination, *Infect. Immun.*, 65(11):4668-4674, Nov. 1997.

Rambukkana, A. et al., Identification of a Novel 17-κDA Protein from *Mycobacterium Tuberculosis* Culture Fluid by a Monoclonal Antibody Specific for the *Mycobaterium Tuberculosis* Complex, *Scand. J. Immunol.*, 37:471-478, 1993.

Raynaud, C. et al., Extracellular Enzyme Activities Potentially Involved in the Pathogenicity of *Mycobacterium Tuberculosis*, *Microbiology*, 144;577-587, 1998.

Reid et al., Direct Detection of *Histoplasma Capsulatum* in Soil Suspensions by Two-Stage PCR, *Mol. Cell. Probes*, 13(4):269-273, Aug. 1999.

Reiss, et al., Non-Culture Based Diagnostic Tests for Mycotic Infections, *Med. Mycol.*, 38(1):147-159, 2000.

Rouse, D. A. et al., Molecular Mechanisms of Isoniazid Resistance in *Mycobacterium Tuberculosis* and *Mycobacterium Bovis*, *Infect. Immun.*, 63:1427-1433, 1995.

Schaffner, A. et al., In Vitro Susceptibility of Fungi to Killing by Neutrophil Granulocytes Discriminates between Primary Pathogenicity and Opportunism, *J. Clin. Invest.*, 78:511-524, 1986.

Schaffner, A. et al., Killing of *Aspergillus* Spores Depends on the Anatomical Source of the Macrophage, *Infect. Immun.*, 42:1109-1115, 1983.

Schaffner, A. et al., Selective Protection against Conidia by Mononuclear and against Mycelia by Polymorphonuclear Phagocytes in Resistance to *Aspergillus*, *J. Clin. Invest.*, 69:617-631, 1982.

Scherr, G. H. et al., Studies on the Dimorphism of *Histoplasma Capsulatum*, *Exp. Cell Res.*, 12:92-107, 1957.

Scherr & Weaver, The Dimorphism Phenomenon in Yeasts, *Bact. Rev.*, 17:51-92, 1953.

Schnur, R. A. et al., The Respiratory Burst Response to *Histoplasma Capsulatum* by Human Neutrophils, *Journal of Immunology*, 144:4765-4772, 1990.

Sherman, D. R. et al., Compensatory *ahpC* Gene Expression in Isoniazid-Resistant *Mycobacterium Tuberculosis*, *Science*, 272:1641-1643, 1996.

Sonnenberg, M. G. et al., Definition of *Mycobacterium Tuberculosis* Culture Filtrate Proteins by Two-Dimensional Polyacrylamide Gel Electrophoresis, N-Terminal Amino Acid Sequencing, and Electrospray Mass Spectrometry, *Infect. Immun.*, 65:4515-4524, 1997.

Spiegelhalder, C. B. et al., Purification of *Helicobacter pylori* Superoxide Dismutase and Cloning and Sequencing of the Gene, *Infec. Immun.*, 61:5315-5325, 1993.

Spitzer et al., Use of Mitochondrial and Ribosomal DNA Polymorphisms to Classify Clinical and Soil Isolates of *Histoplasma Capsulatum*, *Infect. Immun.*, 57:1409-1412, May 1989.

Stein, D.K. et al., Fungal Infections in the Immunocompromised Host, *Diagn. Microbiol., Infect., Dis.*, 12:221S-228S, 1989.

Storz, G. et al., OxyR: A Regulator of Antioxidant Genes, *J. Nutr.*, 122:627-30, 1992.

Storz, G. et al., The OxyR Regulon, *Antonie Van Leeuwenhoek*, 58:157-161, 1990.

Storz, G. et al., Transcriptional Regulator of Oxidative Stress-Inducible Genes: Direct Activation by Oxidation, *Science*, 248:189-194, 1990.

Storz, G. et al., Bacterial Defenses against Oxidative Stress, *Trends Genet.*, 6:363-368, 1990.

Strasser, J. E. et al., Regulation of the Macrophage Vacuolar ATPase and Phagosome-Lysosome Fusion by *Histoplasma Capsulatum*, *J. Immunol.*, 162:6148-6154, 1999.

Sturgill-Koszycki, S., et al., Lack of Acidification in *Mycobacterium* Phagosomes Produced by Exclusion of the Vesicular Proton-ATPase, *Science*, 263:678-681, 1994.

Thompson, J.D. et al., Clustal W: Improving the Sensitivity of Progressive Multiple Sequence Alignment through Sequence Weighting Position-Specific Gap Penalties and Weight Matrix Choice, *Nucleic Acids Res.*, 22:4673-4680, 1994.

Vera-Cabrera, L. et al., Distribution of *Nocardia Brasiliensis* Catalase Gene Fragment in Members of the Genera *Nocardia*, *Gordona*, and *Rhodococcus*, *J. Clin. Microbiol.*, 37:1971-1976, 1999.

Wall, S.J. et al., Quantitative Reverse Transcription—Polymerase Chain Reaction (RT-PCR): A Comparison of Primer-Dropping, Competitive, and Real-time RT-PCRs, *Anal. Biochem.*, 300:269-273, 2002.

Wheat et al., Risk Factors for Disseminated or Fatal Histoplasmosis, *Ann. Intern. Med.*, 96:159-163, 1982.

Wheat et al., Histoplasmosis in the Acquired Immune Deficiency Syndrome, *Am. J. Med.*, 78:203-210, 1985.

Wilson, T. M. et al., Effect of *inhA* and *katG* on Isoniazid Resistance and Virulence of *Mycobacterium Bovis*, *Mol. Microbiol.*, 15:1009-1015, 1995.

Woods et al., Fast DNA Isolation from *Histoplasma Capsulatum*: Methodology for Arbitrary Primer Polymerase Chain Reaction-Based Epidemiological and Clinical Studies, *J. Clin. Microbiol.*, 31(2):463-464, Feb.1993.

Woods, J.P. et al., InVivo Generation of Linear Plasmids with Addition of Telomeric Sequences by *Histoplasma* Capsulatum, *Molecular Microbiology*, 6:3603-3610, 1992.

Worsham, P.L. et al., Quantitative Plating of *Histoplasma Capsulatum* without Addition of Conditioned Medium or Siderophores, *J. Med. & Veterinary Mycology*, 26:137-143, 1998.

Zamocky et al., Site-Directed Mutagenesis of the Lower Parts of the Major Substrate Channel of Yeast Catalase A Leads to Highly Increased peroxidatic Activity, *FEBS Lett.*, 367(3):241-245, Jul. 1995.

Zancope-Oliveria et al., Molecular Cloning, Characterization, and Experession of the M Antigen of *Histoplasma Capsulatum*, *Infect. Immun.*, 67(4):1947-1953, Apr. 1999.

Johnson, C. et al., Investigation of the Catalase Enzyme of *Histoplasma Capsulatum*, *Fed. Res. Prog.*, Abstract 0001:598, Jan. 1997.

Johnson et al., Differentially Expressed Catalase Genes in *Histoplasma Capsulatum*, Abstract F-65, *Abstracts of the General Meeting of the Amer. Soc. Microbiol.*, 98:263-64, 1998.

NCBI Sequence, Accession No. AF189368, "Ajellomyces Capsulatus Catalase Isozyme A (CATA) mRNA, Complete Cds.," Microbiology, 148 (pt. 4):1129-1142, 2002, available at http://www.ncbi.nlm.nih.gov/entrez.

NCBI Sequence, Accession No. AF189369, "Ajellomyces Capsulatus Catalase Isozyme P (CATP) mRNA, Complete Cds.," Microbiology, 148 (pt. 4):1129-1142, 2002, available at http://www.ncbi.nlm.nih.gov.

NCBI Sequence, Accession No. AF026268, "Ajellomyces Capsulatus M Antigen Gene, Complete Cds.," Infect. Immun., 67 (4):1947-1953, 1999, available at http://www.ncbi.nlm.nih.gov/entez.

NCBI Sequence, Accession No. AF139985, "Ajellomyces Capsulatus B (CATB) mRNA, Complete Cds.," Microbiology, 148 (4):1129-1142, 2002, available at http://www.ncbi.nlm.nih.gov.

NCBI Sequence, Accession No. AFU87630, "Aspergillus Fumigatus Catalase Gene, Complete Cds.," Center for Cancer Research, Massachusetts Institute of Technology, Cambridge, MA, Submitted Jan. 29, 1997 (unpublished), available at http://www.ncbi.nlm.nih.gov/entrez.

NCBI Sequence, Accession No. AFU87850, "Aspergillus Fumigatus Catalase (CatB) Gene, Complete Cds.," Center for Cancer Research, Massachusetts Institute of Technology, Cambridge, MA, Submitted Jan. 30, 1997 (unpublished), available at http://www.ncbi.nlm.nih.gov/entrez.

NCBI Sequence, Accession No. Z23138, "Aspergillus Niger CatR Gene, Complete Cds.," Mol. Microbiol., 9 (5):989-998, 1993, available at http://www.ncbi.nlm.nih.gov/entrez.

NCBI Sequence, Accession No. AB006327, "Candida Albicans mRNA for Catalase, Complete Cds.," Nagoya University School of Medicine, Laboratory of Medical Mycology, Japan, Submitted Aug. 6, 1997 (unpublished), available at http://www.ncbi.nlm.nih.gov/entrez.

NCBI Sequence, Accession No. M18832, "C. Tropicalis Peroxisomal Catalase mRNA, Complete Cds.," Gene, 61 (3):401-413, 1987, available at http://www.ncbi.nlm.nih.gov/entrez.

NCBI Sequence, Accession No. AF222055, "Cladosporium Fulvum CAT1 Catalase (cat-1) Gene, Complete Cds.," Eur. J. Biochem.,. 268 (1):15-24, 2001, available at http://www.ncbi.nlm.nih.gov/entrez.

NCBI Sequence, Accession No. AF222056, "Cladosporium Fulvum CAT2 Catalase (cat-2) Gene, Complete Cds.," Eur. J. Biochem., 268 (1):15-24, 2001, available at http://www.ncbi.nlm.nih.gov/entrez.

NCBI Sequence, Accession No. AJ001386, "Claviceps Purpurea Cat1 Gene, Complete Cds.," Institut Fuer Botanik, Westfaelische Wilhelms-Universitaet, Germany, Submitted Jan. 23, 1998 (unpublished), available at http://www.ncbi.nlm.nih.gov/entrez.

NCBI Sequence, Accession No. U37803, "Emericella Nidulans Catalase A (catA) Gene, Complete Cds.," Curr. Genet., 29 (4):352-359, 1996, available at http://www.ncbi.nlm.nih.gov/entrez.

NCBI Sequence, Accession No. U80672, "Emericella Nidulans Catalase (catB) Gene, Complete Cds.," J. Bacteriol., 179 (10):3284-3292, 1997 available at http://www.ncbi.nlm.nih.gov.

NCBI Sequence, Accession No. AF316033, "Aspergillus Nidulans Catalase C (catC) Gene, Complete Cds.," J. Bacteriol., 183 (4):1434-1440, 2001, available at http://www.ncbi.nlm.nih.gov/entrez.

NCBI Sequence, Accession No. X56501, "H. Polymorpha Catalase Gene," FEBS Lett., 303 (2-3):113-116, 1992, available at http://www.ncbi.nlm.nih.gov/entrez.

NCBI Sequence, Accession No. AY027545, "Neurospora Crassa Catalase-1 (cat-1) Gene, Complete Cds.," Free Radic. Biol. Med., 33 (4):521-532, 2002, available at http://www.ncbi.nlm.nih.gov.

NCBI Sequence, Accession No. AY027544, "Neurospora Crassa Catalase-3 (cat-3) Gene, Complete Cds.," Free Radic. Biol. Med., 33 (4):521-532, 2002, available at http://www.ncbi.nlm.nih.gov/entrez.

NCBI Sequence, Accession No. U75451, "Pleurotus Osteatus Catalase Gene (pcat2), Complete Cds.," Microbiology, MIGAL Galilee Technological Center, South Industrial Zone, Kiryat Shmona 12100, Israel, Submitted Oct. 21, 1996, available at http://www.ncbi.nlm.nih.gov/entrez.

NCBI Sequence, Accession No. AJ011298, "Podospora Anserina catA Gene, Exons 1-3," Botanisches Institut, Johann Wolfgang Goethe-Universitaet, Marie-Curie-Str. 9, D-60439, Submitted Sep. 14, 1998 (unpublished).

NCBI Sequence, Accession No. AJ011309, "Podospora Anserina catB Gene, Exons 1-2," Botanisches Institut, Johann Wolfgang Goethe-Universitaet, Marie-Curie-Str. 9, D-60439, Submitted Sep. 14, 1998 (unpublished), available at http://www.ncbi.nlm.nih.gov/entrez.

NCBI Sequence, Accession No. X13028, "Yeast CTA1 Gene for Catalase A," Eur. J. Biochem., 176 (1):159-163, 1988, available at http://www.ncbi.nlm.nih.gov/entrez.

NCBI Sequence, Accession No. X04625, "Yeast CCT1 Gene fro Catalase T (EC 1.11.1.6).," Eur. J. Biochem., 160 (3):487-490, 1988, available at http://www.ncbi.nlm.nih.gov/entrez.

NCBI Sequence, Accession No. D89126, "Schizosaccharomyces Pombe mRNA, Partial cds, Clone: SY0474," DNA Res., 4 (6):363-369, 1997, available at http://www.ncbi.nlm.nih.gov/entrez.

NCBI Sequence, Accession No. L02551 (M74194), "B. Firmus Catalase (katA) Gene, 5'End," Bacillus Firmus DNA (original source text-unpublished), available at http://www.ncbi.nlm.nih.gov/entrez.

NCBI Sequence, Accession No. L02548 (M74194), "B. Firmus ORF A and ORF B, Complete Cds.," Bacillus Firmus DNA (original source text-unpublished), available at http://www.ncbi.nlm.nih.gov/entrez.

NCBI Sequence, Accession No. X85182, "B. Subtilis katE Gene for Catalase," J. Bacteriol., 177 (19):5598-5606, 1995, available at http://www.ncbi.nlm.nih.gov/entrez.

NCBI Sequence, Accession No. AE001825, "Deinococcus Radiodurans R1 Complete Chromosome 2," Science, 286 (5444):1571-1577, 1999.

NCBI Sequence, Accession No. M55161, "E. Coli Catalase HPII (katE) Gene, Complete Cds.," J. Bacteriol., 173 (2):514-520, 1999, available at http://www.ncbi.nlm.nih.gov/entrez.

NCBI Sequence, Accession No. L41246, "Mycobacterium Avium Catalase HPII (katE) Gene, Complete Cds.," Mol. Microbiol., 19 (1):113-123, available at http://www.ncbi.nlm.nih.gov/entrez.

NCBI Sequence, Accession No. U82622, "Pseudomonas Putida Stationary-Phase Inducible Catalase C (catC) Gene, Complete Cds.," Bilogy, Utah State University, UMC5305, Logan, UT, Submitted Dec. 18, 1996, (unpublished), available at http://www.ncbi.nlm.nih.gov/entrez.

NCBI Sequence, Accession No. AF121348, "Sinorhizobium Meliloli Catalase (katC) Gene, Complete Cds.," J. Bacteriol., 181 (8):2634-2639, 1999, available at http://www.ncbi.nlm.nih.gov/entrez.

NCBI Sequence, Accession No. AF000419, "Steptomyces Coelicolor Strain ATCC10147 Catalase (catB) Gene, Complete Cds.," Mol. Microbiol., 35 (1):150-160, 2000, available at http://www.ncbi.nlm.nih.gov/entrez.

NCBI Sequence, Accession No. AF1704449, "Xanthomonas Campestris Pv. Phascoli Monofunctional Catalase KatE (katE) Gene, Complete Cds.," Gene, 241 (2):259-265, 2000, available at http://www.ncbi.nlm.nih.gov/entrez.

NCBI Sequence, Accession No. AF021937, "Arabidopsis Thaliana Catalase 3 (CAT3) and Catalase 1 (CAT1) Genes, Complete Cds.," Genetics, 149 (1):355-365, 1998, available at http://www.ncbi.nlm.nih.gov/entrez.

NCBI Sequence, Accession No. AL022023, "Arabidopsis Thaliana DNA Choromosome 4, BAC Clone M4E13 (ESSAII Project)," MIPS, at the Max-Planck-Institut feur Biochemie, Am Klopferspitz 18a, D-82152 Martinsried, FRG, Project Coordinator: Mike Bevan, Molecular Genetics Department, Cambridge Laboratory, John Innes Centre, Colney Lane, NR4 7UJ Norwich, UK, Submitted Apr. 4, 1998 (unpublished), available at http://www.ncbi.nlm.nih.gov/entrez.

NCBI Sequence, Accession No. AF021937, "Arabidopsis Thaliana Catalase 3 (CAT3) and Catalase 1 (CAT1) Genes, Complete Cds.," Genetics, 149 (1):355-365, 1998, available at http://www.ncbi.nlm.nih.gov/entrez.

NCBI Sequence, Accession No. AF035252, "Glycine Max Catalase (cat1) mRNA, Complete Cds.," Plant Pathology, Iowa State University, 351 Bessey, Ames, IA, Submitted Nov. 20, 1997.

NCBI Sequence, Accession No. AF035253, "Glycine Max Catalase (cat2) mRNA, Complete Cds.," Plant Pathology, Iowa State University, 351 Bessey, Ames, IA, Submitted Nov. 20, 1997, available at http://www.ncbi.nlm.nih.gov/entrez.

NCBI Sequence, Accession No. X61626, "O. Sativa mRNA for Catalase," Plant Mol. Biol., 18 (5):973-976, 1992, available at http://www.ncbi.nlm.nih.gov/entrez.

NCBI Sequence, Accession No. D26484, "Oryza Sativa (Japonica Cultivar-Group) mRNA for Catalase, Complete Cds.," Plant Physiol., 105 (3):1015-1016, 1994, available at http://www.ncbi.nlm.nih.gov/entrez.

NCBI Sequence, Accession No. D21162, "Ricinus Communis Gene for Catalase CAT2, Complete Cds.," Plant Mol. Biol., 25 (3):507-516, 1994, available at http://www.ncbi.nlm.nih.gov/entrez.

NCBI Sequence, Accession No. U27082, "Solanum Tuberosum Catalase (CAT1) mRNA, Complete Cds.," Plant Physiol., 108 (4):1748, 1995, available at http://www.ncbi.nlm.nih.gov/entrez.

NCBI Sequence, Accession No. X12538, "Maize cat-1 mRNA for Catalase-1 Isoenzyme (EC 1.11.1.6)," Scandalios J. G., North Carolina State University, Dept. of Genetics, Box 7614, Raleigh, NC, Submitted Aug. 2, 1988, available at http://www.ncbi.nlm.nih.gov/entrez.

NCBI Sequence, Accession No. X54819, "Maize mRNA for Catalase 2.," Plant Physiol., 96:1379-1381, 1991, available at http://www.ncbi.nlm.nih.gov/entrez.

NCBI Sequence, Accession No. L05934, "Zea Mays Catalase (CAT3) Gene, Complete Cds.," Plant Mol. Biol., 22 (6):1031-1038, 1993, available at http://www.ncbi.nlm.nih.gov/entrez.

NCBI Sequence, Accession No. AL034488, "Caenorhabditis Elegans YAC Y54G11A, Complete Sequence," Science, 282 (5396):2012-2018, 1998, available at http://www.ncbi.nlm.nih.gov/entrez.

NCBI Sequence, Accession No. U00145, "Drosophila Melanogaster Catalase Gene, Complete Cds.," Arch. Biochem. Biophys., 330 (2):251-258, 1996, available at http://www.ncbi.nlm.nih.gov/entrez.

NCBI Sequence, Accession No. AL035079, "Human DNA Sequence from Clone RPI-53C18 on Chromosome 11p12-13, Complete Sequece," Wellcome Trust Sanger Institute, Hinxton, Cambridgeshire, CB10 ISA, UK, Submitted Mar. 5, 2003, available at http://www.ncbi.nlm.nih.gov/entrez.

NCBI Sequence, Accession No. AH004967, "Rat Catalase Gene, Exon 1," Gene, 79 (2):279-288, 1989, available at http://www.ncbi.nlm.nih.gov/entrez.

* cited by examiner

```
  1 ATTCACAAAAGTTCCAGTTTCAACTTTGAAAAAGAACCAGAGAATATTTTTTTCATCGCC
 61 CCCAATGACTAGCAAGGTTGAAGAAGGGCTCCAGAGGGTCAAGGAGCTGGTGGAAAATAT
      M  T  S  K  V  E  E  G  L  Q  R  V  K  E  L  V  E  N  M
121 GCAGCCAGGAGAGCAAAAGGTCGCAGACCTCGCCCGCGATACTACAGACGTCAACGGATG
 20 Q  P  G  E  Q  K  V  A  D  L  A  R  D  T  T  D  V  N  G  C
181 CCTCCCCTTCACCACTGACCATGGAGTCAAAGTTAGCAATACGGACTTTTGGCTTCGACT
 40 L  P  F  T  T  D  H  G  V  K  V  S  N  T  D  F  W  L  R  L
                                                         I1↓
241 TGCATCCGAAAATCAAACCGGCCCATTGCTTTTGGAGGATCAGATTGCTCGTGAAAAGAT
 60 A  S  E  N  Q  T  G  P  L  L  L  E  D  Q  I  A  R  E  K  I
301 CCATCGATTTGACCATGAAAGAATCCCAGAACGTGTTGTCCATGCACGAGGAACAGGTGC
 80 H  R  F  D  H  E  R  I  P  E  R  V  V  H  A  R  G  T  G  A
361 TTTTGGGCACTTCAAGCTCTTCGAGAGCGCGGCAGACGTGACGTCCGCTGGTGTTCTAAC
100 F  G  H  F  K  L  F  E  S  A  A  D  V  T  S  A  G  V  L  T
421 TGACACGTCCCGAACTACTCCGGTGTTCGTTCGGTTTTCCACCGTCCAGGGCAGCAAAGG
120 D  T  S  R  T  T  P  V  F  V  R  F  S  T  V  Q  G  S  K  G
481 CAGTTTCGATACAGTCCGTGATGTCAGAGGTTTCGCTACCAAATTCTATACGGAAGAAGG
140 S  F  D  T  V  R  D  V  R  G  F  A  T  K  F  Y  T  E  E  G
541 CAACTGGGATCTTGTTGGCAATAACATTCCTGTATTCTTCATTCAAGATGCTGTGAAATT
160 N  W  D  L  V  G  N  N  I  P  V  F  F  I  Q  D  A  V  K  F
         I2↓         ←─────────── GSP2
601 CCCAGATTTTGTTCATGCTGTGAAGCCGGAACCTCATAACGAAGTTCCCCAGGGACAAAC
180 P  D  F  V  H  A  V  K  P  E  P  H  N  E  V  P  Q  G  Q  T
661 AGCACATAACAACTTCTGGGACTTTGTATATATGCATCCTGAGGCGACGCATATGTTCAT
200 A  H  N  N  F  W  D  F  V  Y  M  H  P  E  A  T  H  M  F  M
721 GTGGGCTATGTCGGACAGGGCTATTCCGCGATCATATCGGATGATGCAAGGATTTGGTGT
220 W  A  M  S  D  R  A  I  P  R  S  Y  R  M  M  Q  G  F  G  V
781 TAATACTTTTGTTTTGGTGAATAAACAAGGGAAAAGACATTTCGTTAAGTTTCACTGGAT
240 N  T  F  V  L  V  N  K  Q  G  K  R  H  F  V  K  F  H  W  M
                      ←─────────── GSP1
841 GCCGGAACTTGGGGTTCATTCGCTGGTCCCCGATGAATCATTCAAACTTGGTGGCCAGGA
260 P  E  L  G  V  H  S  L  V  P  D  E  S  F  K  L  G  G  Q  D
901 CCCAGACTTCCACCGTAAAGATCTAATGGAGGcaatcgacaataaggtgtacccgaaatg
280 P  D  F  H  R  K  D  L  M  E  A  I  D  N  K  V  Y  P  K  W
                              1 ─────────→
961 gaagtttggaattcaggttcttcctgaagaaaaagagcacgattttgattttgatatact
300 K  F  G  I  Q  V  L  P  E  E  K  E  H  D  F  D  F  D  I  L
1021 tgatccaactaagatatggccagagagcctaatacctgttcggtatattggagagatgga
320 D  P  T  K  I  W  P  E  S  L  I  P  V  R  Y  I  G  E  M  E
1081 gctcaaccgcaacgtcgatgagttttcccacagacagaacaggttgccttctgtaccgc
340 L  N  R  N  V  D  E  F  F  P  Q  T  E  Q  V  A  F  C  T  A
1141 ccacattgttcctggaattgaattctccggcgatcctctgctccagggacgcaatttctc
360 H  I  V  P  G  I  E  F  S  G  D  P  L  L  Q  G  R  N  F  S
1201 ctattttgacactcaaattacccgccttggcgtcaactgggaggagctcccgatcaatcg
380 Y  F  D  T  Q  I  T  R  L  G  V  N  W  E  E  L  P  I  N  R
1261 tcctgtgtgccctgttatgaatcacaacagggatggtgcaatgcgccataagataaccca
400 P  V  C  P  V  M  N  H  N  R  D  G  A  M  R  H  K  I  T  Q
1321 aggaaccgtaaactattggccgaaccgtttcgaggCTTGCCCACCCACGAAGCCCGAGGA
420 G  T  V  N  Y  W  P  N  R  F  E  A  C  P  P  T  K  P  E  D
                        ←─────────── 3
1381 TGGGGGTTTTGTCACTTACCCTCAAAAGGTAGAGCAGAGTATCAAAGCGAGGATGCTTAG
440 G  G  F  V  T  Y  P  Q  K  V  E  Q  S  I  K  A  R  M  L  S
```

FIG. 1A

```
1441 TAGCAAGTTCCGCGAGCATATCAACCAAGCGCAATTATTCTATAACTCTCTCTCCGAATA
 460   S   K   F   R   E   H   I   N   Q   A   Q   L   F   Y   N   S   L   S   E   Y
1501 CGAAAAGCTCCATGTCAATAATGCTTTTTGCTTTGAGTTGGATCACTGCGATGACCCCAT
 480   E   K   L   H   V   N   N   A   F   C   F   E   L   D   H   C   D   D   P   I
                                        ◄─────────────────── 2
1561 TGTCTACAATAGACTTGTGTCTCGGATTTCTGAAATCGACCATGCCCTCGCCCAAGCCGT
 500   V   Y   N   R   L   V   S   R   I   S   E   I   D   H   A   L   A   Q   A   V
1621 TGCAGTGAAAGTCGGCGCACCGACCCCACCAAGGCCTGGGAGAGACAACCCAGGTCAAAC
 520   A   V   K   V   G   A   P   T   P   P   R   P   G   R   D   N   P   G   Q   T
1681 AACCATTAACCTAAGCCAAAAATACATCAACGACCGTCAGCTGTCCTCTCCCACAATTAA
 540   T   I   N   L   S   Q   K   Y   I   N   D   R   Q   L   S   S   P   T   I   K
1741 AGGTCGGAGGATCGCCATATTGATTGGGGATGGTTACGATTCCGTCGCCTTTGGCACGGT
 560   G   R   R   I   A   I   L   I   G   D   G   Y   D   S   V   A   F   G   T   V
1801 CATAGCCGCGGTGAGCGCCATGGGCGCGCTACCCTTCATAATCGGCACGAAGCGGCAACC
 580   I   A   A   V   S   A   M   G   A   L   P   F   I   I   G   T   K   R   Q   P
1861 CATCTTTGCCGACGACGAAGACAGGAATCACTCCAAGGGTGTGACTCCAAACCACAACTA
 600   I   F   A   D   D   E   D   R   N   H   S   K   G   V   T   P   N   H   N   Y
1921 TACCAGCCAACGCTCCACTTGTTTCGACGCTACTTTCATCCCTGGTGGCTCACATATCAA
 620   T   S   Q   R   S   T   C   F   D   A   T   F   I   P   G   G   S   H   I   K
1981 GGAATTGAGCCAGCTGGGCCTTATCCAGCACTGGGTTGCCGAGCAGTTCGGACACTGCAA
 640   E   L   S   Q   L   G   L   I   Q   H   W   V   A   E   Q   F   G   H   C   K
2041 GGCAATTGGCGCTACAGGAGAGGCCATCAATCTAATCGTGCAGGCTCTGAGCAACCTGCC
 660   A   I   G   A   T   G   E   A   I   N   L   I   V   Q   A   L   S   N   L   P
2101 TGATTTGGAGGTCGCATCCGCCTCGTCAGGGCATCCAGTCGATTGGTACGGCGTTGTCAC
 680   D   L   E   V   A   S   S   G   H   P   V   D   W   Y   G   V   V   T
2161 GTCGAGTAAGCTGCATGAGCCCCATAGTTTGACCGAAGGGATCAAGCTGTTTCCCGAGGC
 700   S   S   K   L   H   E   P   H   S   L   T   E   G   I   K   L   F   P   E   A
2221 GAGTGACTTCTTGGGCAAGCTCTTTTATCAGATCTCCCAGCATCGGAATTATGAGCGGGA
 720   S   D   F   L   G   K   L   F   Y   Q   I   S   Q   H   R   N   Y   E   R   E
2281 GATGGCTGGGTTGACGGACAAGGTTCCATTTTAAATGGCAACATGGCATCGGTGTGAGTC
 740   M   A   G   L   T   D   K   V   P   F   *
2341 GCTAGGAAGCAAGTGAAAGTTAATAGTCAGGCCCCAAAAACAACTATACATACTGTAAAC
2401 ACTAGGTTTAATTTTTGGCTTATATGTTCTTCTGGCAACAATGAATTGGTTTGTTGCTGT
2461 TGCCATTTCTAACAAGTTGTCACAACTAATATATATCCAATCGAATCCATGAAAATGGCA
2521 TTCTTGTTCACATATTC 2537
```

FIG. 1B

GCAGTTTTTTGTTGAGATTAGGGGAGAAAGGCAGGCCAAAGGACAAACTGGGGTTTACCGCCAAATCCCTTTTGAT
CTCNTGCTTTTCTTTTCTCTCTTTTTTTTTTTTTTTTTTTTTTTATTTTANATTCTCGTTTTCTCTCACGGGAGGATTGTT
TATTTACAATGATTGAGAGATTATCCGCATAAACCCCTGATGTTTGGCCATATCTTGAAATTTGGACACTAGATTGGA
ATAGGAATAGTGCAGCCTGAGATTGACATCATTTCACTTCAACACACTTTCGAATCCCAGTTTTTTACCGGTTTCCAG
CTGTTCGACAAAGCAACCCGGCTTCAAGCGGAGGATGGCAATCGAAGAAGCTACTGCTGTCCTGTCAGACAGAAA
CACGCTGCTTCCTAGGTCAGCTTTGGCATTCAACAGTCAGTAGTTCCAGGGCAGCTGGAGTGCTTACCATCTGGCA
TACCATGCAAGACTATATCTCGATGCCGATGGCTGGCCACTGTACGCTATTATATTAGCTGCTTGGAGCAGAGTCTT
TGCGCCTAAGACGGAGCTGGCCAAATAATTGATTCGGATCCGAGCCTGCCTTTGAGGTGGAGAGACACCACATATA
AACAGAACATTTGCGAATGTCAATCTGACCTACCCGGCCACTTTCGGGGCTTTTCATCCGGATTTGACCCCAATACC
TCAAGTGAATTCAGACGACGTCAAATTATTCAAACAGGCAGGTGTTCGCTCATCTAGAGCTTTCCTCTATTTATTGAT
ACTTGTCATGGACGAGCCAAATTAAACTCGAAGGTACACGCCAAGCAAGTCCAAAACTTTTACAGAAAAATCAGTGA
CTTACACCACTGCTTGAATATCGCCACAAGTTAAAACAAGTAGACGAGTCCAGAACACGGGTCGACGTCATTCTGA
GTTAACCTGCCCAGATAGAATATGACGTCTTTTCGTTCGAATGGCGTCTCAAAATCCTCTTGCTCCCTCGGAACATT
GAATGAGGTTGGTTCTCCATATC
▼ mRNA start
ATTCACAAAAGTTCCAGTTTCAACTTTGAAAAAGAACCAGAGAATATTTTTTTCATCGCCCCCAATGAC
TAGCAAGGTTGAAGAAGGGCTCCAGAGGGTCAAGGAGCTGGTGGAAAATATGCAGCCAGGAGAGCAAAAGGTCGC
AGACCTCGCCCGCGATACTACAGACGTCAACGGATGCCTCCCCTTCACCACTGACCATGGAGTCAAAGTTAGCAAT
ACGGACTTTTGGCTTCGACTTGCATCCGAAAATCAAACCGGCCCATTGCTTTTGGAGGATCAGATTGCTCGTGAAAA
GGTTTCATATACCTCTCGTCTAC Aassay5' (#1)
                                      ⟶ Aassay5' (#2)

CTCCCTATTGTGTTCCATGTCTTCCAAGCTT*TGCGGGCAACATATGATAACCATCGAGTTAGAT*CCATCGATTTGAC
CATGAAAGAATCCCAGAACGTGTTGTCCATGCACGAGGAACAGGTGC

Aassay5' (#3)

TTTTGGGCACTTCAAGCTCTTCGAGAGCGCGGCAGACGTGAC*GTCCGCTGGTGTTCTAAC*TGACACGTCCCGAAC
TACTCCGGTGTTCGTTCGGTTTTCCACCGTCCAGGGCAGCAAAGGCAGTTT
    Aassay3' (#3)
  ⟵

*CGATACAGTCCGTGATGT*CAGAGGTTTCGCTACCAAATTCTATACGGAAGAAGGCAACTGGGATCTTGTTGGCAAT
AACATTCCTGTATTCTTCATTCAAGATGCTGTGAAATTCCCAGATTTT
    Aassay3' (#2)                     Aassay3' (#1)
  ⟵                              ⟵

GG*TAAGTATTGATTGATAT*CCCATTTCTTCATTAT*GGATATTTTCGTGTTGATCG*TTTTACAACTCGACATTAGTTCAT

FIG. 2A

GCTGTGAAGCCGGAACCTCATAACGAAGTTCCCCAGGGACAAACAGCACATAACAACTTCTGGGACTTTGTATATAT
GCATCCTGAGGCGACGCATATGTTCATGTGGGCTATGTCGGACAGGGCTATTCCGCGATCATATCGGATGATGCAA
GGATTTGGTGTTAATACTTTTGTTTTGGTGAATAAACAAGGGAAAAGACATTTCGTTAAGTTTCACTGGATGCCGGAA
CTTGGGGTTCATTCGCTGGTCCCCGATGAATCATTCAAACTTGGTGGCCAGGACCCAGACTTCCACCGTAAAGATC
TAATGGAGGCAATCGACAATAAGGTGTACCCGAAATGGAAGTTTGGAATTCAGGTTCTTCCTGAAGAAAAGAGCA
CGATTTTGATTTTGATATACTTGATCCAACTAAGATATGGCCAGAGAGCCTAATACCTGTTCGGTATATTGGAGAGAT
GGAGCTCAACCGCAACGTCGATGAGTTTTTCCCACAGACAGAACAGGTTGCCTTCTGTACCGCCCACATTGTTCCT
GGAATTGAATTCTCCGGCGATCCTCTGCTCCAGGGACGCAATTTCTCCTATTTTGACACTCAAATTACCCGCCTTGG
CGTCAACTGGGAGGAGCTCCCGATCAATCGTCCTGTGTGCCCTGTTATGAATCACAACAGGGATGGTGCAATGCG
CCATAAGATAACCCAAGGAACCGTAAACTATTGGCCGAACCGTTCGAGGCTTGCCCACCCACGAAGCCCGAGGAT
GGGGGTTTTGTCACTTACCCTCAAAAGGTAGAGCAGAGTATCAAAGCGAGGATGCTTAGTAGCAAGTTCCGCGAGC
ATATCAACCAAGCGCAATTATTCTATAACTCTCTCTCCGAATACGAAAAGCTCCATGTCAATAATGCTTTTTGCTTTG
AGTTGGATCACTGCGATGACCCCATTGTCTACAATAGACTTGTGTCTCGGATTTCTGAAATCGACCATGCCCTCGCC
CAAGCCGTTGCAGTGAAAGTCGGCGCACCGACCCCACCAAGGCCTGGGAGAGACAACCCAGGTCAAACAACCATT
AACCTAAGCCAAAAATACATCAACGACCGTCAGCTGTCCTCTCCCACAATTAAAGGTCGGAGGATCGCCATATTGAT
TGGGGATGGTTACGATTCCGTCGCCTTTGGCACGGTCATAGCCGCGGTGAGCGCCATGGGCGCGCTACCCTTCAT
AATCGGCACGAAGCGGCAACCCATCTTTGCCGACGACGAAGACAGGAATCACTCCAAGGGTGTGACTCCAAACCA
CAACTATACCAGCCAACGCTCCACTTGTTTCGACGCTACTTTCATCCCTGGTGGCTCACATATCAAGGAATTGAGCC
AGCTGGGCCTTATCCAGCACTGGGTTGCCGAGCAGTTCGGACACTGCAAGGCAATTGGCGCTACAGGAGAGGCCA
TCAATCTAATCGTGCAGGCTCTGAGCAACCTGCCTGATTTGGAGGTCGCATCCGCCTCGTCAGGGCATCCAGTCGA
TTGGTACGGCGTTGTCACGTCGAGTAAGCTGCATGAGCCCCATAGTTTGACCGAAGGGATCAAGCTGTTTCCCGAG
GCGAGTGACTTCTTGGGCAAGCTCTTTTATCAGATCTCCCAGCATCGGAATTATGAGCGGGAGATGGCTGGGTTGA
CGGACAAGGTTCCATTTTAAATGGCAACATGGCATCGGTGTGAGTCGCTAGGAAGCAAGTGAAAGTTAATAGTCAG
GCCCCAAAAACAACTATACATACTGTAAACACTAGGTTTAATTTTTGGCTTATATGTTCTTCTGGCAACAATGAATTG
GTTTGTTGCTGTTGCCATTTCTAACAAGTTGTCACAACTAATATATATCCAATCGAATCCATGAAAATGGCATTCTTGT
TCACATATTCTATTCTGTCTGATGCAGATTTGAATTGCTAGTGGTTGAACAAAATTATTGAATTCTAAGCTGTGGGAA
GCCTAGTCACCTTTATTTGCCGATTCATGGTGATCAACAATGTTGTACGTTATGTACGATTCCATCCTCATAACTATG
TGAGGGTTTAGTTACTACTCCTAACTCCTGGCTGAGGGGGAACTAATTGAATTTGAAGAAAACGTCGAACGGATATA
GAACTTGATAAAACCAAAAATTTTCAGATCATGATACTGACGAATGGGTACGCTTTCAGGAATACCTAGATGGATCC
CTA ↑ mRNA end CCAAAAAAAAAAAATAAATAAATAAATAAAAATAAAAATAAAAATAAAATACGAGGCGTAGTATAAAAATGGGAGGGT
AGTATTGAAAAAGGACAACCATCCGTCGCTGGAAGCTATAGAGGCATAGGAAGGTGACACATGAGAAAAGTGTTTC
CCTAATCAGGCCATGGAAAAATAGATTTTGATCTCTCAACGAATGAAGAAAGAAAAATAGTTGAATACAAAGCCAGT
GTTGTAGATATATATGCAACATAAAGGGAATTGAACGTCATAGACAAGAAAAGGAAACCCAGAATTCGTGGGTCGTA
CATAATACGGTTAAACAAATGTCAAAAGAAGGGGAAATTGAAAATTGAAAAGAAAGAGTGAGAAGCCTAACGCTATC
CCCATGTTCTTTTCCCCGTCCTTTCCTCACGCCCATCTCCACATAGGTCTCCACACATCCTTCTCCTTCTCACCACCA
GTCTCCATAGTCTTACTCCTACACATACAAGTCCCAATGACGCC

FIG. 2B

```
   1 CTCGAGTGTCATCTTACCTCCCCGCCCTTCCCACTGCTAAGGGGCAACAACCCACCGTTG
  61 TGACTACTAGGTCGATCTACTTTCTTGGTGCCATCTCCCAGCCAGCCAGACTCTCAAATC
                   I1▼
 121 GCCATCATGGGTGCCGATGATACCTTCAACTCGTACCGATACAAGGATACTCCAACTTAC
   1       M  G  A  D  D  T  F  N  S  Y  R  Y  K  D  T  P  T  Y
                              12▼
 181 ACTGACTCCAATGGCTGTCCGGTTATGGACCCCGAGTCCTCCCAGCGCGTTGGAGAAAAT
  19 T  D  S  N  G  C  P  V  M  D  P  E  S  S  Q  R  V  G  E  N
 241 GGACCCCTGCTCCTTCAGGATTTCCATCTGATCGATCTCCTCGCGCATTTTGACCGCGAG
  39 G  P  L  L  L  Q  D  F  H  L  I  D  L  L  A  H  F  D  R  E
 301 CGGATCCCTGAAAGAGTCGTCCATGCAAAGGGTGCAGGAGCGTACGGTGAATTCGAAGTG
  59 R  I  P  E  R  V  V  H  A  K  G  A  G  A  Y  G  E  F  E  V
                       13▼
 361 CTGGACGACATCAGCGATATCACCACCATTAACATGCTGAAGGGCGTGGGAAAAAAGACA
  79 L  D  D  I  S  D  I  T  T  I  N  M  L  K  G  V  G  K  K  T
 421 AAGCTTGTTACCCGTTTCTCCACTGTTGGTGGGGAGAAGGGATCCGCCGACAGCGCTCGT
  99 K  L  V  T  R  F  S  T  V  G  G  E  K  G  S  A  D  S  A  R
 481 GACCCGAGGGGTTTCTCTACCAAATTCTACACTGAGGAGGGCAACTGGGACTGGGTCTTC
 119 D  P  R  G  F  S  T  K  F  Y  T  E  E  G  N  W  D  W  V  F
 541 AACAACACGCCAGTCTTCTTCTTGCGTGATCCCTCAAAGTTCCCGCTCTTCATCCATACC
 139 N  N  T  P  V  F  F  L  R  D  P  S  K  F  P  L  F  I  H  T
 601 CAGAAGAGGAACCCCCAGACCAACCTCAAGGATGCCACCATGTTTTGGGACTATCTGTCC
 159 Q  K  R  N  P  Q  T  N  L  K  D  A  T  M  F  W  D  Y  L  S
 661 ACCCATCAGGAAGCAATCCACCAAGTTATGCATCTCTTCAGTGATCGTGGTACCCCGTAC
 179 T  H  Q  E  A  I  H  Q  V  M  H  L  F  S  D  R  G  T  P  Y
 721 TCTTACCGCCACATGAATGGCTACTCCGGACACACTTTCAAGTGGCTCACGCCGGACGGG
 199 S  Y  R  H  M  N  G  Y  S  G  H  T  F  K  W  L  T  P  D  G
 781 GGTTTCAACTACGTTCAGATCCATCTCAAGACTGACCAAGGCAGCAAGACTTTGACCAAC
 219 G  F  N  Y  V  Q  I  H  L  K  T  D  Q  G  S  K  T  L  T  N
 841 GAGGAGGCCACTAAACTTGCCGCTGAGAATCCAGATTGGCACACCGAGGACCTCTTCCGG
 239 E  E  A  T  K  L  A  A  E  N  P  D  W  H  T  E  D  L  F  R
 901 GCCATTGAGCGCGGCGAATATCCATCCTGGACCTGTTACGTCCAGGTCCTCAGTCCTCAA
 259 A  I  E  R  G  E  Y  P  S  W  T  C  Y  V  Q  V  L  S  P  Q
 961 CAGGCCGAGAAATTCCGCTGGAACATTTTCGATTTGACCAAGGTCTGGCCCCATTCGGAG
 279 Q  A  E  K  F  R  W  N  I  F  D  L  T  K  V  W  P  H  S  E
1021 GTCCCTCTCCGCCGCTTCGGTCGCCTTGTTCTGAACAAGAACCCACAAAACTACTTCGCT
 299 V  P  L  R  R  F  G  R  L  V  L  N  K  N  P  Q  N  Y  F  A
1081 GAGATGGAACAAGCTGCCTTCTCGCCCTCACACCTGGTCCCCGGCGTCGAGCCCTCCGCA
 319 E  M  E  Q  A  A  F  S  P  S  H  L  V  P  G  V  E  P  S  A
1141 GACCCAGTCCTGCAATCCCGCCTCTTCTCCTACCCAGACACCCATCGCCACCGCCTTGGC
 339 D  P  V  L  Q  S  R  L  F  S  Y  P  D  T  H  R  H  R  L  G
1201 GTCAACTACCAGCAGATCCCCGTCAACTGCCCGCTGCGCGCCTTTAACCCGTACCAGCGC
 359 V  N  Y  Q  Q  I  P  V  N  C  P  L  R  A  F  N  P  Y  Q  R
1261 GACGGTGCGATGGCCGTCAACGGCAACTACGGCGCCAACCCCAACTACCCATCCACCTTC
 379 D  G  A  M  A  V  N  G  N  Y  G  A  N  P  N  Y  P  S  T  F
1321 CGCCGGATGAATTACATGCCCGTCAAAGCCAGCCAGGAGCACGAGAAGTGGACCGGTGCT
 399 R  R  M  N  Y  M  P  V  K  A  S  Q  E  H  E  K  W  T  G  A
1381 GTCCTCGCGAAACAGCTCCCCGTCACCGATGAGGATTTCGTGCAAGCCAATGGCCTCTGG
 419 V  L  A  K  Q  L  P  V  T  D  E  D  F  V  Q  A  N  G  L  W
1441 CAGGTTCTGGGTCGCCAACCTGGCCAGCAAGCGAACTTTGTCAAGAATGTGGCCGGCCAC
 439 Q  V  L  G  R  Q  P  G  Q  Q  A  N  F  V  K  N  V  A  G  H
1501 TTGTGCAATGCTGAGCAGAAAGTGCGCAAGGCGGCGTATGGCATGTTCATCCGCGTCAAT
 459 L  C  N  A  E  Q  K  V  R  K  A  A  Y  G  M  F  I  R  V  N
1561 AAGGACTTGGGAAGTTCCATTGAGTCGTCAACAGAAGCTTTGGTGGCGTCGCAGGCGCAG
 479 K  D  L  G  S  S  I  E  S  S  T  E  A  L  V  A  S  Q  A  Q
1621 TCGCAGCCGCGCCTGTAGCCGCGTTGAGAACGTTTTATGTCGTTCGGTTGGATATTGGGG
 499 S  Q  P  R  L  *
1681 TTGACAAGTTTGAATATTGAACGTCGGTTATGATGGTTGAATTGACTTTTATGTTATTTT
1741 TTTCATTTTTACCCTTTTATTTTCCTTTTATTTTCTTTTCACCATTCTAGGTACTTGGCA
1801 GGATATGAATGAATTTAAACATCCTTGGATAACGACATAAGAGGATAGGCCGCAAGACTA
1861 GTTATGCAGGACAACTCTGGTGTTTTCTTTCGGGGCCCTAGATATTCACTATAGTTTTGG
1921 TACTTATATCAGAACATACTTGGAGGATCCGTGGCTATCGTGACCCATTTTCCATTCCAG
1981 GGCCAAAATTTTCCAAACAAATTATTTTTCTATT 2014
```

FIG. 3

CGTGCTTAGACACAATATAGCTAGAGAGATAAAGAATTCTAATATGGTAATTCTGCTAGAATGTACTGTATTTGTATG
AGGAACTTTTCACAAGTGTAAAACTATTTAATCTTTTCAAGAAATATGATGGCAAATAAAATAAAAATAAGGGACTTCA
AGAACTAACTCTATAGTGAGATAAATAGATTAGCTAGTGTTGCAAAATCCATNTAGCAGATGCATGCCGCGTATGGC
ATACCCTCTGTTGGCAAGGAGTGCCCCAGACCTAGAATTCCATGGTTGGGCAAGTCATGTTTCTTCCTGCAACCAA
GATAAGGCAGGCCACCTAAATTCTAATCAAAGCCTCTGAGTTCTCACACTTTTGAGTACCATTTATATAGAAGAAGCC
ATTGAATCTATAGAATATGTAGACTGATAGCAAGCCGATCCTGCTGGCGCTAAGAGGAAATATTTCCTTGGCAGCTC
AGTGGAGGAAGTTTGGCGGTTCTATATAGACGTATCTTCCCTCGTTTGCAGGAAAGCAGAGCTAGATTGGTATTGAG
GACCTTGAGGTGGTATTCCATTCTATTTTTATGTCTAAATTCTTTAAATGTGGCAAACGAGCTGCACCCCGGCGGTG
CGCGTAAAGCTCGAAACATGCACAGACAGCGCACAGAGACAGCGCACAGAGACAGAGCACAGAGACAGAGCATAG
AGACAGGCGGCAGTCCTCCCTCGCAAATATCGCTGTAGTCGGTTTGGTGGCTAAGCTTGAAGCAGTTGGGGGCTTA
GAAAGCCCTGACAGTTCAACGGCCAAAGGGAGGAAACAGAGAGTTACTTCGTTTGTCTACCGAATTACAAGGCAAC
TTAAGTACCAGTACATCGATGAGCGGCCCCACGCGGCTCATCCTCGGGGACGATTCCATGGCGGGTCTCGGCGA
TATATATAGACACCCCTTTCCCCTCTTTAGTGCGACCCCGTCATTGTTCCTCCCATAAACCTCTTCTGCTTCCAAGT
↓ mRNA start
CTCGAGTGTCATCTTACCTCCCCGCCCTTCCCACTGCTAAGGGGCAACAACCCACCGTTGTGACTACTAGGTCGAT
CTACTTTCTTGGTGCCATCTCCCAGCCAGCCAGACTCTCAAATCGCCATCATGGGTGCCGATGATACCTTCA*GTATG*
*TGCTCACCATTCCAGCACGGTCC*

Passay5' (#1)                Passay5' (#2)
     —————————▶         —————————▶

ACTAGTTCC*GAGCTTCGATACTTAATCTAG*ATATATACATG*GACGGACGTGTCTAAAAC*GCGGGCAACGACATCGA
AGACAGGGGCTAACCAATATCCTGCCATATAGACTCGTACCGATACAAGGATACTCCAACTTACACTGACTCCAATG
GCTGTCCGG*TAGGTTTCGC*

Passay3' (#3)            Passay5' (#3)
    ◀—————————         —————————▶

GTCTGCTCTTAATAATTTGT*CGTATTGTCCCCACTAGATCGGCTATCATTAGAGAACAGATC*AGCGAGAGATACACT
AATTAGAAACGTTGGATCCCGTCTAATGCTGATGGTACGGTTATATAGGTTATGGACCCCGAGTCCTCCCAGCGCG
TTGGAGAAAATGGACCCCTGCTCCTTCAGGATTTCCATCTGATCGATCTCCTCGCGCATTTTGACCGCGAGCGGAT
CCCTGAAAGAGTCGTCCATGCAAAGGGTGCAGGAGCGTACGGTGAATTCGAAGTGCTGGACGACATCAGCGATAT
CGTAAGTCAAAG

Passay3' (#2)            Passay3' (#1)
    ◀—————————         ◀—————————

ACTCTTCTTGTCCTTTTTGTTT*GCAACCATCAGCTGCGGCAC*TGC*AGACATACCCAGAACCCTG*TTCTATGCTAAC
GATTACTATAGACCACCATTAACATGCTGAAGGGCGTGGGAAAAAAGACAAAGCTTGTTACCCGTTTCTCCACTGTT
GGTGGGGAGAAGGGATCCGCCGACAGCGCTCGTGACCCGAGGGGTTTCTCTACCAAATTCTACACTGAGGAGGGC
AACTGGGACTGGGTCTTCAACAACACGCCAGTCTTCTTCTTGCGTGATCCCTCAAAGTTCCCGCTCTTCATCCATAC
CCAGAAGAGGAACCCCCAGACCAACCTCAAGGATGCCACCATGTTTTGGGACTATCTGTCCACCCATCAGGAAGCA
ATCCACCAAGTTATGCATCTCTTCAGTGATCGTGGTACCCCGTACTCTTACCGCCACATGAATGGCTACTCCGGACA
CACTTTCAAGTGGCTCACGCCGGACGGGGGTTTCAACTACGTTCAGATCCATCTCAAGACTGACCAAGGCAGCAAG

FIG. 4A

```
ACTTTGACCAACGAGGAGGCCACTAAACTTGCCGCTGAGAATCCAGATTGGCACACCGAGGACCTCTTCCGGGCC
ATTGAGCGCGGCGAATATCCATCCTGGACCTGTTACGTCCAGGTCCTCAGTCCTCAACAGGCCGAGAAATTCCGCT
GGAACATTTTCGATTTGACCAAGGTCTGGCCCCATTCGGAGGTCCCTCTCCGCCGCTTCGGTCGCCTTGTTCTGAA
CAAGAACCCACAAAACTACTTCGCTGAGATGGAACAAGCTGCCTTCTCGCCCTCACACCTGGTCCCCGGCGTCGAG
CCCTCCGCAGACCCAGTCCTGCAATCCCGCCTCTTCTCCTACCCAGACACCCATCGCCACCGCCTTGGCGTCAACT
ACCAGCAGATCCCCGTCAACTGCCCGCTGCGCGCCTTTAACCCGTACCAGCGCGACGGTGCGATGGCCGTCAACG
GCAACTACGGCGCCAACCCCAACTACCCATCCACCTTCCGCCGGATGAATTACATGCCCGTCAAAGCCAGCCAGG
AGCACGAGAAGTGGACCGGTGCTGTCCTCGCGAAACAGCTCCCCGTCACCGATGAGGATTTCGTGCAAGCCAATG
GCCTCTGGCAGGTTCTGGGTCGCCAACCTGGCCAGCAAGCGAACTTTGTCAAGAATGTGGCCGGCCACTTGTGCA
ATGCTGAGCAGAAAGTGCGCAAGGCGGCGTATGGCATGTTCATCCGCGTCAATAAGGACTTGGGAAGTTCCATTGA
GTCGTCAACAGAAGCTTTGGTGGCGTCGCAGGCGCAGTCGCAGCCGCGCCTGTAGCCGCGTTGAGAACGTTTTAT
GTCGTTCGGTTGGATATTGGGGTTGACAAGTTTGAATATTGAACGTCGGTTATGATGGTTGAATTGACTTTTATGTTA
TTTTTTTCATTTTTACCCTTTTATTTTCCTTTTATTTTCTTTTCACCATTCTAGGTACTTGGCAGGATATGAATGAATTTA
AACATCCTTGGATAACGACATAAGAGGATAGGCCGCAAGACTAGTTATGCAGGACAACTCTGGTGTTTTCTTTCGGG
GCCCTAGATATTCACTATAGTTTTGGTACTTATATCAGAACATACTTGGAGGATCCGTGGCTATCGTGACCCATTTTC
CATTCCAGGGCCAAAATTTTCCAAACAAATTATTTTTCTATT↑ mRNA end AGTTATCTTGTCGGGTCATCATTCTGCTTTTGAGTTGGGTATCTCTGAAATATAAGCTGCTGCTATAATTACGTGGAA
CTCCTTTTCCAATCAGTCGTTGAAGTGCATTACGGTGTAGAAATTATTTGATGTCTCAACTGAGTTTCCACTTTATATC
AATTACGGATCGCAATTGAGGCGCATTTATTTATACATGACAAGGACTACACGTATATATATATCGACAATAGAAGAT
TTATGCAGATATAGTAAAATTGTTGTGGTAGTAGTTATTTCCGTTTGAGTGGCCCATGGCTGGTTTGGTTGGGTTACA
TCCTAGCAAGGCAAGTTTTCCACACCAATCCACCTTTATTTGTGGTCGGTCCTGTAAATATGTAGCGCGGCATGGAC
CTTACTTAGTTACAGGCAACGAAATTTTTCTTTAACCAAGCATCCACATGAAGTTTTAGAGGCAAATAACTATATGCA
CATTTTCCTGGGCTATGTCCTCTGTCTGAGCA
```

FIG. 4B

Intron Sequences

CATA introns:

Intron 1 – (SEQ ID NO: 7)

GTTTCATATACCTCTCGTCTACCTCCCTATTGTGTTCCATGTCTTCCAAGCTT
TGCGGGCAACATATGATAACCATCGAGTTAG

Intron 2 – (SEQ ID N: 8)

GTAAGTATTGATTGATATCCCATTTCTTCATTATGGATATTTTCGTGTTGATC
GTTTTACAACTCGACATTAG

CATP introns:

Intron 1 – (SEQ ID NO: 9)

GTATGTGCTCACCATTCCCAGCACGGTCCACTAGTTCCGAGCTTCGATACTT
AATCTAGATATATACATGGACGGACGTGTCTAAAACGCGGGCAACGACATC
GAAGACAGGGGCTAACCAATATCCTGCCATATAG

Intron 2 – (SEQ ID NO: 10)

GTAGGTTTCGCGTCTGCTCTTAATAATTTGTCGTATTGTCCCCACTAGATCG
GCTATCATTAGAGAACAGATCAGCGAGAGATACACTAATTAGAAACGTTGGA
TCCCGTCTAATGCTGATGGTACGGTTATATAG

Intron 3 – (SEQ ID NO: 11)

GTAAGTCAAAGACTCTTCTTGTCCTTTTTGTTTGCAACCATCAGCTGCGGCA
CTGCAGACATACCCAGAACCCTGTTCTATGCTAACGATTACTATAG

FIG. 5

```
Hc CatA    1  ~~~~~~~~~~~~~~~MTSKVEEGLQRVKEIVENMQPGEQKVADLARD.ITDVN.GCLPETTDHGVKVSN
Af catA    1  ~~~~~~~~~~~~~~~MATKIAGGLHRAQEVLQNTSSKSKKLVDLERD.TADAH.TQQPLTTDHGVRVSN
En catA    1  ~~~~~~~~~~~~~~~MATSILAGLQRAQQAVQDTALKNKKLVDLSHD.TVNVH.TDQEQRTDFGVALTD
An catR    1  MRHFWLLPAVAGIAGAQCPYLSGEMSFTQE..QDNAGDTIEVTEQPIDNTLYVNDTGSYMTTDFGTPLSD Hc CatA   53  TDEWLRLASENQTGPLLEYQIAREKIHRFDHERIPERVVHARGTGAEGHFKLFESAADVTSAGVLTDTS
Af catA   53  TDQWLRVTNDRRTGPSLLEDQIAREKIHRFDHERIPERVVHARGTGAEGNFKLKESIEDLTYAGVLTDTS
En catA   53  PDHWLRVTNETHSGPSLLEDHIAREKIHRFDHERIPERVVHARGTGALGNFTLKESIEDLTYAGVLTDTS
An catR   69  QTS.LKAGPR...GPLLLEDFIFRQKLQRFDHERVPERVVHARGAGAVGTFKSYADWSNVTAADFLSAND Hc CatA  123  RTTPVFVRFSTVQGSKGSEDTVRDVRGFATKFYTEEGNWDLVGNNIPVFFIQDAVKFPDFVHAVKPEPHN
Af catA  123  RNTPVFVRFSTVQGSRGSADTVRDVRGFAVKFYTDEGNWDIVGNNIPVFFIQDAVKFPDFVHAVKPEPHN
En catA  123  RNTPVFVRFSTVQGSRGSADTVRDVRGFAVKFYTDEGNWDIVGNNIPVFFIQDALKFPDFVHAVKPEPHN
An catR  135  KETPMFCRFSTVVGFRGSVDTARDVHGHACRFYTDEGNMDIVGINFAFFFIQDALQFPDLVHATKPMPNN Hc CatA  193  EVPQGQTAHNNFWDFVYMHPEATHMFMWAMSDRAIPRSYRMMQGFGVNTFVLVNKQGKRHFVKFHWMPEL
Af catA  193  EVPQAQTAHNNFWDFVYLHPEATHMFMWAMSDRAIPRSYRMMQGFGVNTFALVNKEGKRHFVKFHWIPHL
En catA  193  EVPQAQTAHNNFWDFVYLHPEATHMFMWAMSDRAIPRSYRMMQGFGVNTFSLVNKEGKRHFVKFHWIPHL
An catR  205  ELPQAATAHTSAWDEFSQQSTALHSADWLMSGNGIPRSERHMNCMGVHSERFVAANGTSKVVRTPWKSQQ Hc CatA  263  GVHSLVPDESEKLGGQDPDFHRKDLMEAIDNKVYPKWKFGIQVLPEEKEHDFDFDILDPTKIWPESLLPV
Af catA  263  GVHSLVWDEALKLGGQDPDFHRKDLMEAIDNKAYPKWDFAIQVIPEEKQDDFEFDILDATKIWPENLVPL
En catA  263  GVHSLVWDEALKLAGQDPDFHRKDLMEAIDNKAYPKWDFAIQAIPEEDQDKFEFDIEDATKVWPEEQVPL
An catR  275  GVASLVWDEAQAAAGKNSDYHRQDLYNAMPNGHYPKYELQAQEMDEADMLRFGFDLLDPTKLVPEEMVPY Hc CatA  333  RYIGEMELNRNVDEFFPQTEQVAFCTAHIVPGIEFSGDPLLQGRNFSYFDTQIMRL.GVNWEELPINRPV
Af catA  333  RVIGELELNRNVDEFFPQTEQVAFCTSHIVPGIDFTDDPLLQGRNFSYFDTQISRL.GINWEELPINRPV
En catA  333  RVVGELELNRNLDEFFPETEQVAFCTSHIVPGIDFSDDPLLQGRNFSYQDTQISRL.GVNWEELPINRPV
An catR  345  TPLGMMELNANPTNMEAEVEQAEFQPGHKVPGIDFLDDPLLQGRLFSYLDTQLTRHGCPNEEQPMNRPR Hc CatA  402  CPVMNHNRDGAMRHKITQGTVNYWPNRFEACPPTKPE....DGGFVTYPQKVEQSIKARMLSSKFREHIN
Af catA  402  CPVLNHNRDGQMRHRITQGTVNYWPNRFEAVPPTGKSSGVGGGEFTTYPQRVE.GIKNRALNDKFREHHN
En catA  402  CPFLNHNRDGAKRHRITKGTVNYWPNRFEANPPASDK......GFKSHPAPLT.GRRRDLLPKFKEYHN
An catR  415  KPVHNNNRDGFGQQQLTPTNNWAMTPNSMSNGYPMQANQL.QGHGEFIAPYRYASGHLVRQTSPTFNDHWS Hc CatA  468  QAQLFYNSLSEYEKLHVNNAFCFELDHCDDPIVYNRLVS.RISEIDHALAQAVAVKVGAPTPPRPGRDNP
Af catA  471  QAQLFYNSVSEHEKLHMKKAFSFELDHCDDPTVYERLAGHRLAEIDLELAQKVAEMVGAPIPAKALKQNH
En catA  465  QAQLFYNSLSEVEKMHVKKAFSFELDHCDDPIVYERLAGQRLAEIDLPLAQAVAEMVGAPIPTKALRDNH
An catR  484  QPAMFVNSLIPAEQQMVVNAIVFENSKVNSEHVRKNVVNQ.LNMVANNLAVRVARGIGLDEESP...NPT Hc CatA  537  GQTTINLSQKYINDRQLSSPTIKGRRIAILIGDGY.DSMAFGTVIAAVSAMGALEFIIGTKRQPIHADDE
Af catA  541  GRRAPHLSQTEFIPK...NPTIASRRIAILIGDGY.DPVASTGHKTAIKAASALPFIIGTKRSAIYAT.E
En catA  535  GKTSVRLSQFDFTPK...APGIISRRIAILIGDGY.DKIAFNGMKAAILAAASAPLRHWHQTSAIYAQGE
An catR  550  YYTSNKTSNVGTFGKPLLS..IEGLQVGFIASNSHPESIKQGQAMAAQFSAAGVDLNTVTEA...VADGV Hc CatA  606  DENHSKGVTPNHN....YTSQRSTCFDATFI..PGGSHIKELSQLGLIQHWVAEQFGHCKATGATGEAIN
Af catA  606  DKTSSKGEIPDHH....YDGQRSTMFDATFI..PGGPHVATLRQNGQIKYWISETFGHLKALGATGEAVD
En catA  601  DKNSSKGVIPDHM....YDGMRSTMFDATFI..PGGSHIETIQKNGQIRYWIAETFGHLKALGAMGEAAQ
An catR  615  NTTYALSDAIDFDALIIADGVQSLFASPALANQMNSTATSTLYPPARPFQILVDSERYGKPVAAVGSGSV Hc CatA  670  LIVQA..LSNLPDLEVASASSGHPVD...WYGVVTSSKLHEPHSLEEGIKLFPEASDFVGKLFYQISQHR
Af catA  670  LVKET..LSGTLHVQVASSQSPEPVE...WYGVVTAGGKQKPESFKESVQLLKGAEDFVGKFFYQISQHR
En catA  665  LVKEV..LGNVMGVQFAGADSAEPVE...WYGVVTARGPESAESLSEGFKVLKDAGFDETSKFFYQISQHR
An catR  685  AIKNAGIDSSRSCVYTGSSETTEKIAKEVLEGLYTFRFVDR.FALDE~~~~~~~~~~~~~~~~~~~~

Hc CatA  735  NYEREMAGLTDKVPF
Af catA  735  NYQRELDGLASTIAF
En catA  730  NWQRELDGLASTVAF
An catR  731  ~~~~~~~~~~~~~~~
```

FIG. 6

```
Hc_CATP    1 ---MGADDTFNSYR-YKDTPTYTDSNGCPVMDPESSQRVGEN----------GPLLLQDFHLIDLLAHFD
En_CATC    1 ---MGQNDDQKTYR-YNESPVYTTSNGCPVMDPQASQRVGPN----------GPLLLQDFNLIDLLAHFD
Sc_CTA1    1 MSKLGQEKNEVNYSDVREDRVVTNSTGNPINEPFVTQRIGEH----------GPLLLQDFNLIDSLAHFN
Ca_CTA1    1 --------------MAPTFTNSNGQPIPEPFATQRVGQH-----------GPLLLQDFNLIDSLAHFD
Hp_CATG    1 --------------MSNPPVETTSQGCPVSDPFTTQRIPLDSTGYKYAPPIGPLLLQDFKLIDTLSHFD
Sp_CTA1    1 ----------MNSKDSNTVPVYTTNTGCPIFNPMAAARVGKG---------GPVLLQDSHLIDVFQHFD

Hc_CATP   57 RERIPERVVHAKGAGAYGEFEVLDDISDITTINMLKGVGKKTKLVTRFSTVGGEKGSADSARDPRGFSTK
En_CATC   57 RERIPERVVHAKGAGAYGEFEVTDDISDITVIDMLKGVGKKTKTFVRFSTVGGEKGSPDSARDPRGFACK
Sc_CTA1   61 RENIPQRNPHAHGSGAFGYFEVTDDITDICGSAMFSKIGKRTKCLTRFSTVGGDKGSADTVRDPRGFATK
Ca_CTA1   44 RERIPERVVHAKGSGAYGVFEVTDDITDICAAKFLDTVGKKTRIFTRFSTVGGELGSADTARDPRGFATK
Hp_CATG   56 RERIPERVVHAKGAGAYGVFEVTDDITDVCSAKFLDTVGKKTRIFTRFSTVGGEKGSADTARDPRGFATK
Sp_CTA1   51 RERIPERVVHAKGSGAFGEFECTDDITKYTKHTMFSKVGKKTPMVARFSTVGGERGTPDTARDPRGFALK

Hc_CATP  127 FYTEEGNWDWVFNNTPVFFLRDPSKFPLFIHTQKRNPQTNLKDATMFWDYLST---HQEAIHQVMHLFSDR
En_CATC  127 FYTEEGNWDWVFNNTPVFFLRDPSKFPMFIHTQKRNPQTNLKDATMFWDYLST---HQEAVHQVMHLFSDR
Sc_CTA1  131 FYTEEGNLDWVYNNTPVFFIRDPSKFPHFIHTQKRNPQTNLRDADMFWDFLTTPENQVAIHQVMILFSDR
Ca_CTA1  114 IYTEEGNLDLVYNNTPVFFIRDPIKFPHFIHTQKRNPETHLKDANMFWDYLTS---NEESIHQVMVLFSDR
Hp_CATG  126 FYTEDGNLDLVYNNTPIFFIRDPIKFPHFIHTQKRNPATNLKDPNMFWDYLNA---NDESIHQVMYLFSNR
Sp_CTA1  121 FYTDEGIFDMVGNNTPVFFLRDPAKFPLFIHTQKRNPQNDMKDATMFWDYLSQ---NAESIHQVMILFSDL

Hc_CATP  195 G-TPYSYRHMNGYSGHTEKWLTPDGGENYVQIHLKTDQGSKTLTNEEATKLAAENPDWHTEDLFRAIERG
En_CATC  195 G-TPYSYRHMNGYSGHTYKWIKPDGTENYVQLHLKTGQGNKTETDAEATRLAAENPDWHTQDLFNAIARG
Sc_CTA1  201 G-TPANYRSMHGYSGHTYKWSNKNGDWHYVQVHIKTDQGIKNLTIEEAKIAGSNPDYCQODLFEAIQNG
Ca_CTA1  182 G-TPASYREMNGYSGHTYKWSNKKGEWEYVQVHFISDQGIKTLNEEAGALAGSNPDYAQEDLFKNIAAG
Hp_CATG  194 G-TPASYRTMNGYSGHTYKWYNSKGEWVYVQVHFIANQGVHNLLDEEAGRLAGEDPDHSTRDLWEAIEKG
Sp_CTA1  189 GGTPYSYRFMDGFSSHTYKFVNDKGEFYYCKWHFITNQGTKGLTNEEAAALDGSNPDHARQDLFEAIERG

Hc_CATP  264 EYPSWTCYVQVLSPQQAEKFRWNIFDLTKVWPHSEVPLRRFGRLVLNKNPQNYFAEMEQAAFSPSHLVPG
En_CATC  264 EYPSWTCYVQTLSPEQAEKFRWNIFDLTKVWPQSEVPLRRFGRFTLNKNPENYFAEVEQAAFSPSHLVPG
Sc_CTA1  270 NYPSWTVYIQTMTERDAKKLPFSVFDLTKVWPQGQFPLRRVGKIVLNENPLNFFAQVEQAAFAPSTTVPY
Ca_CTA1  251 NYPSWTAYIQTMTEAEAKEAEFSVFDLTKVWPHRKYPMRRFGKFTLNENPENYFAEVEQAAFSPAHTVPY
Hp_CATG  263 DYPSWECYFQTMTLEQSKKLPFSVFDLTKVWPHKDFPLRHFGRFTLNENPKNYYAETEQIAFSPSHTVPC
Sp_CTA1  259 DYPSWTLYVQVMTPQEAEKYRYNIFDLTKVWPHKDVPMQRVGRFTLNQNPTNFFADIEQAGFSPSHMVPG

Hc_CATP  334 VEPSADPVLQSRLFSYPDTHR-HRLG-VNYQQIPVNCPLR---AFNPYQRDGAMAVNGNYGANPNYP-STF
En_CATC  334 VEPSADPVLQARLFSYPDTHR-HRLGTSNYQSIPVNCPLR---AFTPEHRDCAMSVNGNHGANPNYP-STF
Sc_CTA1  340 QEASADPVLQARLFSYADAHR-YRLG-PNFHQIPVNCPLR---AYTHKQPGDVFVQARNLYR-VLGKQPGQQNLAYNICIHVEGA
Ca_CTA1  321 MEPSADPVLQSRLFSYADTHRPHRLG-TNYTQIPVNCPVTGAVFNPHSRDGAMTVNGNLGSHPNYL-ASD
Hp_CATG  333 MEPSNDPVLQSRLFSYPDTHR-HRLG-PNYHQIPVNCPLKSGSFNPINRDGPMCVDGNLGGTPNYANAYN
Sp_CTA1  329 IEVSADPVLQVRTFSYPDTHR-HRLG-ANFEQIPVNSPKCP-VFN-YSRDGPMNVNGNQGNWPNYP-SSI

Hc_CATP  399 RRMNYMPVKA----SQEHEKWTGAVLAKQLPVTD--EDFVQANGLWQ-VLGRQPGQQANFVKNVAGHICNA
En_CATC  400 RPLQYKPVKA----SQEHEKWAGSVVTEQLPVTD--EDFVQANGLWK-VLGRQPGQQENFVGNVAGHICNA
Sc_CTA1  407 KSYTYIQQDRP-IQQHEQEVWNGPAIPYHWATSPGDVFVQARNLYR-VLGKQPGQQNLAYNICIHVEGA
Ca_CTA1  389 KPVEFKQFSS---FQEDQEVWNGAATPEHWKATP--ADFKQAQELWK-VLKRYPNQQEHLAHNIAVHAAGA
Hp_CATG  401 CPIQYAVSPKASGNKPDEKYTGEVVPYHWEHTD---YDYFQPKMFWK-VLGRTPGFQESLVKNVANHVSAA
Sp_CTA1  394 RPLAKVQYEP---DEGHEKWVGQVTYHMDEITD--VDFEQPRAFWQNVLGKKPGQQDNFVKNVAGHLSGA

Hc_CATP  463 EQKVRKAAYGMFIRVNKDLGSSIESSTEALVASQA----QSQPRL---------
En_CATC  464 HPRVRQATYGMFRRVNADLGKRIEKATEK-KATEA----R--ARL---------
Sc_CTA1  475 CPQIQORVYDMFARVDKGLSEAIKKVAEAKHASEL----SSNSKF---------
Ca_CTA1  454 DAAIQDRVFAYFGKVSQDLADAIK-----KEVLEL----SPRK-----------
Hp_CATG  468 DEFTQDRVYEYFSKAEPIIGDLIR------KKVQELKRKASSPSKI--------
Sp_CTA1  459 ISPVRERQYGVFTRVDSELGRRIREATEAEVKKMEEKAPKPINKGEPHMFQGSS
```

FIG. 7

Southerns using *CATA* introns as probes

CATA Intron 1

Southerns using *CATP* introns as probes
CATP Introns 1 & 2
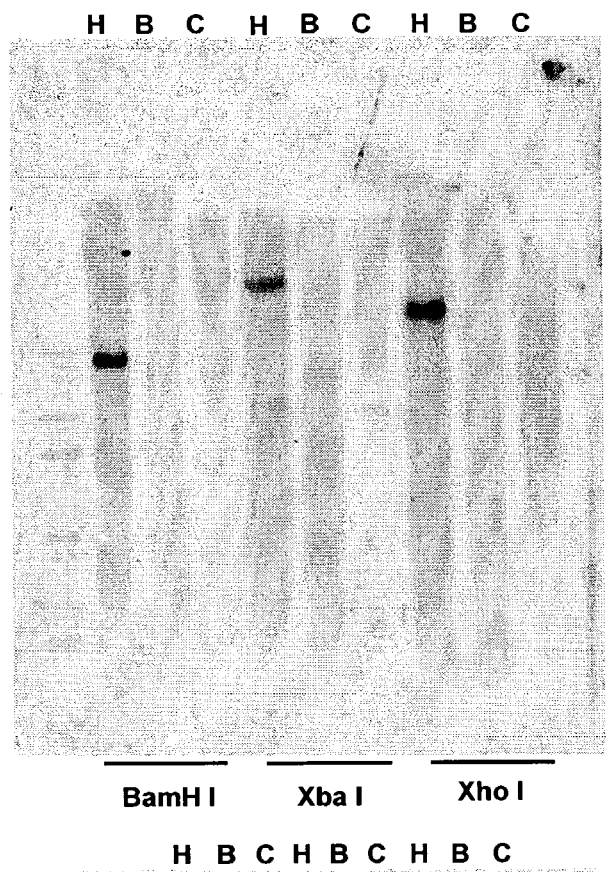
CATP Intron 3
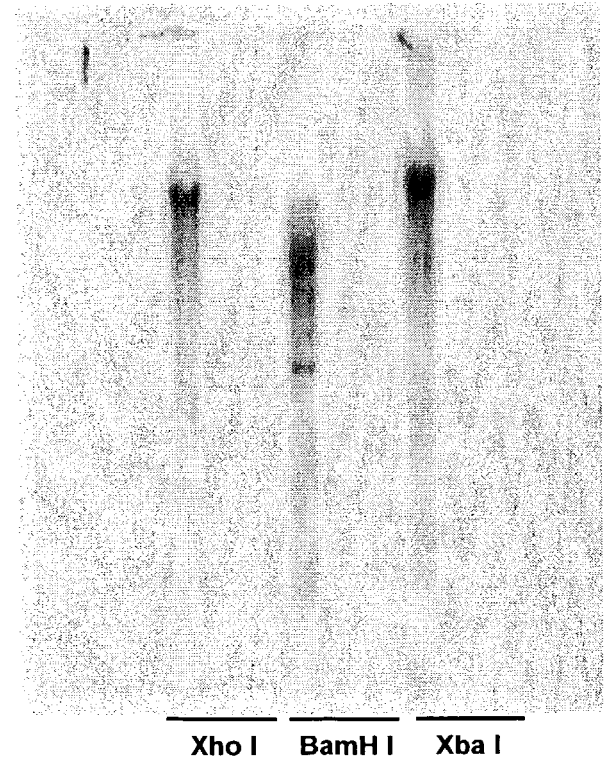
FIG. 8B

Primers for PCR Assays

| CATA 5' Primers: | CATP 5' Primers: |
|---|---|
| Primer 1 (SEQ ID NO: 12)<br>TGCGGGCAACATATGATAAC | Primer 1 (SEQ ID NO: 18)<br>GAGCTTCGATACTTAATCTAG |
| Primer 2 (SEQ ID NO: 13)<br>GATAACCATCGAGTTAGATCC | Primer 2 (SEQ ID NO: 19)<br>GACGGACGTGTCTAAAACG |
| Primer 3 (SEQ ID NO: 14)<br>CGTCCGCTGGTGTTCTAAC | Primer 3 (SEQ ID NO: 20)<br>GCTATCATTAGAGAACAGATC |
| CATA 3' Primers: | CATP 3' Primers: |
| Primer 1 (SEQ ID NO: 15)<br>CGATCAACACGAAAATATCC | Primer 1 (SEQ ID NO: 21)<br>CAGGGTTCTGGGTATGTCT |
| Primer 2 (SEQ ID NO: 16)<br>TATCAATCAATACTTAC | Primer 2 (SEQ ID NO: 22)<br>GTGCCGCAGCTGATGGTTG |
| Primer 3 (SEQ ID NO: 17)<br>GACATCACGGACTGTATCG | Primer 3 (SEQ ID NO: 23)<br>GATCTAGTGGGGACAATACG |

FIG. 9

CATA
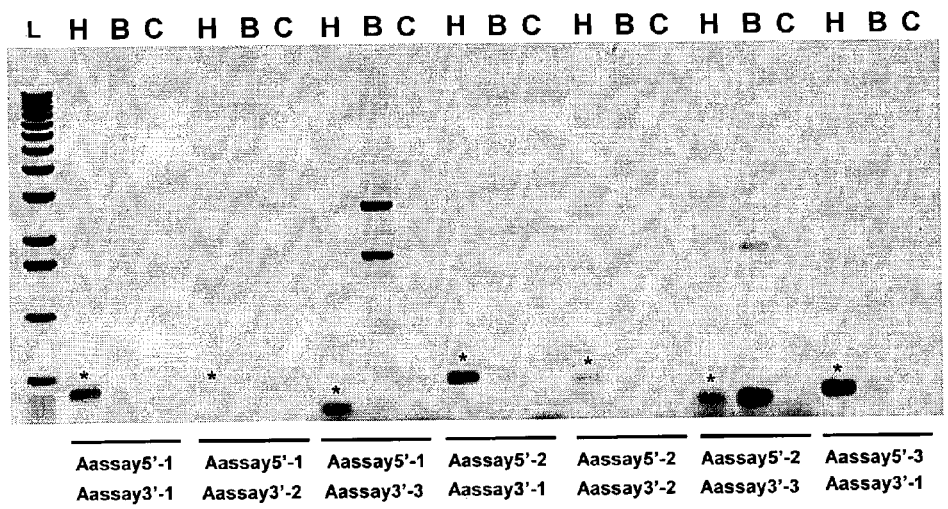
CATP
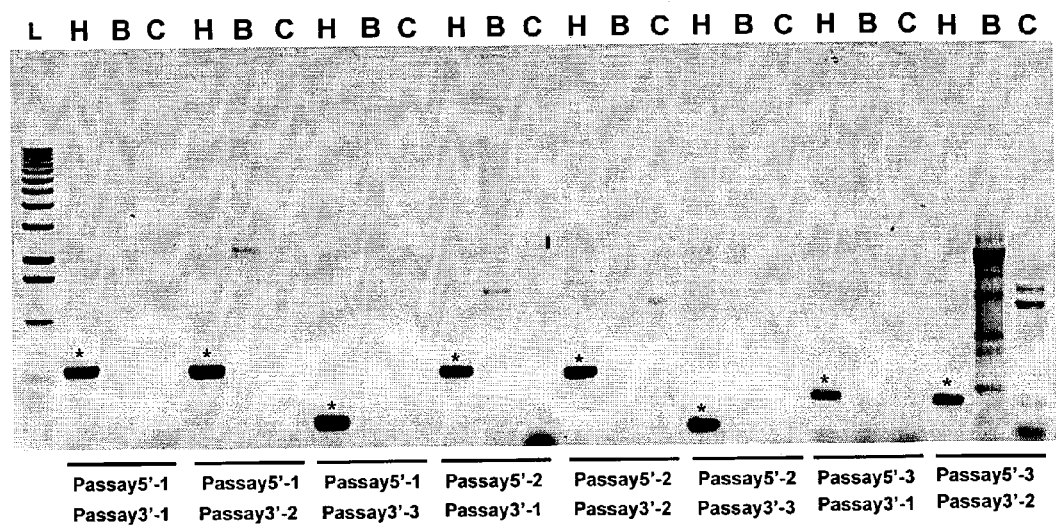
FIG. 10

SEQUENCE LISTING

```
<160> NUMBER OF SEQ ID NOS: 48

<210> SEQ ID NO 1
<211> LENGTH: 2537
<212> TYPE: DNA
<213> ORGANISM: Histoplasma capsulatum CATA
<220> FEATURE:
<221> NAME/KEY: CDS
<222> LOCATION: (65)..(2311)
<223> OTHER INFORMATION:

<400> SEQUENCE: 1
```

-continued

```
attcacaaaa gttccagttt caactttgaa aaagaaccag agaatatttt tttcatcgcc        60 ccca atg act agc aag gtt gaa gaa ggg ctc cag agg gtc aag gag ctg       109
     Met Thr Ser Lys Val Glu Glu Gly Leu Gln Arg Val Lys Glu Leu
     1               5                   10                  15 gtg gaa aat atg cag cca gga gag caa aag gtc gca gac ctc gcc cgc       157
Val Glu Asn Met Gln Pro Gly Glu Gln Lys Val Ala Asp Leu Ala Arg
                    20                  25                  30 gat act aca gac gtc aac gga tgc ctc ccc ttc acc act gac cat gga       205
Asp Thr Thr Asp Val Asn Gly Cys Leu Pro Phe Thr Thr Asp His Gly
                35                  40                  45 gtc aaa gtt agc aat acg gac ttt tgg ctt cga ctt gca tcc gaa aat       253
Val Lys Val Ser Asn Thr Asp Phe Trp Leu Arg Leu Ala Ser Glu Asn
        50                  55                  60 caa acc ggc cca ttg ctt ttg gag gat cag att gct cgt gaa aag atc       301
Gln Thr Gly Pro Leu Leu Leu Glu Asp Gln Ile Ala Arg Glu Lys Ile
65                  70                  75 cat cga ttt gac cat gaa aga atc cca gaa cgt gtt gtc cat gca cga       349
His Arg Phe Asp His Glu Arg Ile Pro Glu Arg Val Val His Ala Arg
80              85                  90                  95 gga aca ggt gct ttt ggg cac ttc aag ctc ttc gag agc gcg gca gac       397
Gly Thr Gly Ala Phe Gly His Phe Lys Leu Phe Glu Ser Ala Ala Asp
                    100                 105                 110 gtg acg tcc gct ggt gtt cta act gac acg tcc cga act act ccg gtg       445
Val Thr Ser Ala Gly Val Leu Thr Asp Thr Ser Arg Thr Thr Pro Val
                115                 120                 125 ttc gtt cgg ttt tcc acc gtc cag ggc agc aaa ggc agt ttc gat aca       493
Phe Val Arg Phe Ser Thr Val Gln Gly Ser Lys Gly Ser Phe Asp Thr
            130                 135                 140 gtc cgt gat gtc aga ggt ttc gct acc aaa ttc tat acg gaa gaa ggc       541
Val Arg Asp Val Arg Gly Phe Ala Thr Lys Phe Tyr Thr Glu Glu Gly
145                 150                 155 aac tgg gat ctt gtt ggc aat aac att cct gta ttc ttc att caa gat       589
Asn Trp Asp Leu Val Gly Asn Asn Ile Pro Val Phe Phe Ile Gln Asp
160                 165                 170                 175 gct gtg aaa ttc cca gat ttt gtt cat gct gtg aag ccg gaa cct cat       637
Ala Val Lys Phe Pro Asp Phe Val His Ala Val Lys Pro Glu Pro His
                180                 185                 190 aac gaa gtt ccc cag gga caa aca gca cat aac aac ttc tgg gac ttt       685
Asn Glu Val Pro Gln Gly Gln Thr Ala His Asn Asn Phe Trp Asp Phe
                195                 200                 205 gta tat atg cat cct gag gcg acg cat atg ttc atg tgg gct atg tcg       733
Val Tyr Met His Pro Glu Ala Thr His Met Phe Met Trp Ala Met Ser
            210                 215                 220 gac agg gct att ccg cga tca tat cgg atg atg caa gga ttt ggt gtt       781
Asp Arg Ala Ile Pro Arg Ser Tyr Arg Met Met Gln Gly Phe Gly Val
225                 230                 235 aat act ttt gtt ttg gtg aat aaa caa ggg aaa aga cat ttc gtt aag       829
Asn Thr Phe Val Leu Val Asn Lys Gln Gly Lys Arg His Phe Val Lys
240                 245                 250                 255 ttt cac tgg atg ccg gaa ctt ggg gtt cat tcg ctg gtc ccc gat gaa       877
Phe His Trp Met Pro Glu Leu Gly Val His Ser Leu Val Pro Asp Glu
                260                 265                 270 tca ttc aaa ctt ggt ggc cag gac cca gac ttc cac cgt aaa gat cta       925
Ser Phe Lys Leu Gly Gly Gln Asp Pro Asp Phe His Arg Lys Asp Leu
            275                 280                 285 atg gag gca atc gac aat aag gtg tac ccg aaa tgg aag ttt gga att       973
Met Glu Ala Ile Asp Asn Lys Val Tyr Pro Lys Trp Lys Phe Gly Ile
290                 295                 300
```

```
cag gtt ctt cct gaa gaa aaa gag cac gat ttt gat ttt gat ata ctt    1021
Gln Val Leu Pro Glu Glu Lys Glu His Asp Phe Asp Phe Asp Ile Leu
        305                 310                 315 gat cca act aag ata tgg cca gag agc cta ata cct gtt cgg tat att    1069
Asp Pro Thr Lys Ile Trp Pro Glu Ser Leu Ile Pro Val Arg Tyr Ile
320                 325                 330                 335 gga gag atg gag ctc aac cgc aac gtc gat gag ttt ttc cca cag aca    1117
Gly Glu Met Glu Leu Asn Arg Asn Val Asp Glu Phe Phe Pro Gln Thr
                340                 345                 350 gaa cag gtt gcc ttc tgt acc gcc cac att gtt cct gga att gaa ttc    1165
Glu Gln Val Ala Phe Cys Thr Ala His Ile Val Pro Gly Ile Glu Phe
            355                 360                 365 tcc ggc gat cct ctg ctc cag gga cgc aat ttc tcc tat ttt gac act    1213
Ser Gly Asp Pro Leu Leu Gln Gly Arg Asn Phe Ser Tyr Phe Asp Thr
        370                 375                 380 caa att acc cgc ctt ggc gtc aac tgg gag gag ctc ccg atc aat cgt    1261
Gln Ile Thr Arg Leu Gly Val Asn Trp Glu Glu Leu Pro Ile Asn Arg
385                 390                 395 cct gtg tgc cct gtt atg aat cac aac agg gat ggt gca atg cgc cat    1309
Pro Val Cys Pro Val Met Asn His Asn Arg Asp Gly Ala Met Arg His
400                 405                 410                 415 aag ata acc caa gga acc gta aac tat tgg ccg aac cgt ttc gag gct    1357
Lys Ile Thr Gln Gly Thr Val Asn Tyr Trp Pro Asn Arg Phe Glu Ala
                420                 425                 430 tgc cca ccc acg aag ccc gag gat ggg ggt ttt gtc act tac cct caa    1405
Cys Pro Pro Thr Lys Pro Glu Asp Gly Gly Phe Val Thr Tyr Pro Gln
            435                 440                 445 aag gta gag cag agt atc aaa gcg agg atg ctt agt agc aag ttc cgc    1453
Lys Val Glu Gln Ser Ile Lys Ala Arg Met Leu Ser Ser Lys Phe Arg
        450                 455                 460 gag cat atc aac caa gcg caa tta ttc tat aac tct ctc tcc gaa tac    1501
Glu His Ile Asn Gln Ala Gln Leu Phe Tyr Asn Ser Leu Ser Glu Tyr
465                 470                 475 gaa aag ctc cat gtc aat aat gct ttt tgc ttt gag ttg gat cac tgc    1549
Glu Lys Leu His Val Asn Asn Ala Phe Cys Phe Glu Leu Asp His Cys
480                 485                 490                 495 gat gac ccc att gtc tac aat aga ctt gtg tct cgg att tct gaa atc    1597
Asp Asp Pro Ile Val Tyr Asn Arg Leu Val Ser Arg Ile Ser Glu Ile
                500                 505                 510 gac cat gcc ctc gcc caa gcc gtt gca gtg aaa gtc ggc gca ccg acc    1645
Asp His Ala Leu Ala Gln Ala Val Ala Val Lys Val Gly Ala Pro Thr
            515                 520                 525 cca cca agg cct ggg aga gac aac cca ggt caa aca acc att aac cta    1693
Pro Pro Arg Pro Gly Arg Asp Asn Pro Gly Gln Thr Thr Ile Asn Leu
        530                 535                 540 agc caa aaa tac atc aac gac cgt cag ctg tcc tct ccc aca att aaa    1741
Ser Gln Lys Tyr Ile Asn Asp Arg Gln Leu Ser Ser Pro Thr Ile Lys
545                 550                 555 ggt cgg agg atc gcc ata ttg att ggg gat ggt tac gat tcc gtc gcc    1789
Gly Arg Arg Ile Ala Ile Leu Ile Gly Asp Gly Tyr Asp Ser Val Ala
560                 565                 570                 575 ttt ggc acg gtc ata gcc gcg gtg agc gcc atg ggc gcg cta ccc ttc    1837
Phe Gly Thr Val Ile Ala Ala Val Ser Ala Met Gly Ala Leu Pro Phe
                580                 585                 590 ata atc ggc acg aag cgg caa ccc atc ttt gcc gac gac gaa gac agg    1885
Ile Ile Gly Thr Lys Arg Gln Pro Ile Phe Ala Asp Asp Glu Asp Arg
            595                 600                 605 aat cac tcc aag ggt gtg act cca aac cac aac tat acc agc caa cgc    1933
Asn His Ser Lys Gly Val Thr Pro Asn His Asn Tyr Thr Ser Gln Arg
        610                 615                 620
```

```
tcc act tgt ttc gac gct act ttc atc cct ggt ggc tca cat atc aag        1981
Ser Thr Cys Phe Asp Ala Thr Phe Ile Pro Gly Gly Ser His Ile Lys
    625                 630                 635 gaa ttg agc cag ctg ggc ctt atc cag cac tgg gtt gcc gag cag ttc        2029
Glu Leu Ser Gln Leu Gly Leu Ile Gln His Trp Val Ala Glu Gln Phe
640                 645                 650                 655 gga cac tgc aag gca att ggc gct aca gga gag gcc atc aat cta atc        2077
Gly His Cys Lys Ala Ile Gly Ala Thr Gly Glu Ala Ile Asn Leu Ile
                660                 665                 670 gtg cag gct ctg agc aac ctg cct gat ttg gag gtc gca tcc gcc tcg        2125
Val Gln Ala Leu Ser Asn Leu Pro Asp Leu Glu Val Ala Ser Ala Ser
            675                 680                 685 tca ggg cat cca gtc gat tgg tac ggc gtt gtc acg tcg agt aag ctg        2173
Ser Gly His Pro Val Asp Trp Tyr Gly Val Val Thr Ser Ser Lys Leu
        690                 695                 700 cat gag ccc cat agt ttg acc gaa ggg atc aag ctg ttt ccc gag gcg        2221
His Glu Pro His Ser Leu Thr Glu Gly Ile Lys Leu Phe Pro Glu Ala
    705                 710                 715 agt gac ttc ttg ggc aag ctc ttt tat cag atc tcc cag cat cgg aat        2269
Ser Asp Phe Leu Gly Lys Leu Phe Tyr Gln Ile Ser Gln His Arg Asn
720                 725                 730                 735 tat gag cgg gag atg gct ggg ttg acg gac aag gtt cca ttt                2311
Tyr Glu Arg Glu Met Ala Gly Leu Thr Asp Lys Val Pro Phe
                740                 745 taaatggcaa catggcatcg gtgtgagtcg ctaggaagca agtgaaagtt aatagtcagg      2371
ccccaaaaac aactatacat actgtaaaca ctaggtttaa ttttggctt atatgttctt       2431 ctggcaacaa tgaattggtt tgttgctgtt gccatttcta acaagttgtc acaactaata      2491
tatatccaat cgaatccatg aaaatggcat tcttgttcac atattc                     2537

<210> SEQ ID NO 2
<211> LENGTH: 749
<212> TYPE: PRT
<213> ORGANISM: Histoplasma capsulatum CATA

<400> SEQUENCE: 2

Met Thr Ser Lys Val Glu Glu Gly Leu Gln Arg Val Lys Glu Leu Val
1               5                   10                  15

Glu Asn Met Gln Pro Gly Glu Gln Lys Val Ala Asp Leu Ala Arg Asp
            20                  25                  30

Thr Thr Asp Val Asn Gly Cys Leu Pro Phe Thr Thr Asp His Gly Val
        35                  40                  45

Lys Val Ser Asn Thr Asp Phe Trp Leu Arg Leu Ala Ser Glu Asn Gln
    50                  55                  60

Thr Gly Pro Leu Leu Leu Glu Asp Gln Ile Ala Arg Glu Lys Ile His
65                  70                  75                  80

Arg Phe Asp His Glu Arg Ile Pro Glu Arg Val Val His Ala Arg Gly
                85                  90                  95

Thr Gly Ala Phe Gly His Phe Lys Leu Phe Glu Ser Ala Ala Asp Val
            100                 105                 110

Thr Ser Ala Gly Val Leu Thr Asp Thr Ser Arg Thr Pro Val Phe
        115                 120                 125

Val Arg Phe Ser Thr Val Gln Gly Ser Lys Gly Ser Phe Asp Thr Val
    130                 135                 140

Arg Asp Val Arg Gly Phe Ala Thr Lys Phe Tyr Thr Glu Glu Gly Asn
145                 150                 155                 160
```

-continued

Trp Asp Leu Val Gly Asn Asn Ile Pro Val Phe Phe Ile Gln Asp Ala
            165                 170                 175

Val Lys Phe Pro Asp Phe Val His Ala Val Lys Pro Glu Pro His Asn
            180                 185                 190

Glu Val Pro Gln Gly Gln Thr Ala His Asn Asn Phe Trp Asp Phe Val
            195                 200                 205

Tyr Met His Pro Glu Ala Thr His Met Phe Met Trp Ala Met Ser Asp
    210                 215                 220

Arg Ala Ile Pro Arg Ser Tyr Arg Met Met Gln Gly Phe Gly Val Asn
225                 230                 235                 240

Thr Phe Val Leu Val Asn Lys Gln Gly Lys Arg His Phe Val Lys Phe
                245                 250                 255

His Trp Met Pro Glu Leu Gly Val His Ser Leu Val Pro Asp Glu Ser
            260                 265                 270

Phe Lys Leu Gly Gly Gln Asp Pro Asp Phe His Arg Lys Asp Leu Met
        275                 280                 285

Glu Ala Ile Asp Asn Lys Val Tyr Pro Lys Trp Lys Phe Gly Ile Gln
        290                 295                 300

Val Leu Pro Glu Glu Lys Glu His Asp Phe Asp Phe Asp Ile Leu Asp
305                 310                 315                 320

Pro Thr Lys Ile Trp Pro Glu Ser Leu Ile Pro Val Arg Tyr Ile Gly
                325                 330                 335

Glu Met Glu Leu Asn Arg Asn Val Asp Glu Phe Phe Pro Gln Thr Glu
            340                 345                 350

Gln Val Ala Phe Cys Thr Ala His Ile Val Pro Gly Ile Glu Phe Ser
        355                 360                 365

Gly Asp Pro Leu Leu Gln Gly Arg Asn Phe Ser Tyr Phe Asp Thr Gln
        370                 375                 380

Ile Thr Arg Leu Gly Val Asn Trp Glu Glu Leu Pro Ile Asn Arg Pro
385                 390                 395                 400

Val Cys Pro Val Met Asn His Asn Arg Asp Gly Ala Met Arg His Lys
                405                 410                 415

Ile Thr Gln Gly Thr Val Asn Tyr Trp Pro Asn Arg Phe Glu Ala Cys
            420                 425                 430

Pro Pro Thr Lys Pro Glu Asp Gly Gly Phe Val Thr Tyr Pro Gln Lys
        435                 440                 445

Val Glu Gln Ser Ile Lys Ala Arg Met Leu Ser Lys Phe Arg Glu
        450                 455                 460

His Ile Asn Gln Ala Gln Leu Phe Tyr Asn Ser Leu Ser Glu Tyr Glu
465                 470                 475                 480

Lys Leu His Val Asn Asn Ala Phe Cys Phe Glu Leu Asp His Cys Asp
                485                 490                 495

Asp Pro Ile Val Tyr Asn Arg Leu Val Ser Arg Ile Ser Glu Ile Asp
            500                 505                 510

His Ala Leu Ala Gln Ala Val Ala Val Lys Val Gly Ala Pro Thr Pro
        515                 520                 525

Pro Arg Pro Gly Arg Asp Asn Pro Gly Gln Thr Thr Ile Asn Leu Ser
        530                 535                 540

Gln Lys Tyr Ile Asn Asp Arg Gln Leu Ser Ser Pro Thr Ile Lys Gly
545                 550                 555                 560

Arg Arg Ile Ala Ile Leu Ile Gly Asp Gly Tyr Asp Ser Val Ala Phe
                565                 570                 575

-continued

```
Gly Thr Val Ile Ala Ala Val Ser Ala Met Gly Ala Leu Pro Phe Ile
            580                 585                 590

Ile Gly Thr Lys Arg Gln Pro Ile Phe Ala Asp Asp Glu Asp Arg Asn
        595                 600                 605

His Ser Lys Gly Val Thr Pro Asn His Asn Tyr Thr Ser Gln Arg Ser
    610                 615                 620

Thr Cys Phe Asp Ala Thr Phe Ile Pro Gly Gly Ser His Ile Lys Glu
625                 630                 635                 640

Leu Ser Gln Leu Gly Leu Ile Gln His Trp Val Ala Glu Gln Phe Gly
                645                 650                 655

His Cys Lys Ala Ile Gly Ala Thr Gly Glu Ala Ile Asn Leu Ile Val
            660                 665                 670

Gln Ala Leu Ser Asn Leu Pro Asp Leu Glu Val Ala Ser Ala Ser Ser
        675                 680                 685

Gly His Pro Val Asp Trp Tyr Gly Val Val Thr Ser Ser Lys Leu His
    690                 695                 700

Glu Pro His Ser Leu Thr Glu Gly Ile Lys Leu Phe Pro Glu Ala Ser
705                 710                 715                 720

Asp Phe Leu Gly Lys Leu Phe Tyr Gln Ile Ser Gln His Arg Asn Tyr
                725                 730                 735

Glu Arg Glu Met Ala Gly Leu Thr Asp Lys Val Pro Phe
            740                 745

<210> SEQ ID NO 3
<211> LENGTH: 4529
<212> TYPE: DNA
<213> ORGANISM: Histoplasma capsulatum CATA
<220> FEATURE:
<221> NAME/KEY: misc_feature
<222> LOCATION: (80)..(80)
<223> OTHER INFORMATION: "n" = any nucleotide
<220> FEATURE:
<221> NAME/KEY: misc_feature
<222> LOCATION: (127)..(127)
<223> OTHER INFORMATION: "n" = any nucleotide

<400> SEQUENCE: 3
gcagtttttt gttgagatta ggggagaaag gcaggccaaa ggacaaactg gggtttaccg     60
ccaaatccct tttgatctcn tgcttttctt ttctctcttt tttttttttt tttttttttt    120
attttanatt ctcgttttct ctcacgggag gattgtttat ttacaatgat tgagagatta    180
tccgcataaa cccctgatgt ttggccatat cttgaaattt ggacactaga ttggaatagg    240
aatagtgcag cctgagattg acatcatttc acttcaacac actttcgaat cccagttttt    300
taccggtttc cagctgttcg acaaagcaac ccggcttcaa gcggaggatg gcaatcgaag    360
aagctactgc tgtcctgtca gacagaaaca cgctgcttcc taggtcagct ttggcattca    420
acagtcagta gttccagggc agctggagtg cttaccatct ggcataccat gcaagactat    480
atctcgatgc cgatggctgg ccactgtacg ctattatatt agctgcttgg agcagagtct    540
ttgcgcctaa gacggagctg gccaaataat tgattcggat ccgagcctgc ctttgaggtg    600
gagagacacc acatataaac agaacatttg cgaatgtcaa tctgacctac ccggccactt    660
tcggggcttt tcatccggat ttgaccccaa tacctcaagt gaattcagac gacgtcaaat    720
tattcaaaca ggcaggtgtt cgctcatcta gagctttcct ctatttattg atacttgtca    780
tggacgagcc aaattaaact cgaaggtaca cgccaagcaa gtccaaaact tttacagaaa    840
aatcagtgac ttacaccact gcttgaatat cgccacaagt taaaacaagt agacgagtcc    900
```

```
agaacacggg tcgacgtcat tctgagttaa cctgcccaga tagaatatga cgtcttttcg    960
ttcgaatggc gtctcaaaat cctcttgctc cctcggaaca ttgaatgagg ttggttctcc   1020
atatcattca caaagttcc agtttcaact ttgaaaaaga accagagaat attttttca    1080
tcgcccccaa tgactagcaa ggttgaagaa gggctccaga gggtcaagga gctggtggaa   1140
aatatgcagc caggagagca aaaggtcgca gacctcgccc gcgatactac agacgtcaac   1200
ggatgcctcc ccttcaccac tgaccatgga gtcaaagtta gcaatacgga cttttggctt   1260
cgacttgcat ccgaaaatca aaccggccca ttgcttttgg aggatcagat tgctcgtgaa   1320
aaggtttcat atacctctcg tctacctccc tattgtgttc catgtcttcc aagctttgcg   1380
ggcaacatat gataaccatc gagttagatc catcgatttg accatgaaag aatcccagaa   1440
cgtgttgtcc atgcacgagg aacaggtgct tttgggcact tcaagctctt cgagagcgcg   1500
gcagacgtga cgtccgctgg tgttctaact gacacgtccc gaactactcc ggtgttcgtt   1560
cggttttcca ccgtccaggg cagcaaaggc agtttcgata cagtccgtga tgtcagaggt   1620
ttcgctacca aattctatac ggaagaaggc aactgggatc ttgttggcaa taacattcct   1680
gtattcttca ttcaagatgc tgtgaaattc ccagattttg gtaagtattg attgatatcc   1740
catttcttca ttatggatat tttcgtgttg atcgttttac aactcgacat tagttcatgc   1800
tgtgaagccg aacctcata cgaagttcc ccagggacaa acagcacata caacttctg     1860
ggactttgta tatatgcatc ctgaggcgac gcatatgttc atgtgggcta tgtcggacag   1920
ggctattccg cgatcatatc ggatgatgca aggatttggt gttaatactt ttgttttggt   1980
gaataaacaa gggaaaagac atttcgttaa gtttcactgg atgccggaac ttggggttca   2040
ttcgctggtc cccgatgaat cattcaaact tggtggccag gacccagact tccaccgtaa   2100
agatctaatg gaggcaatcg acaataaggt gtacccgaaa tggaagtttg gaattcaggt   2160
tcttcctgaa gaaaaagagc acgatttga ttttgatata cttgatccaa ctaagatatg    2220
gccagagagc ctaatacctg ttcggtatat tggagagatg gagctcaacc gcaacgtcga   2280
tgagttttc ccacagacag aacaggttgc cttctgtacc gcccacattg ttcctggaat    2340
tgaattctcc ggcgatcctc tgctccaggg acgcaatttc tcctattttg acactcaaat   2400
tacccgcctt ggcgtcaact gggaggagct cccgatcaat cgtcctgtgt gccctgttat   2460
gaatcacaac agggatggtg caatgcgcca taagataacc caaggaaccg taaactattg   2520
gccgaaccgt ttcgaggctt gcccacccac gaagcccgag gatgggggtt ttgtcactta   2580
ccctcaaaag gtagagcaga gtatcaaagc gaggatgctt agtagcaagt tccgcgagca   2640
tatcaaccaa gcgcaattat tctataactc tctctccgaa tacgaaaagc tccatgtcaa   2700
taatgctttt tgctttgagt tggatcactg cgatgacccc attgtctaca atagacttgt   2760
gtctcggatt tctgaaatcg accatgccct cgcccaagcc gttgcagtga agtcggcgc    2820
accgacccca ccaaggcctg ggagagacaa cccaggtcaa acaaccatta acctaagcca   2880
aaaatacatc aacgaccgtc agctgtcctc tcccacaatt aaaggtcgga ggatcgccat   2940
attgattggg gatggttacg attccgtcgc ctttggcacg gtcatagccg cggtgagcgc   3000
catgggcgcg ctaccttca taatcggcac gaagcggcaa cccatctttg ccgacgacga   3060
agacaggaat cactccaagg gtgtgactcc aaaccacaac tataccagcc aacgctccac   3120
ttgtttcgac gctactttca tccctggtgg ctcacatatc aaggaattga gccagctggg   3180
ccttatccag cactgggttg ccgagcagtt cggacactgc aaggcaattg gcgctacagg   3240
```

```
agaggccatc aatctaatcg tgcaggctct gagcaacctg cctgatttgg aggtcgcatc    3300
cgcctcgtca gggcatccag tcgattggta cggcgttgtc acgtcgagta agctgcatga    3360
gccccatagt ttgaccgaag ggatcaagct gtttcccgag gcgagtgact tcttgggcaa    3420
gctcttttat cagatctccc agcatcggaa ttatgagcgg gagatggctg ggttgacgga    3480
caaggttcca ttttaaatgg caacatggca tcggtgtgag tcgctaggaa gcaagtgaaa    3540
gttaatagtc aggccccaaa acaactata catactgtaa acactaggtt taattttgg     3600 cttatatgtt cttctggcaa caatgaattg gtttgttgct gttgccattt ctaacaagtt    3660
gtcacaacta atatatatcc aatcgaatcc atgaaaatgg cattcttgtt cacatattct    3720
attctgtctg atgcagattt gaattgctag tggttgaaca aaattattga attctaagct    3780
gtgggaagcc tagtcacctt tatttgccga ttcatggtga tcaacaatgt tgtacgttat    3840
gtacgattcc atcctcataa ctatgtgagg gtttagttac tactcctaac tcctggctga    3900 ggggaacta attgaatttg aagaaaacgt cgaacggata tagaacttga taaaaccaaa     3960
aattttcaga tcatgatact gacgaatggg tacgctttca ggaataccta gatggatccc    4020
taccaaaaaa aaaaaataaa taaataaata aaaataaaaa taaaaataaa atacgaggcg    4080
tagtataaaa atgggagggt agtattgaaa aaggacaacc atccgtcgct ggaagctata    4140
gaggcatagg aaggtgacac atgagaaaag tgtttcccta atcaggccat ggaaaaatag    4200
attttgatct ctcaacgaat gaagaaagaa aaatagttga atacaaagcc agtgttgtag    4260
atatatatgc aacataaagg gaattgaacg tcatagacaa gaaaaggaaa cccagaattc    4320
gtgggtcgta cataatacgg ttaaacaaat gtcaaaagaa ggggaaattg aaaattgaaa    4380
agaaagagtg agaagcctaa cgctatcccc atgttctttt ccccgtcctt tcctcacgcc    4440
catctccaca taggtctcca cacatccttc tccttctcac caccagtctc catagtctta    4500
ctcctacaca tacaagtccc aatgacgcc                                      4529

<210> SEQ ID NO 4
<211> LENGTH: 2014
<212> TYPE: DNA
<213> ORGANISM: Histoplasma capsulatum CATP
<220> FEATURE:
<221> NAME/KEY: CDS
<222> LOCATION: (127)..(1635)
<223> OTHER INFORMATION:

<400> SEQUENCE: 4
ctcgagtgtc atcttacctc cccgcccttc ccactgctaa ggggcaacaa cccaccgttg     60
tgactactag gtcgatctac tttcttggtg ccatctccca gccagccaga ctctcaaatc    120 gccatc atg ggt gcc gat gat acc ttc aac tcg tac cga tac aag gat      168
       Met Gly Ala Asp Asp Thr Phe Asn Ser Tyr Arg Tyr Lys Asp
       1               5                   10 act cca act tac act gac tcc aat ggc tgt ccg gtt atg gac ccc gag    216
Thr Pro Thr Tyr Thr Asp Ser Asn Gly Cys Pro Val Met Asp Pro Glu
15                  20                  25                  30 tcc tcc cag cgc gtt gga gaa aat gga ccc ctg ctc ctt cag gat ttc    264
Ser Ser Gln Arg Val Gly Glu Asn Gly Pro Leu Leu Leu Gln Asp Phe
                35                  40                  45 cat ctg atc gat ctc ctc gcg cat ttt gac cgc gag cgg atc cct gaa    312
His Leu Ile Asp Leu Leu Ala His Phe Asp Arg Glu Arg Ile Pro Glu
            50                  55                  60 aga gtc gtc cat gca aag ggt gca gga gcg tac ggt gaa ttc gaa gtg    360
Arg Val Val His Ala Lys Gly Ala Gly Ala Tyr Gly Glu Phe Glu Val
65                  70                  75
```

```
ctg gac gac atc agc gat atc acc acc att aac atg ctg aag ggc gtg        408
Leu Asp Asp Ile Ser Asp Ile Thr Thr Ile Asn Met Leu Lys Gly Val
    80              85                  90 gga aaa aag aca aag ctt gtt acc cgt ttc tcc act gtt ggt ggg gag        456
Gly Lys Lys Thr Lys Leu Val Thr Arg Phe Ser Thr Val Gly Gly Glu
95              100                 105                 110 aag gga tcc gcc gac agc gct cgt gac ccg agg ggt ttc tct acc aaa        504
Lys Gly Ser Ala Asp Ser Ala Arg Asp Pro Arg Gly Phe Ser Thr Lys
                115                 120                 125 ttc tac act gag gag ggc aac tgg gac tgg gtc ttc aac aac acg cca        552
Phe Tyr Thr Glu Glu Gly Asn Trp Asp Trp Val Phe Asn Asn Thr Pro
        130                 135                 140 gtc ttc ttc ttg cgt gat ccc tca aag ttc ccg ctc ttc atc cat acc        600
Val Phe Phe Leu Arg Asp Pro Ser Lys Phe Pro Leu Phe Ile His Thr
            145                 150                 155 cag aag agg aac ccc cag acc aac ctc aag gat gcc acc atg ttt tgg        648
Gln Lys Arg Asn Pro Gln Thr Asn Leu Lys Asp Ala Thr Met Phe Trp
160                 165                 170 gac tat ctg tcc acc cat cag gaa gca atc cac caa gtt atg cat ctc        696
Asp Tyr Leu Ser Thr His Gln Glu Ala Ile His Gln Val Met His Leu
175             180                 185                 190 ttc agt gat cgt ggt acc ccg tac tct tac cgc cac atg aat ggc tac        744
Phe Ser Asp Arg Gly Thr Pro Tyr Ser Tyr Arg His Met Asn Gly Tyr
                195                 200                 205 tcc gga cac act ttc aag tgg ctc acg ccg gac ggg ggt ttc aac tac        792
Ser Gly His Thr Phe Lys Trp Leu Thr Pro Asp Gly Gly Phe Asn Tyr
        210                 215                 220 gtt cag atc cat ctc aag act gac caa ggc agc aag act ttg acc aac        840
Val Gln Ile His Leu Lys Thr Asp Gln Gly Ser Lys Thr Leu Thr Asn
            225                 230                 235 gag gag gcc act aaa ctt gcc gct gag aat cca gat tgg cac acc gag        888
Glu Glu Ala Thr Lys Leu Ala Ala Glu Asn Pro Asp Trp His Thr Glu
240                 245                 250 gac ctc ttc cgg gcc att gag cgc ggc gaa tat cca tcc tgg acc tgt        936
Asp Leu Phe Arg Ala Ile Glu Arg Gly Glu Tyr Pro Ser Trp Thr Cys
255                 260                 265                 270 tac gtc cag gtc ctc agt cct caa cag gcc gag aaa ttc cgc tgg aac        984
Tyr Val Gln Val Leu Ser Pro Gln Gln Ala Glu Lys Phe Arg Trp Asn
            275                 280                 285 att ttc gat ttg acc aag gtc tgg ccc cat tcg gag gtc cct ctc cgc       1032
Ile Phe Asp Leu Thr Lys Val Trp Pro His Ser Glu Val Pro Leu Arg
                290                 295                 300 cgc ttc ggt cgc ctt gtt ctg aac aag aac cca caa aac tac ttc gct       1080
Arg Phe Gly Arg Leu Val Leu Asn Lys Asn Pro Gln Asn Tyr Phe Ala
        305                 310                 315 gag atg gaa caa gct gcc ttc tcg ccc tca cac ctg gtc ccc ggc gtc       1128
Glu Met Glu Gln Ala Ala Phe Ser Pro Ser His Leu Val Pro Gly Val
320                 325                 330 gag ccc tcc gca gac cca gtc ctg caa tcc cgc ctc ttc tcc tac cca       1176
Glu Pro Ser Ala Asp Pro Val Leu Gln Ser Arg Leu Phe Ser Tyr Pro
335                 340                 345                 350 gac acc cat cgc cac cgc ctt ggc gtc aac tac cag cag atc ccc gtc       1224
Asp Thr His Arg His Arg Leu Gly Val Asn Tyr Gln Gln Ile Pro Val
            355                 360                 365 aac tgc ccg ctg cgc gcc ttt aac ccg tac cag cgc gac ggt gcg atg       1272
Asn Cys Pro Leu Arg Ala Phe Asn Pro Tyr Gln Arg Asp Gly Ala Met
                370                 375                 380
```

-continued

```
gcc gtc aac ggc aac tac ggc gcc aac ccc aac tac cca tcc acc ttc     1320
Ala Val Asn Gly Asn Tyr Gly Ala Asn Pro Asn Tyr Pro Ser Thr Phe
        385                 390                 395 cgc cgg atg aat tac atg ccc gtc aaa gcc agc cag gag cac gag aag     1368
Arg Arg Met Asn Tyr Met Pro Val Lys Ala Ser Gln Glu His Glu Lys
    400                 405                 410 tgg acc ggt gct gtc ctc gcg aaa cag ctc ccc gtc acc gat gag gat     1416
Trp Thr Gly Ala Val Leu Ala Lys Gln Leu Pro Val Thr Asp Glu Asp
415                 420                 425                 430 ttc gtg caa gcc aat ggc ctc tgg cag gtt ctg ggt cgc caa cct ggc     1464
Phe Val Gln Ala Asn Gly Leu Trp Gln Val Leu Gly Arg Gln Pro Gly
                435                 440                 445 cag caa gcg aac ttt gtc aag aat gtg gcc ggc cac ttg tgc aat gct     1512
Gln Gln Ala Asn Phe Val Lys Asn Val Ala Gly His Leu Cys Asn Ala
            450                 455                 460 gag cag aaa gtg cgc aag gcg gcg tat ggc atg ttc atc cgc gtc aat     1560
Glu Gln Lys Val Arg Lys Ala Ala Tyr Gly Met Phe Ile Arg Val Asn
        465                 470                 475 aag gac ttg gga agt tcc att gag tcg tca aca gaa gct ttg gtg gcg     1608
Lys Asp Leu Gly Ser Ser Ile Glu Ser Ser Thr Glu Ala Leu Val Ala
    480                 485                 490 tcg cag gcg cag tcg cag ccg cgc ctg tagccgcgtt gagaacgttt           1655
Ser Gln Ala Gln Ser Gln Pro Arg Leu
495                 500 tatgtcgttc ggttggatat tggggttgac aagtttgaat attgaacgtc ggttatgatg   1715
gttgaattga cttttatgtt attttttca tttttaccct tttattttcc ttttattttc    1775
ttttcaccat tctaggtact tggcaggata tgaatgaatt taaacatcct tggataacga   1835
cataagagga taggccgcaa gactagttat gcaggacaac tctggtgttt tctttcgggg   1895
ccctagatat tcactatagt tttggtactt atatcagaac atacttggag gatccgtggc   1955
tatcgtgacc cattttccat tccagggcca aaattttcca aacaaattat ttttctatt    2014

<210> SEQ ID NO 5
<211> LENGTH: 503
<212> TYPE: PRT
<213> ORGANISM: Histoplasma capsulatum CATP

<400> SEQUENCE: 5

Met Gly Ala Asp Asp Thr Phe Asn Ser Tyr Arg Tyr Lys Asp Thr Pro
1               5                   10                  15

Thr Tyr Thr Asp Ser Asn Gly Cys Pro Val Met Asp Pro Glu Ser Ser
            20                  25                  30

Gln Arg Val Gly Glu Asn Gly Pro Leu Leu Leu Gln Asp Phe His Leu
        35                  40                  45

Ile Asp Leu Leu Ala His Phe Asp Arg Glu Arg Ile Pro Glu Arg Val
    50                  55                  60

Val His Ala Lys Gly Ala Gly Ala Tyr Gly Glu Phe Glu Val Leu Asp
65                  70                  75                  80

Asp Ile Ser Asp Ile Thr Thr Ile Asn Met Leu Lys Gly Val Gly Lys
                85                  90                  95

Lys Thr Lys Leu Val Thr Arg Phe Ser Thr Val Gly Gly Glu Lys Gly
            100                 105                 110

Ser Ala Asp Ser Ala Arg Asp Pro Arg Gly Phe Ser Thr Lys Phe Tyr
        115                 120                 125

Thr Glu Glu Gly Asn Trp Asp Trp Val Phe Asn Asn Thr Pro Val Phe
    130                 135                 140
```

```
Phe Leu Arg Asp Pro Ser Lys Phe Pro Leu Phe Ile His Thr Gln Lys
145                 150                 155                 160

Arg Asn Pro Gln Thr Asn Leu Lys Asp Ala Thr Met Phe Trp Asp Tyr
                165                 170                 175

Leu Ser Thr His Gln Glu Ala Ile His Gln Val Met His Leu Phe Ser
            180                 185                 190

Asp Arg Gly Thr Pro Tyr Ser Tyr Arg His Met Asn Gly Tyr Ser Gly
        195                 200                 205

His Thr Phe Lys Trp Leu Thr Pro Asp Gly Gly Phe Asn Tyr Val Gln
210                 215                 220

Ile His Leu Lys Thr Asp Gln Gly Ser Lys Thr Leu Thr Asn Glu Glu
225                 230                 235                 240

Ala Thr Lys Leu Ala Ala Glu Asn Pro Asp Trp His Thr Glu Asp Leu
                245                 250                 255

Phe Arg Ala Ile Glu Arg Gly Glu Tyr Pro Ser Trp Thr Cys Tyr Val
            260                 265                 270

Gln Val Leu Ser Pro Gln Gln Ala Glu Lys Phe Arg Trp Asn Ile Phe
        275                 280                 285

Asp Leu Thr Lys Val Trp Pro His Ser Glu Val Pro Leu Arg Arg Phe
290                 295                 300

Gly Arg Leu Val Leu Asn Lys Asn Pro Gln Asn Tyr Phe Ala Glu Met
305                 310                 315                 320

Glu Gln Ala Ala Phe Ser Pro Ser His Leu Val Pro Gly Val Glu Pro
                325                 330                 335

Ser Ala Asp Pro Val Leu Gln Ser Arg Leu Phe Ser Tyr Pro Asp Thr
            340                 345                 350

His Arg His Arg Leu Gly Val Asn Tyr Gln Gln Ile Pro Val Asn Cys
        355                 360                 365

Pro Leu Arg Ala Phe Asn Pro Tyr Gln Arg Asp Gly Ala Met Ala Val
370                 375                 380

Asn Gly Asn Tyr Gly Ala Asn Pro Asn Tyr Pro Ser Thr Phe Arg Arg
385                 390                 395                 400

Met Asn Tyr Met Pro Val Lys Ala Ser Gln Glu His Glu Lys Trp Thr
                405                 410                 415

Gly Ala Val Leu Ala Lys Gln Leu Pro Val Thr Asp Glu Asp Phe Val
            420                 425                 430

Gln Ala Asn Gly Leu Trp Gln Val Leu Gly Arg Gln Pro Gly Gln Gln
        435                 440                 445

Ala Asn Phe Val Lys Asn Val Ala Gly His Leu Cys Asn Ala Glu Gln
450                 455                 460

Lys Val Arg Lys Ala Ala Tyr Gly Met Phe Ile Arg Val Asn Lys Asp
465                 470                 475                 480

Leu Gly Ser Ser Ile Glu Ser Ser Thr Glu Ala Leu Val Ala Ser Gln
                485                 490                 495

Ala Gln Ser Gln Pro Arg Leu
            500
```

<210> SEQ ID NO 6
<211> LENGTH: 3883
<212> TYPE: DNA
<213> ORGANISM: Histoplasma capsulatum CATP
<220> FEATURE:
<221> NAME/KEY: misc_feature
<222> LOCATION: (210)..(210)
<223> OTHER INFORMATION: “n” = any nucleotide

<400> SEQUENCE: 6

| | | | | | |
|---|---|---|---|---|---|
| cgtgcttaga | cacaatatag | ctagagagat | aaagaattct | aatatggtaa | ttctgctaga | 60 |
| atgtactgta | tttgtatgag | gaacttttca | caagtgtaaa | actatttaat | cttttcaaga | 120 |
| aatatgatgg | caaataaaat | aaaaataagg | gacttcaaga | actaactcta | tagtgagata | 180 |
| aatagattag | ctagtgttgc | aaaatccatn | tagcagatgc | atgccgcgta | tggcataccc | 240 |
| tctgttggca | aggagtgccc | cagacctaga | attccatggt | tgggcaagtc | atgtttcttc | 300 |
| ctgcaaccaa | gataaggcag | gccacctaaa | ttctaatcaa | agcctctgag | ttctcacact | 360 |
| tttgagtacc | atttatatag | aagaagccat | tgaatctata | gaatatgtag | actgatagca | 420 |
| agccgatcct | gctggcgcta | agaggaaata | tttccttggc | agctcagtgg | aggaagtttg | 480 |
| gcggttctat | atagacgtat | cttccctcgt | ttgcaggaaa | gcagagctag | attggtattg | 540 |
| aggaccttga | ggtggtattc | cattctattt | ttatgtctaa | attctttaaa | tgtggcaaac | 600 |
| gagctgcacc | ccggcggtgc | gcgtaaagct | cgaaacatgc | acagacagcg | cacagagaca | 660 |
| gcgcacagag | acagagcaca | gagacagagc | atagagacag | gcggcagtcc | tccctcgcaa | 720 |
| atatcgctgt | agtcggtttg | gtggctaagc | ttgaagcagt | tgggggctta | gaaagccctg | 780 |
| acagttcaac | ggccaaaggg | aggaaacaga | gagttacttc | gtttgtctac | cgaattacaa | 840 |
| ggcaacttaa | gtaccagtac | atcgatgagc | ggccccacgc | ggctcatcct | cggggacgat | 900 |
| tccatggcgg | ggtctcggcg | atatatatag | acacccccttt | ccctctttta | gtgcgacccc | 960 |
| gtcattgttc | ctcccataaa | cctcttctgc | ttccaagtct | cgagtgtcat | cttacctccc | 1020 |
| cgcccttccc | actgctaagg | ggcaacaacc | caccgttgtg | actactaggt | cgatctactt | 1080 |
| tcttggtgcc | atctcccagc | cagccagact | ctcaaatcgc | catcatgggt | gccgatgata | 1140 |
| ccttcagtat | gtgctcacca | ttcccagcac | ggtccactag | ttccgagctt | cgatacttaa | 1200 |
| tctagatata | tacatggacg | gacgtgtcta | aaacgcgggc | aacgacatcg | aagacagggg | 1260 |
| ctaaccaata | tcctgccata | tagactcgta | ccgatacaag | gatactccaa | cttacactga | 1320 |
| ctccaatggc | tgtccggtag | gtttcgcgtc | tgctcttaat | aatttgtcgt | attgtcccca | 1380 |
| ctagatcggc | tatcattaga | gaacagatca | gcgagagata | cactaattag | aaacgttgga | 1440 |
| tcccgtctaa | tgctgatggt | acggttatat | aggttatgga | ccccgagtcc | tcccagcgcg | 1500 |
| ttggagaaaa | tggaccccctg | ctccttcagg | atttccatct | gatcgatctc | ctcgcgcatt | 1560 |
| ttgaccgcga | gcggatccct | gaaagagtcg | tccatgcaaa | gggtgcagga | gcgtacggtg | 1620 |
| aattcgaagt | gctggacgac | atcagcgata | tcgtaagtca | aagactcttc | ttgtccttt | 1680 |
| tgtttgcaac | catcagctgc | ggcactgcag | acatacccag | aaccctgttc | tatgctaacg | 1740 |
| attactatag | accaccatta | acatgctgaa | gggcgtggga | aaaagacaa | agcttgttac | 1800 |
| ccgtttctcc | actgttggtg | gggagaaggg | atccgccgac | agcgctcgtg | acccgagggg | 1860 |
| tttctctacc | aaattctaca | ctgaggaggg | caactgggac | tgggtcttca | acaacacgcc | 1920 |
| agtcttcttc | ttgcgtgatc | cctcaaagtt | cccgctcttc | atccataccc | agaagaggaa | 1980 |
| cccccagacc | aacctcaagg | atgccaccat | gttttgggac | tatctgtcca | cccatcagga | 2040 |
| agcaatccac | caagttatgc | atctcttcag | tgatcgtggt | accccgtact | cttaccgcca | 2100 |
| catgaatggc | tactccggac | acactttcaa | gtggctcacg | ccggacgggg | gtttcaacta | 2160 |
| cgttcagatc | catctcaaga | ctgaccaagg | cagcaagact | tgaccaacg | aggaggccac | 2220 |
| taaacttgcc | gctgagaatc | cagattggca | caccgaggac | ctcttccggg | ccattgagcg | 2280 |

-continued

```
cggcgaatat ccatcctgga cctgttacgt ccaggtcctc agtcctcaac aggccgagaa    2340
attccgctgg aacattttcg atttgaccaa ggtctggccc cattcggagg tccctctccg    2400
ccgcttcggt cgccttgttc tgaacaagaa cccacaaaac tacttcgctg agatggaaca    2460
agctgccttc tcgccctcac acctggtccc cggcgtcgag ccctccgcag acccagtcct    2520
gcaatcccgc tcttctcct acccagacac ccatcgccac cgccttggcg tcaactacca    2580
gcagatcccc gtcaactgcc cgctgcgcgc ctttaacccg taccagcgcg acggtgcgat    2640
ggccgtcaac ggcaactacg cgccaaccc caactaccca tccaccttcc gccggatgaa    2700
ttacatgccc gtcaaagcca gccaggagca cgagaagtgg accggtgctg tcctcgcgaa    2760
acagctcccc gtcaccgatg aggatttcgt gcaagccaat ggcctctggc aggttctggg    2820
tcgccaacct ggccagcaag cgaactttgt caagaatgtg gccggccact tgtgcaatgc    2880
tgagcagaaa gtgcgcaagg cggcgtatgg catgttcatc cgcgtcaata aggacttggg    2940
aagttccatt gagtcgtcaa cagaagcttt ggtggcgtcg caggcgcagt cgcagccgcg    3000
cctgtagccg cgttgagaac gttttatgtc gttcggttgg atattggggt tgacaagttt    3060
gaatattgaa cgtcggttat gatggttgaa ttgactttta tgttattttt ttcattttta    3120
cccttttatt ttccttttat tttcttttca ccattctagg tacttggcag gatatgaatg    3180
aatttaaaca tccttggata acgacataag aggataggcc gcaagactag ttatgcagga    3240
caactctggt gttttctttc ggggccctag atattcacta tagttttggt acttatatca    3300
gaacatactt ggaggatccg tggctatcgt gacccatttt ccattccagg gccaaaattt    3360
tccaaacaaa ttattttct attagttatc ttgtcgggtc atcattctgc ttttgagttg    3420
ggtatctctg aaatataagc tgctgctata attacgtgga actccttttc caatcagtcg    3480
ttgaagtgca ttacggtgta gaaattattt gatgtctcaa ctgagtttcc actttatatc    3540
aattacggat cgcaattgag gcgcatttat ttatacatga caaggactac acgtatatat    3600
atatcgacaa tagaagattt atgcagatat agtaaaattg ttgtggtagt agttatttcc    3660
gtttgagtgg cccatggctg gtttggttgg gttacatcct agcaaggcaa gttttccaca    3720
ccaatccacc tttatttgtg gtcggtcctg taaatatgta gcgcggcatg gaccttactt    3780
agttacaggc aacgaaattt ttctttaacc aagcatccac atgaagtttt agaggcaaat    3840
aactatatgc acattttcct gggctatgtc ctctgtctga gca                     3883
```

<210> SEQ ID NO 7
<211> LENGTH: 84
<212> TYPE: DNA
<213> ORGANISM: histoplasma capsulatum CATA

<400> SEQUENCE: 7

```
gtttcatata cctctcgtct acctccctat tgtgttccat gtcttccaag ctttgcgggc    60
aacatatgat aaccatcgag ttag                                           84
```

<210> SEQ ID NO 8
<211> LENGTH: 73
<212> TYPE: DNA
<213> ORGANISM: histoplasma capsulatum CATA

<400> SEQUENCE: 8

```
gtaagtattg attgatatcc catttcttca ttatggatat tttcgtgttg atcgttttac    60
aactcgacat tag                                                       73
```

<210> SEQ ID NO 9
<211> LENGTH: 137
<212> TYPE: DNA
<213> ORGANISM: histoplasma capsulatum CATP

<400> SEQUENCE: 9
gtatgtgctc accattccca gcacggtcca ctagttccga gcttcgatac ttaatctaga 60
tatatacatg gacggacgtg tctaaaacgc gggcaacgac atcgaagaca ggggctaacc 120
aatatcctgc catatag 137

<210> SEQ ID NO 10
<211> LENGTH: 136
<212> TYPE: DNA
<213> ORGANISM: histoplasma capsulatum CATP

<400> SEQUENCE: 10
gtaggtttcg cgtctgctct taataatttg tcgtattgtc cccactagat cggctatcat 60
tagagaacag atcagcgaga gatacactaa ttagaaacgt tggatcccgt ctaatgctga 120
tggtacggtt atatag 136

<210> SEQ ID NO 11
<211> LENGTH: 98
<212> TYPE: DNA
<213> ORGANISM: histoplasma capsulatum CATP

<400> SEQUENCE: 11
gtaagtcaaa gactcttctt gtcctttttg tttgcaacca tcagctgcgg cactgcagac 60
atacccagaa ccctgttcta tgctaacgat tactatag 98

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
tgcgggcaac atatgataac 20

<210> SEQ ID NO 13
<211> LENGTH: 21
<212> TYPE: DNA
<213> ORGANISM: Artificial Sequence
<220> FEATURE:
<223> OTHER INFORMATION: Synthetic primer

<400> SEQUENCE: 13
gataaccatc gagttagatc c 21

<210> SEQ ID NO 14
<211> LENGTH: 19
<212> TYPE: DNA
<213> ORGANISM: Artificial Sequence
<220> FEATURE:
<223> OTHER INFORMATION: Synthetic primer

<400> SEQUENCE: 14
cgtccgctgg tgttctaac 19

<210> SEQ ID NO 15
<211> LENGTH: 20
<212> TYPE: DNA

<213> ORGANISM: Artificial Sequence
<220> FEATURE:
<223> OTHER INFORMATION: Synthetic primer

<400> SEQUENCE: 15
cgatcaacac gaaaatatcc                                            20

<210> SEQ ID NO 16
<211> LENGTH: 17
<212> TYPE: DNA
<213> ORGANISM: Artificial Sequence
<220> FEATURE:
<223> OTHER INFORMATION: Synthetic primer

<400> SEQUENCE: 16
tatcaatcaa tacttac                                               17

<210> SEQ ID NO 17
<211> LENGTH: 19
<212> TYPE: DNA
<213> ORGANISM: Artificial Sequence
<220> FEATURE:
<223> OTHER INFORMATION: Synthetic primer

<400> SEQUENCE: 17
gacatcacgg actgtatcg                                             19

<210> SEQ ID NO 18
<211> LENGTH: 21
<212> TYPE: DNA
<213> ORGANISM: Artificial Sequence
<220> FEATURE:
<223> OTHER INFORMATION: Synthetic primer

<400> SEQUENCE: 18
gagcttcgat acttaatcta g                                          21

<210> SEQ ID NO 19
<211> LENGTH: 19
<212> TYPE: DNA
<213> ORGANISM: Artificial Sequence
<220> FEATURE:
<223> OTHER INFORMATION: Synthetic primer

<400> SEQUENCE: 19
gacggacgtg tctaaaacg                                             19

<210> SEQ ID NO 20
<211> LENGTH: 21
<212> TYPE: DNA
<213> ORGANISM: Artificial Sequence
<220> FEATURE:
<223> OTHER INFORMATION: Synthetic primer

<400> SEQUENCE: 20
gctatcatta gagaacagat c                                          21

<210> SEQ ID NO 21
<211> LENGTH: 19
<212> TYPE: DNA
<213> ORGANISM: Artificial Sequence
<220> FEATURE:
<223> OTHER INFORMATION: Synthetic primer

<400> SEQUENCE: 21
cagggttctg ggtatgtct                                             19

<210> SEQ ID NO 22
<211> LENGTH: 19
<212> TYPE: DNA
<213> ORGANISM: Artificial Sequence
<220> FEATURE:
<223> OTHER INFORMATION: Synthetic primer

<400> SEQUENCE: 22
gtgccgcagc tgatggttg                                                 19

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
gatctagtgg ggacaatacg                                                20

<210> SEQ ID NO 24
<211> LENGTH: 361
<212> TYPE: DNA
<213> ORGANISM: Histoplasma capsulatum CATA

<400> SEQUENCE: 24
attcacaaaa gctccagttt caactttgaa aaagaaccag agaatatttt tttcatcgcc    60
cccaatgact agcaaggttg aagaagggct ccagagggtc aaggagctgg tggaaaatat   120
gcagccagga gagcaaaagg tcgcagacct cgcccgcgat actacagacg tcaacggatg   180
cctccccttc accactgacc atggagtcaa agttagcaat acggactttt ggcttcgact   240
tgcatccgaa aatcaaaccg gcccattgct tttggaggat cagattgctc gtgaaaagat   300
ccatcgattt gaccatgaaa gaatcccaga acgtgttgtc catgcacgag gaacaggtgc   360
t                                                                  361

<210> SEQ ID NO 25
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (2)..(2)
<223> OTHER INFORMATION: "n" = any nucleotide
<220> FEATURE:
<221> NAME/KEY: misc_feature
<222> LOCATION: (17)..(17)
<223> OTHER INFORMATION: "n" = any nucleotide

<400> SEQUENCE: 25
cnathgayaa yaargcntay c                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (15)..(15)
<223> OTHER INFORMATION: "n" = any nucleotide

```
<400> SEQUENCE: 26
tcrtcrcart grtcnarytc r                                      21

<210> SEQ ID NO 27
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (8)..(8)
<223> OTHER INFORMATION: "n" = any nucleotide
<220> FEATURE:
<221> NAME/KEY: misc_feature
<222> LOCATION: (14)..(14)
<223> OTHER INFORMATION: "n" = any nucleotide

<400> SEQUENCE: 27
cytcraanck rttnggccar t                                      21

<210> SEQ ID NO 28
<211> LENGTH: 21
<212> TYPE: DNA
<213> ORGANISM: Artificial Sequence
<220> FEATURE:
<223> OTHER INFORMATION: Synthetic primer

<400> SEQUENCE: 28
cttgatccaa ctaagatatg g                                      21

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
caacgtcgat gagtttttcc                                        20

<210> SEQ ID NO 30
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (12)..(12)
<223> OTHER INFORMATION: "n" = any nucleotide

<400> SEQUENCE: 30
athcaycarg tnatgcayyt                                        20

<210> SEQ ID NO 31
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: "n" = any nucleotide
<220> FEATURE:
<221> NAME/KEY: misc_feature
<222> LOCATION: (12)..(12)
<223> OTHER INFORMATION: "n" = any nucleotide
```

```
<400> SEQUENCE: 31
tcyttrttna cnckdatraa                                              20

<210> SEQ ID NO 32
<211> LENGTH: 17
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: "n" = any nucleotide
<220> FEATURE:
<221> NAME/KEY: misc_feature
<222> LOCATION: (3)..(3)
<223> OTHER INFORMATION: "n" = any nucleotide

<400> SEQUENCE: 32
aangcngcyt gytccat                                                 17

<210> SEQ ID NO 33
<211> LENGTH: 21
<212> TYPE: DNA
<213> ORGANISM: Artificial Sequence
<220> FEATURE:
<223> OTHER INFORMATION: Synthetic primer

<400> SEQUENCE: 33
attcacaaaa gctccagttt c                                            21

<210> SEQ ID NO 34
<211> LENGTH: 23
<212> TYPE: DNA
<213> ORGANISM: Artificial Sequence
<220> FEATURE:
<223> OTHER INFORMATION: Synthetic primer

<400> SEQUENCE: 34
ggattctttc atggtcaaaa tcg                                          23

<210> SEQ ID NO 35
<211> LENGTH: 18
<212> TYPE: DNA
<213> ORGANISM: Artificial Sequence
<220> FEATURE:
<223> OTHER INFORMATION: Synthetic primer

<400> SEQUENCE: 35
atgggtgccg atgatacc                                                18

<210> SEQ ID NO 36
<211> LENGTH: 19
<212> TYPE: DNA
<213> ORGANISM: Artificial Sequence
<220> FEATURE:
<223> OTHER INFORMATION: Synthetic primer

<400> SEQUENCE: 36
ccgctcgcgg tcaaaatgc                                               19

<210> SEQ ID NO 37
<211> LENGTH: 20
<212> TYPE: DNA
<213> ORGANISM: Artificial Sequence
<220> FEATURE:
```

-continued

<223> OTHER INFORMATION: Synthetic primer

<400> SEQUENCE: 37
gaagtgctgg acgacatcag                                                                       20

<210> SEQ ID NO 38
<211> LENGTH: 19
<212> TYPE: DNA
<213> ORGANISM: Artificial Sequence
<220> FEATURE:
<223> OTHER INFORMATION: Synthetic primer

<400> SEQUENCE: 38
gggaagtcgt acaattacc                                                                         19

<210> SEQ ID NO 39
<211> LENGTH: 749
<212> TYPE: PRT
<213> ORGANISM: Histoplasma capsulatum

<400> SEQUENCE: 39

```
Met Thr Ser Lys Val Glu Glu Gly Leu Gln Arg Val Lys Glu Leu Val
1               5                   10                  15

Glu Asn Met Gln Pro Gly Glu Gln Lys Val Ala Asp Leu Ala Arg Asp
            20                  25                  30

Thr Thr Asp Val Asn Gly Cys Leu Pro Phe Thr Thr Asp His Gly Val
        35                  40                  45

Lys Val Ser Asn Thr Asp Phe Trp Leu Arg Leu Ala Ser Glu Asn Gln
    50                  55                  60

Thr Gly Pro Leu Leu Leu Glu Tyr Gln Ile Ala Arg Glu Lys Ile His
65                  70                  75                  80

Arg Phe Asp His Glu Arg Ile Pro Glu Arg Val Val His Ala Arg Gly
                85                  90                  95

Thr Gly Ala Phe Gly His Phe Lys Leu Phe Glu Ser Ala Ala Asp Val
            100                 105                 110

Thr Ser Ala Gly Val Leu Thr Asp Thr Ser Arg Thr Thr Pro Val Phe
        115                 120                 125

Val Arg Phe Ser Thr Val Gln Gly Ser Lys Gly Ser Phe Asp Thr Val
    130                 135                 140

Arg Asp Val Arg Gly Phe Ala Thr Lys Phe Tyr Thr Glu Glu Gly Asn
145                 150                 155                 160

Trp Asp Leu Val Gly Asn Asn Ile Pro Val Phe Phe Ile Gln Asp Ala
                165                 170                 175

Val Lys Phe Pro Asp Phe Val His Ala Val Lys Pro Glu Pro His Asn
            180                 185                 190

Glu Val Pro Gln Gly Gln Thr Ala His Asn Asn Phe Trp Asp Phe Val
        195                 200                 205

Tyr Met His Pro Glu Ala Thr His Met Phe Met Trp Ala Met Ser Asp
    210                 215                 220

Arg Ala Ile Pro Arg Ser Tyr Arg Met Met Gln Gly Phe Gly Val Asn
225                 230                 235                 240

Thr Phe Val Leu Val Asn Lys Gln Gly Lys Arg His Phe Val Lys Phe
                245                 250                 255

His Trp Met Pro Glu Leu Gly Val His Ser Leu Val Pro Asp Glu Ser
            260                 265                 270

Phe Lys Leu Gly Gly Gln Asp Pro Asp Phe His Arg Lys Asp Leu Met
        275                 280                 285
```

-continued

```
Glu Ala Ile Asp Asn Lys Val Tyr Pro Lys Trp Lys Phe Gly Ile Gln
290                 295                 300

Val Leu Pro Glu Glu Lys Glu His Asp Phe Asp Phe Asp Ile Leu Asp
305                 310                 315                 320

Pro Thr Lys Ile Trp Pro Glu Ser Leu Ile Pro Val Arg Tyr Ile Gly
                325                 330                 335

Glu Met Glu Leu Asn Arg Asn Val Asp Glu Phe Phe Pro Gln Thr Glu
            340                 345                 350

Gln Val Ala Phe Cys Thr Ala His Ile Val Pro Gly Ile Glu Phe Ser
        355                 360                 365

Gly Asp Pro Leu Leu Gln Gly Arg Asn Phe Ser Tyr Phe Asp Thr Gln
370                 375                 380

Ile Thr Arg Leu Gly Val Asn Trp Glu Glu Leu Pro Ile Asn Arg Pro
385                 390                 395                 400

Val Cys Pro Val Met Asn His Asn Arg Asp Gly Ala Met Arg His Lys
                405                 410                 415

Ile Thr Gln Gly Thr Val Asn Tyr Trp Pro Asn Arg Phe Glu Ala Cys
            420                 425                 430

Pro Pro Thr Lys Pro Glu Asp Gly Gly Phe Val Thr Tyr Pro Gln Lys
        435                 440                 445

Val Glu Gln Ser Ile Lys Ala Arg Met Leu Ser Ser Lys Phe Arg Glu
450                 455                 460

His Ile Asn Gln Ala Gln Leu Phe Tyr Asn Ser Leu Ser Glu Tyr Glu
465                 470                 475                 480

Lys Leu His Val Asn Asn Ala Phe Cys Phe Glu Leu Asp His Cys Asp
                485                 490                 495

Asp Pro Ile Val Tyr Asn Arg Leu Val Ser Arg Ile Ser Glu Ile Asp
            500                 505                 510

His Ala Leu Ala Gln Ala Val Ala Val Lys Val Gly Ala Pro Thr Pro
        515                 520                 525

Pro Arg Pro Gly Arg Asp Asn Pro Gly Gln Thr Thr Ile Asn Leu Ser
530                 535                 540

Gln Lys Tyr Ile Asn Asp Arg Gln Leu Ser Ser Pro Thr Ile Lys Gly
545                 550                 555                 560

Arg Arg Ile Ala Ile Leu Ile Gly Asp Gly Tyr Asp Ser Val Ala Phe
                565                 570                 575

Gly Thr Val Ile Ala Ala Val Ser Ala Met Gly Ala Leu Pro Phe Ile
            580                 585                 590

Ile Gly Thr Lys Arg Gln Pro Ile Phe Ala Asp Asp Glu Asp Arg Asn
        595                 600                 605

His Ser Lys Gly Val Thr Pro Asn His Asn Tyr Thr Ser Gln Arg Ser
            610                 615                 620

Thr Cys Phe Asp Ala Thr Phe Ile Pro Gly Gly Ser His Ile Lys Glu
625                 630                 635                 640

Leu Ser Gln Leu Gly Leu Ile Gln His Trp Val Ala Glu Gln Phe Gly
                645                 650                 655

His Cys Lys Ala Ile Gly Ala Thr Gly Glu Ala Ile Asn Leu Ile Val
            660                 665                 670

Gln Ala Leu Ser Asn Leu Pro Asp Leu Glu Val Ala Ser Ala Ser Ser
        675                 680                 685

Gly His Pro Val Asp Trp Tyr Gly Val Val Thr Ser Ser Lys Leu His
690                 695                 700
```

```
Glu Pro His Ser Leu Thr Glu Gly Ile Lys Leu Phe Pro Glu Ala Ser
705                 710                 715                 720

Asp Phe Leu Gly Lys Leu Phe Tyr Gln Ile Ser Gln His Arg Asn Tyr
                725                 730                 735

Glu Arg Glu Met Ala Gly Leu Thr Asp Lys Val Pro Phe
            740                 745
```

<210> SEQ ID NO 40
<211> LENGTH: 749
<212> TYPE: PRT
<213> ORGANISM: Aspergillus fumigatus

<400> SEQUENCE: 40

```
Met Ala Thr Lys Ile Ala Gly Gly Leu His Arg Ala Gln Glu Val Leu
1               5                   10                  15

Gln Asn Thr Ser Ser Lys Ser Lys Lys Leu Val Asp Leu Glu Arg Asp
                20                  25                  30

Thr Ala Asp Ala His Thr Gln Pro Leu Thr Thr Asp His Gly Val
            35                  40                  45

Arg Val Ser Asn Thr Asp Gln Trp Leu Arg Val Thr Asn Asp Arg Arg
50                  55                  60

Thr Gly Pro Ser Leu Leu Glu Asp Gln Ile Ala Arg Glu Lys Ile His
65                  70                  75                  80

Arg Phe Asp His Glu Arg Ile Pro Glu Arg Val Val His Ala Arg Gly
                85                  90                  95

Thr Gly Ala Phe Gly Asn Phe Lys Leu Lys Glu Ser Ile Glu Asp Leu
            100                 105                 110

Thr Tyr Ala Gly Val Leu Thr Asp Thr Ser Arg Asn Thr Pro Val Phe
        115                 120                 125

Val Arg Phe Ser Thr Val Gln Gly Ser Arg Gly Ser Ala Asp Thr Val
130                 135                 140

Arg Asp Val Arg Gly Phe Ala Val Lys Phe Tyr Thr Asp Glu Gly Asn
145                 150                 155                 160

Trp Asp Ile Val Gly Asn Asn Ile Pro Val Phe Phe Ile Gln Asp Ala
                165                 170                 175

Val Lys Phe Pro Asp Phe Val His Ala Val Lys Pro Glu Pro His Asn
            180                 185                 190

Glu Val Pro Gln Ala Gln Thr Ala His Asn Asn Phe Trp Asp Phe Val
        195                 200                 205

Tyr Leu His Pro Glu Ala Thr His Met Phe Met Trp Ala Met Ser Asp
    210                 215                 220

Arg Ala Ile Pro Arg Ser Tyr Arg Met Met Gln Gly Phe Gly Val Asn
225                 230                 235                 240

Thr Phe Ala Leu Val Asn Lys Glu Gly Lys Arg His Phe Val Lys Phe
                245                 250                 255

His Trp Ile Pro His Leu Gly Val His Ser Leu Val Trp Asp Glu Ala
            260                 265                 270

Leu Lys Leu Gly Gly Gln Asp Pro Asp Phe His Arg Lys Asp Leu Met
        275                 280                 285

Glu Ala Ile Asp Asn Lys Ala Tyr Pro Lys Trp Asp Phe Ala Ile Gln
    290                 295                 300

Val Ile Pro Glu Glu Lys Gln Asp Asp Phe Glu Phe Asp Ile Leu Asp
305                 310                 315                 320

Ala Thr Lys Ile Trp Pro Glu Asn Leu Val Pro Leu Arg Val Ile Gly
                325                 330                 335
```

```
Glu Leu Glu Leu Asn Arg Asn Val Asp Glu Phe Phe Pro Gln Thr Glu
            340                 345                 350
Gln Val Ala Phe Cys Thr Ser His Ile Val Pro Gly Ile Asp Phe Thr
            355                 360                 365
Asp Asp Pro Leu Leu Gln Gly Arg Asn Phe Ser Tyr Phe Asp Thr Gln
            370                 375                 380
Ile Ser Arg Leu Gly Ile Asn Trp Glu Leu Pro Ile Asn Arg Pro
385                 390                 395                 400
Val Cys Pro Val Leu Asn His Asn Arg Asp Gly Gln Met Arg His Arg
                405                 410                 415
Ile Thr Gln Gly Thr Val Asn Tyr Trp Pro Asn Arg Phe Glu Ala Val
            420                 425                 430
Pro Pro Thr Gly Thr Lys Gly Ser Gly Val Gly Gly Phe Thr Thr
            435                 440                 445
Tyr Pro Gln Arg Val Glu Gly Ile Lys Asn Arg Ala Leu Asn Asp Lys
            450                 455                 460
Phe Arg Glu His His Asn Gln Ala Gln Leu Phe Tyr Asn Ser Met Ser
465                 470                 475                 480
Glu His Glu Lys Leu His Met Lys Lys Ala Phe Ser Phe Glu Leu Asp
            485                 490                 495
His Cys Asp Asp Pro Thr Val Tyr Glu Arg Leu Ala Gly His Arg Leu
            500                 505                 510
Ala Glu Ile Asp Leu Glu Leu Ala Gln Lys Val Ala Glu Met Val Gly
            515                 520                 525
Ala Pro Ile Pro Ala Lys Ala Leu Lys Gln Asn His Gly Arg Arg Ala
            530                 535                 540
Pro His Leu Ser Gln Thr Glu Phe Ile Pro Lys Asn Pro Thr Ile Ala
545                 550                 555                 560
Ser Arg Arg Ile Ala Ile Ile Gly Asp Gly Tyr Asp Pro Val Ala
            565                 570                 575
Ser Thr Gly Leu Lys Thr Ala Ile Lys Ala Ala Ser Ala Leu Pro Phe
            580                 585                 590
Ile Ile Gly Thr Lys Arg Ser Ala Ile Tyr Ala Thr Glu Asp Lys Thr
            595                 600                 605
Ser Ser Lys Gly Ile Ile Pro Asp His His Tyr Asp Gly Gln Arg Ser
            610                 615                 620
Thr Met Phe Asp Ala Thr Phe Ile Pro Gly Gly Pro His Val Ala Thr
625                 630                 635                 640
Leu Arg Gln Asn Gly Gln Ile Lys Tyr Trp Ile Ser Glu Thr Phe Gly
            645                 650                 655
His Leu Lys Ala Leu Gly Ala Thr Gly Glu Ala Val Asp Leu Val Lys
            660                 665                 670
Glu Thr Leu Ser Gly Thr Leu His Val Gln Val Ala Ser Ser Gln Ser
            675                 680                 685
Pro Glu Pro Val Glu Trp Tyr Gly Val Val Thr Ala Gly Gly Lys Gln
            690                 695                 700
Lys Pro Glu Ser Phe Lys Glu Ser Val Gln Ile Leu Lys Gly Ala Thr
705                 710                 715                 720
Asp Phe Val Gly Lys Phe Phe Tyr Gln Ile Ser Gln His Arg Asn Tyr
                725                 730                 735
Gln Arg Glu Leu Asp Gly Leu Ala Ser Thr Ile Ala Phe
            740                 745
```

```
<210> SEQ ID NO 41
<211> LENGTH: 744
<212> TYPE: PRT
<213> ORGANISM: Emericella nidulans

<400> SEQUENCE: 41

Met Ala Thr Ser Ile Thr Ala Gly Leu Gln Lys Ala Gln Gln Ala Val
1               5                   10                  15

Gln Asp Thr Ala Thr Lys Asn Lys Lys Ile Val Asp Ile Ser His Asp
            20                  25                  30

Thr Val Asn Val His Thr Asp Gln Glu Gln Arg Thr Asp Phe Gly Val
        35                  40                  45

Ala Ile Thr Asp Pro Asp His Trp Leu Arg Val Thr Asn Glu Thr His
    50                  55                  60

Ser Gly Pro Ser Leu Leu Glu Asp His Ile Ala Arg Glu Arg Ile His
65                  70                  75                  80

Arg Phe Asp His Glu Arg Ile Pro Glu Arg Val Val His Ala Arg Gly
                85                  90                  95

Thr Gly Ala Tyr Gly Asn Phe Thr Leu Lys Glu Ser Ile Glu Asp Leu
            100                 105                 110

Thr Tyr Ala Gly Val Leu Thr Asp Thr Ser Arg Asn Thr Pro Val Phe
        115                 120                 125

Val Arg Phe Ser Thr Val Gln Gly Ser Arg Gly Ser Ala Asp Thr Val
    130                 135                 140

Arg Asp Val Arg Gly Phe Ala Val Lys Phe Tyr Thr Asp Glu Gly Asn
145                 150                 155                 160

Trp Asp Ile Val Gly Asn Asn Ile Pro Val Phe Phe Ile Gln Asp Ala
                165                 170                 175

Ile Lys Phe Pro Asp Phe Val His Ala Val Lys Pro Glu Pro His Asn
            180                 185                 190

Glu Val Pro Gln Ala Gln Thr Ala His Asn Asn Phe Trp Asp Phe Val
        195                 200                 205

Tyr Leu His Pro Glu Ala Thr His Met Phe Met Trp Ala Met Ser Asp
    210                 215                 220

Arg Ala Ile Pro Arg Ser Tyr Arg Met Met Gln Gly Phe Gly Val Asn
225                 230                 235                 240

Thr Phe Ser Leu Val Asn Lys Glu Gly Lys Arg His Phe Val Lys Phe
                245                 250                 255

His Trp Ile Pro His Leu Gly Val His Ser Leu Val Trp Asp Glu Ala
            260                 265                 270

Leu Lys Leu Ala Gly Gln Asp Pro Asp Phe His Arg Lys Asp Leu Met
        275                 280                 285

Glu Ala Ile Asp Asn Lys Ala Tyr Pro Lys Trp Asp Phe Ala Ile Gln
    290                 295                 300

Ala Ile Pro Glu Glu Asp Gln Asp Lys Phe Glu Phe Asp Ile Phe Asp
305                 310                 315                 320

Ala Thr Lys Val Trp Pro Glu Glu Gln Val Pro Leu Arg Val Val Gly
                325                 330                 335

Glu Leu Glu Leu Asn Arg Asn Ile Asp Glu Phe Phe Pro Glu Thr Glu
            340                 345                 350

Gln Val Ala Phe Cys Thr Ser His Ile Val Pro Gly Ile Asp Phe Ser
        355                 360                 365

Asp Asp Pro Leu Leu Gln Gly Arg Asn Phe Ser Tyr Gln Asp Thr Gln
    370                 375                 380
```

```
Ile Ser Arg Leu Gly Val Asn Trp Glu Glu Ile Pro Ile Asn Arg Pro
385                 390                 395                 400

Val Cys Pro Phe Leu Asn His Asn Arg Asp Gly Ala Lys Arg His Arg
                405                 410                 415

Ile Thr Lys Gly Thr Val Asn Tyr Trp Pro Asn Arg Phe Glu Ala Asn
            420                 425                 430

Pro Pro Ala Ser Asp Lys Gly Phe Lys Ser His Pro Ala Pro Ile Thr
            435                 440                 445

Gly Arg Lys Arg Arg Asp Leu Thr Pro Lys Phe Lys Glu Tyr His Asn
        450                 455                 460

Gln Ala Gln Leu Phe Tyr Asn Ser Leu Ser Glu Val Glu Lys Val His
465                 470                 475                 480

Val Lys Lys Ala Phe Ser Phe Glu Leu Asp His Cys Asp Asp Pro Ile
                485                 490                 495

Val Tyr Glu Arg Leu Ala Gly Gln Arg Leu Ala Glu Ile Asp Leu Pro
                500                 505                 510

Leu Ala Gln Ala Val Ala Glu Met Val Gly Ala Pro Ile Pro Thr Lys
            515                 520                 525

Ala Leu Arg Asp Asn His Gly Lys Thr Ser Val Arg Leu Ser Gln Phe
530                 535                 540

Asp Phe Thr Pro Lys Ala Pro Gly Ile Ile Ser Arg Arg Ile Ala Ile
545                 550                 555                 560

Ile Ile Gly Asp Gly Tyr Asp Lys Ile Ala Phe Asn Gly Met Lys Ala
                565                 570                 575

Ala Ile Leu Ala Ala Ala Ser Ala Pro Leu Arg His Trp His Gln Thr
            580                 585                 590

Ser Ala Ile Tyr Ala Gln Gly Glu Asp Lys Asn Ser Ser Lys Gly Val
        595                 600                 605

Ile Pro Asp His Met Tyr Asp Gly Met Arg Ser Thr Met Phe Asp Ala
        610                 615                 620

Thr Phe Ile Pro Gly Gly Ser His Ile Glu Thr Leu Gln Lys Asn Gly
625                 630                 635                 640

Gln Ile Arg Tyr Trp Ile Ala Glu Thr Phe Gly His Leu Lys Ala Leu
                645                 650                 655

Gly Ala Met Gly Glu Ala Ala Gln Leu Val Lys Glu Val Leu Gly Asn
            660                 665                 670

Val Met Gly Val Gln Ile Ala Gly Ala Asp Ser Ala Glu Pro Val Glu
        675                 680                 685

Trp Tyr Gly Val Val Thr Ala Arg Gly Pro Glu Ser Ala Glu Ser Leu
        690                 695                 700

Ser Glu Gly Phe Lys Val Leu Lys Asp Ala Gly Asp Phe Thr Ser Lys
705                 710                 715                 720

Phe Phe Tyr Gln Ile Ser Gln His Arg Asn Trp Gln Arg Glu Leu Asp
                725                 730                 735

Gly Leu Ala Ser Thr Val Ala Phe
            740

<210> SEQ ID NO 42
<211> LENGTH: 730
<212> TYPE: PRT
<213> ORGANISM: Aspergillus niger
```

<400> SEQUENCE: 42

```
Met Arg His Phe Trp Leu Leu Pro Ala Val Ala Gly Ile Ala Gly Ala
1               5                   10                  15
Gln Cys Pro Tyr Leu Ser Gly Glu Met Ser Phe Thr Gln Glu Gln Asp
            20                  25                  30
Asn Ala Gly Asp Thr Ile Glu Val Thr Glu Gln Pro Ile Asp Asn Thr
        35                  40                  45
Leu Tyr Val Asn Asp Thr Gly Ser Tyr Met Thr Thr Asp Phe Gly Thr
    50                  55                  60
Pro Ile Ser Asp Gln Thr Ser Leu Lys Ala Gly Arg Gly Pro Thr
65                  70                  75                  80
Leu Leu Glu Asp Phe Ile Phe Arg Gln Lys Leu Gln Arg Phe Asp His
                85                  90                  95
Glu Arg Val Pro Glu Arg Val Val His Ala Arg Gly Ala Gly Ala Tyr
            100                 105                 110
Gly Thr Phe Lys Ser Tyr Ala Asp Trp Ser Asn Val Thr Ala Ala Asp
            115                 120                 125
Phe Leu Ser Ala Asn Asp Lys Glu Thr Pro Met Phe Cys Arg Phe Ser
    130                 135                 140
Thr Val Gly Phe Arg Gly Ser Val Asp Thr Ala Arg Asp Val His
145                 150                 155                 160
Gly His Ala Cys Arg Phe Tyr Thr Asp Glu Gly Asn Tyr Asp Ile Val
                165                 170                 175
Gly Ile Asn Phe Ala Pro Phe Phe Ile Gln Asp Ala Ile Gln Phe Pro
            180                 185                 190
Asp Leu Val His Ala Ile Lys Pro Met Pro Asn Asn Glu Ile Pro Gln
            195                 200                 205
Ala Ala Thr Ala His Thr Ser Ala Trp Asp Phe Phe Ser Gln Gln Ser
    210                 215                 220
Thr Ala Leu His Ser Ala Leu Trp Leu Met Ser Gly Asn Gly Ile Pro
225                 230                 235                 240
Arg Ser Phe Arg His Met Asn Gly Tyr Gly Val His Ser Phe Arg Phe
                245                 250                 255
Val Ala Ala Asn Gly Thr Ser Lys Val Val Arg Thr Pro Trp Lys Ser
            260                 265                 270
Gln Gln Gly Val Ala Ser Leu Val Trp Asp Glu Ala Gln Ala Ala Ala
    275                 280                 285
Gly Lys Asn Ser Asp Tyr His Arg Gln Asp Leu Tyr Asn Ala Met Pro
290                 295                 300
Asn Gly His Tyr Pro Lys Tyr Glu Leu Gln Ala Gln Ile Met Asp Glu
305                 310                 315                 320
Ala Asp Met Leu Arg Phe Gly Phe Asp Leu Leu Asp Pro Thr Lys Leu
                325                 330                 335
Val Pro Glu Glu Val Pro Tyr Thr Pro Leu Gly Met Met Glu Leu
            340                 345                 350
Asn Ala Asn Pro Thr Asn Tyr Phe Ala Glu Val Glu Gln Ala Gly Phe
    355                 360                 365
Gln Pro Gly His Val Val Pro Gly Ile Asp Phe Thr Asp Asp Pro Leu
370                 375                 380
Leu Gln Gly Arg Leu Phe Ser Tyr Leu Asp Thr Gln Leu Thr Arg His
385                 390                 395                 400
```

```
Gly Gly Pro Asn Phe Glu Gln Ile Pro Val Asn Arg Pro Arg Lys Pro
                405                 410                 415

Val His Asn Asn Arg Asp Gly Phe Gly Gln Gln Gln Ile Pro Thr
            420                 425                 430

Asn Asn Trp Ala Tyr Thr Pro Asn Ser Met Ser Asn Gly Tyr Pro Met
            435                 440                 445

Gln Ala Asn Gln Thr Gln Gly His Gly Phe Phe Thr Ala Pro Tyr Arg
    450                 455                 460

Tyr Ala Ser Gly His Leu Val Arg Gln Thr Ser Pro Thr Phe Asn Asp
465                 470                 475                 480

His Trp Ser Gln Pro Ala Met Phe Trp Asn Ser Leu Ile Pro Ala Glu
                485                 490                 495

Gln Gln Met Val Val Asn Ala Ile Val Phe Glu Asn Ser Lys Val Asn
                500                 505                 510

Ser Pro His Val Arg Lys Asn Val Val Asn Gln Leu Asn Met Val Asn
            515                 520                 525

Asn Asn Leu Ala Val Arg Val Ala Arg Gly Leu Gly Leu Asp Glu Pro
530                 535                 540

Ser Pro Asn Pro Thr Tyr Tyr Thr Ser Asn Lys Thr Ser Asn Val Gly
545                 550                 555                 560

Thr Phe Gly Lys Pro Leu Leu Ser Ile Glu Gly Leu Gln Val Gly Phe
                565                 570                 575

Leu Ala Ser Asn Ser His Pro Glu Ser Ile Lys Gln Gly Gln Ala Met
            580                 585                 590

Ala Ala Gln Phe Ser Ala Gly Val Asp Leu Asn Ile Val Thr Glu
            595                 600                 605

Ala Tyr Ala Asp Gly Val Asn Thr Thr Tyr Ala Leu Ser Asp Ala Ile
    610                 615                 620

Asp Phe Asp Ala Leu Ile Ile Ala Asp Gly Val Gln Ser Leu Phe Ala
625                 630                 635                 640

Ser Pro Ala Leu Ala Asn Gln Met Asn Ser Thr Ala Thr Ser Thr Leu
                645                 650                 655

Tyr Pro Pro Ala Arg Pro Phe Gln Ile Leu Val Asp Ser Phe Arg Tyr
                660                 665                 670

Gly Lys Pro Val Ala Ala Val Gly Ser Gly Ser Val Ala Leu Lys Asn
            675                 680                 685

Ala Gly Ile Asp Ser Ser Arg Ser Gly Val Tyr Thr Gly Ser Ser Glu
    690                 695                 700

Thr Thr Glu Lys Ile Ala Lys Glu Val Leu Glu Gly Leu Tyr Thr Phe
705                 710                 715                 720

Arg Phe Val Asp Arg Phe Ala Leu Asp Glu
                725                 730

<210> SEQ ID NO 43
<211> LENGTH: 503
<212> TYPE: PRT
<213> ORGANISM: Histoplasma capsulatum

<400> SEQUENCE: 43

Met Gly Ala Asp Asp Thr Phe Asn Ser Tyr Arg Tyr Lys Asp Thr Pro
1               5                   10                  15

Thr Tyr Thr Asp Ser Asn Gly Cys Pro Val Met Asp Pro Glu Ser Ser
            20                  25                  30
```

```
Gln Arg Val Gly Glu Asn Gly Pro Leu Leu Gln Asp Phe His Leu
         35                  40                  45

Ile Asp Leu Leu Ala His Phe Asp Arg Glu Arg Ile Pro Glu Arg Val
 50                  55                  60

Val His Ala Lys Gly Ala Gly Ala Tyr Gly Glu Phe Glu Val Leu Asp
 65                  70                  75                  80

Asp Ile Ser Asp Ile Thr Thr Ile Asn Met Leu Lys Gly Val Gly Lys
                 85                  90                  95

Lys Thr Lys Leu Val Thr Arg Phe Ser Thr Val Gly Gly Glu Lys Gly
                100                 105                 110

Ser Ala Asp Ser Ala Arg Asp Pro Arg Gly Phe Ser Thr Lys Phe Tyr
            115                 120                 125

Thr Glu Glu Gly Asn Trp Asp Trp Val Phe Asn Asn Thr Pro Val Phe
        130                 135                 140

Phe Leu Arg Asp Pro Ser Lys Phe Pro Leu Phe Ile His Thr Gln Lys
145                 150                 155                 160

Arg Asn Pro Gln Thr Asn Leu Lys Asp Ala Thr Met Phe Trp Asp Tyr
                165                 170                 175

Leu Ser Thr His Gln Glu Ala Ile His Gln Val Met His Leu Phe Ser
                180                 185                 190

Asp Arg Gly Thr Pro Tyr Ser Tyr Arg His Met Asn Gly Tyr Ser Gly
            195                 200                 205

His Thr Phe Lys Trp Leu Thr Pro Asp Gly Gly Phe Asn Tyr Val Gln
        210                 215                 220

Ile His Leu Lys Thr Asp Gln Gly Ser Lys Thr Leu Thr Asn Glu Glu
225                 230                 235                 240

Ala Thr Lys Leu Ala Ala Glu Asn Pro Asp Trp His Thr Glu Asp Leu
                245                 250                 255

Phe Arg Ala Ile Glu Arg Gly Glu Tyr Pro Ser Trp Thr Cys Tyr Val
            260                 265                 270

Gln Val Leu Ser Pro Gln Gln Ala Glu Lys Phe Arg Trp Asn Ile Phe
        275                 280                 285

Asp Leu Thr Lys Val Trp Pro His Ser Glu Val Pro Leu Arg Arg Phe
290                 295                 300

Gly Arg Leu Val Leu Asn Lys Asn Pro Gln Asn Tyr Phe Ala Glu Met
305                 310                 315                 320

Glu Gln Ala Ala Phe Ser Pro Ser His Leu Val Pro Gly Val Glu Pro
                325                 330                 335

Ser Ala Asp Pro Val Leu Gln Ser Arg Leu Phe Ser Tyr Pro Asp Thr
            340                 345                 350

His Arg His Arg Leu Gly Val Asn Tyr Gln Gln Ile Pro Val Asn Cys
        355                 360                 365

Pro Leu Arg Ala Phe Asn Pro Tyr Gln Arg Asp Gly Ala Met Ala Val
    370                 375                 380

Asn Gly Asn Tyr Gly Ala Asn Pro Asn Tyr Pro Ser Thr Phe Arg Arg
385                 390                 395                 400

Met Asn Tyr Met Pro Val Lys Ala Ser Gln Glu His Glu Lys Trp Thr
                405                 410                 415

Gly Ala Val Leu Ala Lys Gln Leu Pro Val Thr Asp Glu Asp Phe Val
            420                 425                 430

Gln Ala Asn Gly Leu Trp Gln Val Leu Gly Arg Gln Pro Gly Gln Gln
        435                 440                 445
```

```
Ala Asn Phe Val Lys Asn Val Ala Gly His Leu Cys Asn Ala Glu Gln
    450                 455                 460
Lys Val Arg Lys Ala Ala Tyr Gly Met Phe Ile Arg Val Asn Lys Asp
465                 470                 475                 480
Leu Gly Ser Ser Ile Glu Ser Ser Thr Glu Ala Leu Val Ala Ser Gln
                485                 490                 495
Ala Gln Ser Gln Pro Arg Leu
            500

<210> SEQ ID NO 44
<211> LENGTH: 501
<212> TYPE: PRT
<213> ORGANISM: Emericella nidulans

<400> SEQUENCE: 44

Met Gly Gln Asn Asp Asp Gln Lys Thr Tyr Arg Tyr Asn Glu Ser Pro
1               5                   10                  15
Val Tyr Thr Thr Ser Asn Gly Cys Pro Val Met Asp Pro Gln Ala Ser
                20                  25                  30
Gln Arg Val Gly Pro Asn Gly Pro Leu Leu Leu Gln Asp Phe Asn Leu
            35                  40                  45
Ile Asp Leu Leu Ala His Phe Asp Arg Glu Arg Ile Pro Glu Arg Val
    50                  55                  60
Val His Ala Lys Gly Ala Gly Ala Tyr Gly Glu Phe Glu Val Thr Asp
65                  70                  75                  80
Asp Ile Ser Asp Ile Thr Val Ile Asp Met Leu Lys Gly Val Gly Lys
                85                  90                  95
Lys Thr Lys Thr Phe Val Arg Phe Ser Thr Val Gly Gly Glu Lys Gly
            100                 105                 110
Ser Pro Asp Ser Ala Arg Asp Pro Arg Gly Phe Ala Cys Lys Phe Tyr
    115                 120                 125
Thr Glu Glu Gly Asn Trp Asp Trp Val Phe Asn Asn Thr Pro Val Phe
130                 135                 140
Phe Leu Arg Asp Pro Ser Lys Phe Pro Met Phe Ile His Thr Gln Lys
145                 150                 155                 160
Arg Asn Pro Gln Thr Asn Leu Lys Asp Ala Thr Met Phe Trp Asp Tyr
                165                 170                 175
Leu Ser Thr His Gln Glu Ala Val His Gln Val Met His Leu Phe Ser
            180                 185                 190
Asp Arg Gly Thr Pro Tyr Ser Tyr Arg His Met Asn Gly Tyr Ser Gly
    195                 200                 205
His Thr Tyr Lys Trp Ile Lys Pro Asp Gly Thr Phe Asn Tyr Val Gln
210                 215                 220
Leu His Leu Lys Thr Gly Gln Gly Asn Lys Thr Phe Thr Asp Ala Glu
225                 230                 235                 240
Ala Thr Arg Leu Ala Ala Glu Asn Pro Asp Trp His Thr Gln Asp Leu
                245                 250                 255
Phe Asn Ala Ile Ala Arg Gly Glu Tyr Pro Ser Trp Thr Cys Tyr Val
            260                 265                 270
Gln Thr Leu Ser Pro Glu Gln Ala Glu Lys Phe Arg Trp Asn Ile Phe
    275                 280                 285
Asp Leu Thr Lys Val Trp Pro Gln Ser Glu Val Pro Leu Arg Arg Phe
290                 295                 300
Gly Arg Phe Thr Leu Asn Lys Asn Pro Glu Asn Tyr Phe Ala Glu Val
305                 310                 315                 320
```

```
Glu Gln Ala Ala Phe Ser Pro Ser His Leu Val Pro Gly Val Glu Pro
                325                 330                 335

Ser Ala Asp Pro Val Leu Gln Ala Arg Leu Phe Ser Tyr Pro Asp Thr
            340                 345                 350

His Arg His Arg Leu Gly Thr Ser Asn Tyr Gln Ser Ile Pro Val Asn
        355                 360                 365

Cys Pro Leu Arg Ala Phe Thr Pro Phe His Arg Asp Gly Ala Met Ser
    370                 375                 380

Val Asn Gly Asn His Gly Ala Asn Pro Asn Tyr Pro Ser Thr Phe Arg
385                 390                 395                 400

Pro Leu Gln Tyr Lys Pro Val Lys Ala Ser Gln Glu His Glu Lys Trp
                405                 410                 415

Ala Gly Ser Val Val Thr Glu Gln Leu Pro Val Thr Asp Glu Asp Phe
            420                 425                 430

Val Gln Ala Asn Gly Leu Trp Lys Val Leu Gly Arg Gln Pro Gly Gln
        435                 440                 445

Gln Glu Asn Phe Val Gly Asn Val Ala Gly His Leu Cys Asn Ala His
    450                 455                 460

Pro Arg Val Arg Gln Ala Thr Tyr Gly Met Phe Arg Arg Val Asn Ala
465                 470                 475                 480

Asp Leu Gly Lys Arg Ile Glu Lys Ala Thr Glu Lys Lys Ala Thr Glu
                485                 490                 495

Ala Arg Ala Arg Leu
                500

<210> SEQ ID NO 45
<211> LENGTH: 515
<212> TYPE: PRT
<213> ORGANISM: Saccharomyces cerevisiae

<400> SEQUENCE: 45

Met Ser Lys Leu Gly Gln Glu Lys Asn Glu Val Asn Tyr Ser Asp Val
1               5                   10                  15

Arg Glu Asp Arg Val Val Thr Asn Ser Thr Gly Asn Pro Ile Asn Glu
            20                  25                  30

Pro Phe Val Thr Gln Arg Ile Gly Glu His Gly Pro Leu Leu Leu Gln
        35                  40                  45

Asp Tyr Asn Leu Ile Asp Ser Leu Ala His Phe Asn Arg Glu Asn Ile
    50                  55                  60

Pro Gln Arg Asn Pro His Ala His Gly Ser Gly Ala Phe Gly Tyr Phe
65                  70                  75                  80

Glu Val Thr Asp Asp Ile Thr Asp Ile Cys Gly Ser Ala Met Phe Ser
                85                  90                  95

Lys Ile Gly Lys Arg Thr Lys Cys Leu Thr Arg Phe Ser Thr Val Gly
            100                 105                 110

Gly Asp Lys Gly Ser Ala Asp Thr Val Arg Asp Pro Arg Gly Phe Ala
        115                 120                 125

Thr Lys Phe Tyr Thr Glu Glu Gly Asn Leu Asp Trp Val Tyr Asn Asn
    130                 135                 140

Thr Pro Val Phe Phe Ile Arg Asp Pro Ser Lys Phe Pro His Phe Ile
145                 150                 155                 160

His Thr Gln Lys Arg Asn Pro Gln Thr Asn Leu Arg Asp Ala Asp Met
                165                 170                 175
```

Phe Trp Asp Phe Leu Thr Thr Pro Glu Asn Gln Val Ala Ile His Gln
              180                 185                 190

Val Met Ile Leu Phe Ser Asp Arg Gly Thr Pro Ala Asn Tyr Arg Ser
          195                 200                 205

Met His Gly Tyr Ser Gly His Thr Tyr Lys Trp Ser Asn Lys Asn Gly
      210                 215                 220

Asp Trp His Tyr Val Gln Val His Ile Lys Thr Asp Gln Gly Ile Lys
225                 230                 235                 240

Asn Leu Thr Ile Glu Glu Ala Thr Lys Ile Ala Gly Ser Asn Pro Asp
                245                 250                 255

Tyr Cys Gln Gln Asp Leu Phe Glu Ala Ile Gln Asn Gly Asn Tyr Pro
              260                 265                 270

Ser Trp Thr Val Tyr Ile Gln Thr Met Thr Glu Arg Asp Ala Lys Lys
          275                 280                 285

Leu Pro Phe Ser Val Phe Asp Leu Thr Lys Val Trp Pro Gly Gly Gln
      290                 295                 300

Phe Pro Leu Arg Arg Val Gly Lys Ile Val Leu Asn Glu Asn Pro Leu
305                 310                 315                 320

Asn Phe Phe Ala Gln Val Glu Gln Ala Ala Phe Ala Pro Ser Thr Thr
                325                 330                 335

Val Pro Tyr Gln Glu Ala Ser Ala Asp Pro Val Leu Gln Ala Arg Leu
              340                 345                 350

Phe Ser Tyr Ala Asp Ala His Arg Tyr Arg Leu Gly Pro Asn Phe His
          355                 360                 365

Gln Ile Pro Val Asn Cys Pro Tyr Ala Ser Lys Phe Phe Asn Pro Ala
      370                 375                 380

Ile Arg Asp Gly Pro Met Asn Val Asn Gly Asn Phe Gly Ser Glu Pro
385                 390                 395                 400

Thr Tyr Leu Ala Asn Asp Lys Ser Tyr Thr Tyr Ile Gln Gln Asp Arg
                405                 410                 415

Pro Ile Gln Gln His Gln Glu Val Trp Asn Gly Pro Ala Ile Pro Tyr
              420                 425                 430

His Trp Ala Thr Ser Pro Gly Asp Val Asp Phe Val Gln Ala Arg Asn
          435                 440                 445

Leu Tyr Arg Val Leu Gly Lys Gln Pro Gly Gln Gln Lys Asn Leu Ala
      450                 455                 460

Tyr Asn Ile Gly Ile His Val Glu Gly Ala Cys Pro Gln Ile Gln Gln
465                 470                 475                 480

Arg Val Tyr Asp Met Phe Ala Arg Val Asp Lys Gly Leu Ser Glu Ala
                485                 490                 495

Ile Lys Lys Val Ala Glu Ala Lys His Ala Ser Glu Leu Ser Ser Asn
              500                 505                 510

Ser Lys Phe
        515

<210> SEQ ID NO 46
<211> LENGTH: 487
<212> TYPE: PRT
<213> ORGANISM: Candida albicans

<400> SEQUENCE: 46

Met Ala Pro Thr Phe Thr Asn Ser Asn Gly Gln Pro Ile Pro Glu Pro
1               5                   10                  15

```
Phe Ala Thr Gln Arg Val Gly Gln His Gly Pro Leu Leu Leu Gln Asp
            20                  25                  30

Phe Asn Leu Ile Asp Ser Leu Ala His Phe Asp Arg Glu Arg Ile Pro
            35                  40                  45

Glu Arg Val Val His Ala Lys Gly Ser Gly Ala Tyr Gly Val Phe Glu
        50                  55                  60

Val Thr Asp Asp Ile Thr Asp Ile Cys Ala Ala Lys Phe Leu Asp Thr
 65                  70                  75                  80

Val Gly Lys Lys Thr Arg Ile Phe Thr Arg Phe Ser Thr Val Gly Gly
                85                  90                  95

Glu Leu Gly Ser Ala Asp Thr Ala Arg Asp Pro Arg Gly Phe Ala Thr
            100                 105                 110

Lys Ile Tyr Thr Glu Glu Gly Asn Leu Asp Leu Val Tyr Asn Asn Thr
            115                 120                 125

Pro Val Phe Phe Ile Arg Asp Pro Ser Lys Phe Pro His Phe Ile His
    130                 135                 140

Thr Gln Lys Arg Asn Pro Glu Thr His Leu Lys Asp Ala Asn Met Phe
145                 150                 155                 160

Trp Asp Tyr Leu Thr Ser Asn Glu Glu Ser Ile His Gln Val Met Val
                165                 170                 175

Leu Phe Ser Asp Arg Gly Thr Pro Ala Ser Tyr Arg Glu Met Asn Gly
            180                 185                 190

Tyr Ser Gly His Thr Tyr Lys Trp Ser Asn Lys Lys Gly Glu Trp Phe
        195                 200                 205

Tyr Val Gln Val His Phe Ile Ser Asp Gln Gly Ile Lys Thr Leu Asn
    210                 215                 220

Asn Glu Glu Ala Gly Ala Leu Ala Gly Ser Asn Pro Asp Tyr Ala Gln
225                 230                 235                 240

Glu Asp Leu Phe Lys Asn Ile Ala Ala Gly Asn Tyr Pro Ser Trp Thr
                245                 250                 255

Ala Tyr Ile Gln Thr Met Thr Glu Ala Glu Ala Lys Glu Ala Glu Phe
            260                 265                 270

Ser Val Phe Asp Leu Thr Lys Val Trp Pro His Arg Lys Tyr Pro Met
        275                 280                 285

Arg Arg Phe Gly Lys Phe Thr Leu Asn Glu Asn Pro Glu Asn Tyr Phe
    290                 295                 300

Ala Glu Val Glu Gln Ala Ala Phe Ser Pro Ala His Thr Val Pro Tyr
305                 310                 315                 320

Met Glu Pro Ser Ala Asp Pro Val Leu Gln Ser Arg Leu Phe Ser Tyr
                325                 330                 335

Ala Asp Thr His Arg Pro His Arg Leu Gly Thr Asn Tyr Thr Gln Ile
            340                 345                 350

Pro Val Asn Cys Pro Val Thr Gly Ala Val Phe Asn Pro His Ser Arg
        355                 360                 365

Asp Gly Ala Met Thr Val Asn Gly Asn Leu Gly Ser His Pro Asn Tyr
    370                 375                 380

Leu Ala Ser Asp Lys Pro Val Glu Phe Lys Gln Phe Ser Ser Phe Gln
385                 390                 395                 400

Glu Asp Gln Glu Val Trp Asn Gly Ala Ala Thr Pro Phe His Trp Lys
                405                 410                 415

Ala Thr Pro Ala Asp Phe Lys Gln Ala Gln Glu Leu Trp Lys Val Leu
            420                 425                 430
```

```
Lys Arg Tyr Pro Asn Gln Gln Glu His Leu Ala His Asn Ile Ala Val
        435                 440                 445

His Ala Ala Gly Ala Asp Ala Ala Ile Gln Asp Arg Val Phe Ala Tyr
    450                 455                 460

Phe Gly Lys Val Ser Gln Asp Leu Ala Asp Ala Ile Lys Lys Glu Val
465                 470                 475                 480

Leu Glu Leu Ser Pro Arg Lys
                485

<210> SEQ ID NO 47
<211> LENGTH: 507
<212> TYPE: PRT
<213> ORGANISM: Hansenula polymorpha

<400> SEQUENCE: 47

Met Ser Asn Pro Pro Val Phe Thr Thr Ser Gln Gly Cys Pro Val Ser
1               5                   10                  15

Asp Pro Phe Thr Thr Gln Arg Ile Pro Leu Asp Ser Thr Gly Tyr Lys
            20                  25                  30

Tyr Ala Pro Pro Ile Gly Pro Leu Leu Leu Gln Asp Phe Lys Leu Ile
        35                  40                  45

Asp Thr Leu Ser His Phe Asp Arg Glu Arg Ile Pro Glu Arg Val Val
50                  55                  60

His Ala Lys Gly Ala Gly Ala Tyr Gly Val Phe Glu Val Thr Asp Asp
65                  70                  75                  80

Ile Thr Asp Val Cys Ser Ala Lys Phe Leu Asp Thr Val Gly Lys Lys
                85                  90                  95

Thr Arg Ile Phe Thr Arg Phe Ser Thr Val Gly Gly Glu Lys Gly Ser
            100                 105                 110

Ala Asp Thr Ala Arg Asp Pro Arg Gly Phe Ala Thr Lys Phe Tyr Thr
        115                 120                 125

Glu Asp Gly Asn Leu Asp Leu Val Tyr Asn Asn Thr Pro Ile Phe Phe
130                 135                 140

Ile Arg Asp Pro Ile Lys Phe Pro His Phe Ile His Thr Gln Lys Arg
145                 150                 155                 160

Asn Pro Ala Thr Asn Leu Lys Asp Pro Asn Met Phe Trp Asp Tyr Leu
            165                 170                 175

Thr Ala Asn Asp Glu Ser Leu His Gln Val Met Tyr Leu Phe Ser Asn
        180                 185                 190

Arg Gly Thr Pro Ala Ser Tyr Arg Thr Met Asn Gly Tyr Ser Gly His
    195                 200                 205

Thr Tyr Lys Trp Tyr Asn Ser Lys Gly Glu Trp Val Tyr Val Gln Val
210                 215                 220

His Phe Ile Ala Asn Gln Gly Val His Asn Leu Leu Asp Glu Glu Ala
225                 230                 235                 240

Gly Arg Leu Ala Gly Glu Asp Pro Asp His Ser Thr Arg Asp Leu Trp
            245                 250                 255

Glu Ala Ile Glu Lys Gly Asp Tyr Pro Ser Trp Glu Cys Tyr Ile Gln
        260                 265                 270

Thr Met Thr Leu Glu Gln Ser Lys Lys Leu Pro Phe Ser Val Phe Asp
    275                 280                 285

Leu Thr Lys Val Trp Pro His Lys Asp Phe Pro Leu Arg His Phe Gly
290                 295                 300

Arg Phe Thr Leu Asn Glu Asn Pro Lys Asn Tyr Tyr Ala Glu Thr Glu
305                 310                 315                 320
```

-continued

```
Gln Ile Ala Phe Ser Pro Ser His Thr Val Pro Gly Met Glu Pro Ser
                325                 330                 335

Asn Asp Pro Val Leu Gln Ser Arg Leu Phe Ser Tyr Pro Asp Thr His
            340                 345                 350

Arg His Arg Leu Gly Pro Asn Tyr His Gln Ile Pro Val Asn Cys Pro
        355                 360                 365

Leu Lys Ser Gly Ser Phe Asn Pro Ile Asn Arg Asp Gly Pro Met Cys
    370                 375                 380

Val Asp Gly Asn Leu Gly Gly Thr Pro Asn Tyr Ala Asn Ala Tyr Asn
385                 390                 395                 400

Cys Pro Ile Gln Tyr Ala Val Ser Pro Lys Ala Ser Gly Asn Lys Pro
                405                 410                 415

Asp Glu Lys Tyr Thr Gly Glu Val Val Pro Tyr His Trp Glu His Thr
            420                 425                 430

Asp Tyr Asp Tyr Phe Gln Pro Lys Met Phe Trp Lys Val Leu Gly Arg
        435                 440                 445

Thr Pro Gly Glu Gln Glu Ser Leu Val Lys Asn Val Ala Asn His Val
    450                 455                 460

Ser Ala Ala Asp Glu Phe Ile Gln Asp Arg Val Tyr Glu Tyr Phe Ser
465                 470                 475                 480

Lys Ala Glu Pro Ile Ile Gly Asp Leu Ile Arg Lys Lys Val Gln Glu
                485                 490                 495

Leu Lys Arg Lys Ala Ser Ser Pro Ser Lys Ile
            500                 505
```

<210> SEQ ID NO 48
<211> LENGTH: 512
<212> TYPE: PRT
<213> ORGANISM: Schizosaccharomyces pombe

<400> SEQUENCE: 48

```
Met Asn Ser Lys Asp Ser Asn Thr Val Pro Val Tyr Thr Thr Asn Thr
1               5                   10                  15

Gly Cys Pro Ile Phe Asn Pro Met Ala Ala Arg Val Gly Lys Gly
            20                  25                  30

Gly Pro Val Leu Leu Gln Asp Ser His Leu Ile Asp Val Phe Gln His
        35                  40                  45

Phe Asp Arg Glu Arg Ile Pro Glu Arg Val Val His Ala Lys Gly Ser
    50                  55                  60

Gly Ala Phe Gly Glu Phe Glu Cys Thr Asp Asp Ile Thr Lys Tyr Thr
65                  70                  75                  80

Lys His Thr Met Phe Ser Lys Val Gly Lys Lys Thr Pro Met Val Ala
                85                  90                  95

Arg Phe Ser Thr Val Gly Gly Glu Arg Gly Thr Pro Asp Thr Ala Arg
            100                 105                 110

Asp Pro Arg Gly Phe Ala Leu Lys Phe Tyr Thr Asp Glu Gly Ile Phe
        115                 120                 125

Asp Met Val Gly Asn Asn Thr Pro Val Phe Phe Leu Arg Asp Pro Ala
    130                 135                 140

Lys Phe Pro Leu Phe Ile His Thr Gln Lys Arg Asn Pro Gln Asn Asp
145                 150                 155                 160

Met Lys Asp Ala Thr Met Phe Trp Asp Tyr Leu Ser Gln Asn Ala Glu
                165                 170                 175
```

-continued

```
Ser Ile His Gln Val Met Ile Leu Phe Ser Asp Leu Gly Gly Thr Pro
            180                 185                 190

Tyr Ser Tyr Arg Phe Met Asp Gly Phe Ser Ser His Thr Tyr Lys Phe
        195                 200                 205

Val Asn Asp Lys Gly Glu Phe Tyr Tyr Cys Lys Trp His Phe Ile Thr
    210                 215                 220

Asn Gln Gly Thr Lys Gly Leu Thr Asn Glu Glu Ala Ala Ala Leu Asp
225                 230                 235                 240

Gly Ser Asn Pro Asp His Ala Arg Gln Asp Leu Phe Glu Ala Ile Glu
                245                 250                 255

Arg Gly Asp Tyr Pro Ser Trp Thr Leu Tyr Val Gln Val Met Thr Pro
            260                 265                 270

Gln Glu Ala Glu Lys Tyr Arg Tyr Asn Ile Phe Asp Leu Thr Lys Val
        275                 280                 285

Trp Pro His Lys Asp Val Pro Met Gln Arg Val Gly Arg Phe Thr Leu
    290                 295                 300

Asn Gln Asn Pro Thr Asn Phe Phe Ala Asp Ile Glu Gln Ala Gly Phe
305                 310                 315                 320

Ser Pro Ser His Met Val Pro Gly Ile Glu Val Ser Ala Asp Pro Val
                325                 330                 335

Leu Gln Val Arg Thr Phe Ser Tyr Pro Asp Thr His Arg His Arg Leu
            340                 345                 350

Gly Ala Asn Phe Glu Gln Ile Pro Val Asn Ser Pro Lys Cys Pro Val
        355                 360                 365

Phe Asn Tyr Ser Arg Asp Gly Pro Met Asn Val Asn Gly Asn Gln Gly
    370                 375                 380

Asn Trp Pro Asn Tyr Pro Ser Ser Ile Arg Pro Leu Ala Lys Val Gln
385                 390                 395                 400

Tyr Glu Pro Asp Glu Gly His Glu Lys Trp Val Gly Gln Val Thr Tyr
                405                 410                 415

His Met Asp Glu Ile Thr Asp Val Asp Phe Glu Gln Pro Arg Ala Phe
            420                 425                 430

Trp Gln Asn Val Leu Gly Lys Lys Pro Gly Gln Gln Asp Asn Phe Val
        435                 440                 445

Lys Asn Val Ala Gly His Leu Ser Gly Ala Ile Ser Pro Val Arg Glu
    450                 455                 460

Arg Gln Tyr Gly Val Phe Thr Arg Val Asp Ser Glu Leu Gly Arg Arg
465                 470                 475                 480

Ile Arg Glu Ala Thr Glu Ala Glu Val Lys Lys Met Glu Glu Lys Ala
                485                 490                 495

Pro Lys Pro Ile Asn Lys Gly Glu Pro His Met Phe Gln Gly Ser Ser
            500                 505                 510
```

HISTOPLASMA CAPSULATUM CATALASE SEQUENCES AND THEIR USE IN THE DETECTION OF HISTOPLAMSA CAPSULATUM AND HISTOPLASMOSIS

CROSS REFERENCE TO RELATED APPLICATION

This application claims priority to U.S. Provisional Application Ser. No. 60/275,353 filed Mar. 13, 2001.

GOVERNMENT LICENSE RIGHTS

The studies described herein were supported at least in part by a Merit Review award administered through the Office of Research and Development, Medical Research Service, Department of Veterans Affairs. Thus, the federal government may have rights in this invention.

FIELD OF THE INVENTION

The present invention relates generally to compositions and methods for use in the detection of *Histoplasma capsulatum* and histoplasmosis.

BACKGROUND OF THE INVENTION

*Histoplasma capsulatum* is a dimorphic fungal pathogen capable of causing acute pulmonary disease in otherwise healthy individuals and lethal disease in immunocompromised humans (Ampel, 1996, *Emerg. Infect. Dis.*, 2: 109–116; Eissenberg, 1994, *The Interplay Between Histoplasma Capsulatum and Its Host Cells*, Vol, I, Ch. 6, W. B. Saunders Company, Ltd. London, UK; Wheat et al., 1985, *Am. J. Med.*, 78: 203–210). In its most serious form, the infection disseminates throughout the body. Disseminated histoplasmosis, coinciding with laboratory evidence of HIV infection, is regarded sufficient for a diagnosis of AIDS (Castro et al., 1992, *MMRW* 41: 1–14). Although AIDS currently represents the most prevalent immunocompromising disease of humans, a variety of other conditions or medical treatments can impair the human immune system and create susceptibility to diseases caused by the primary pathogen *H. capsulatum* and associated opportunistic pathogens (Goodwin et al., 1981, Medicine (Baltimore) 60: 321–266). These predisposing conditions include advanced age, diabetes, cancer chemotherapy, or immunosuppression induced to prevent rejection of transplanted organs (Wheat et al., 1982, *Ann. Intern. Med.*, 96: 159–163; Davies et al., 1978, *Am. J. Med.* 64: 94–100).

In nature, *H. capsulatum* exists as a mycelium that is well-adapted for a saprotrophic mode of growth in soil (Scherr & Weaver, 1953, *Bact. Rev.* 17: 51–92). After entrance of microconidia or mycelial fragments into a mammalian host, *H. capsulatum* differentiates into budding yeast (Maresca et al., 1994, *Trends Microbiol.*, 2: 110–114). In the animal host, the fungus experiences significant host-induced or environmental stress, including heat shock, exposure to higher osmolarity, changes in pH, and oxidative stress (Deepe, 1998, *J. Lab. Clin. Med.* 123: 201–205; Eissenberg & Goldman, 1994, *The Interplay Between Histoplasma Capsulatum and Its Host Cells*, Vol, I, Ch. 6, W. B. Saunders Company, Ltd., London, UK; Newman, 1999, *Trends Microbiol.*, 7: 67–71). The ability to resist or overcome environmental or host-induced stress is likely to be important for continued growth and virulence of *H. capsulatum*. In addition, host-induced or environmental stress may trigger changes in gene expression necessary for virulence.

Most fungi share considerable similarities at the nucleic acid and/or protein level. For example, there is considerable sequence identity for fungi rRNA at the sequence level. The ability to distinguish among various fungi may be of considerable importance clinically (Kasuga, T., et al., 1999, *J. Clin Micro.*, 37: 653–663). For example, *H. capsulatum* requires different clinical treatment than other fungal pathogens (Li, R-K., et al., 2000, *Antimicrobial Agents*, 44: 1734–1736; D. K. Stein and A. M. Sugar, 1989, *Diagn. Microbiol., Infect., Dis.*, 12: 221S–228S; Ampel, 1996). Thus, there is a need to distinguish between *H. capsulatum* and other fungi.

There is also a specific need to distinguish between *H. capsulatum* and the closely related organism, *Blastomyces dermititidis*. Although *B. dermititidis* is also an aggressive pathogen, *H. capsulatum* infection requires a different clinical treatment than infection with *B. dermititidis* (Li, R-K., et al., 2000; Ampel, 1996). Previous work indicates there is a high level of genetic similarity between *H. capsulatum* and *B. dermatitis*. For example, it has been shown that antibodies raised against *H. capsulatum* M antigen cross react with a similar sized protein in *B. dermatititis* (Hamilton, A. J. et al., 1990, *J. Med. Vet. Mycol.*, 28: 479–485). Therefore, there is a need to identify differences at the genomic level for the development of sequence-specific assays that will be able to differentiate these two closely related organisms.

There is a need for the development of methods which specifically detect *H. capsulatum* and distinguish this pathogen from other fungi, as well as closely related pathogens such as *Blastomyces dermititidis*. There is also need to distinguish a latent *H. capsulatum* infection from an ongoing case of histoplasmosis. The ability to closely monitor this disease in high risk populations will enable the development of early treatment protocols suitable for patients, such as immunosuppressed individuals, who may not be able to defend against advanced stages of infection.

SUMMARY OF THE INVENTION

The present invention is directed to the development and use of reagents for the detection of the dimorphic fungal pathogen *H. capsulatum*. The methods and reagents of the present invention employ different aspects of the biology of *H. capsulatum* catalase genes for the development of nucleic acid and protein-based assays. The present invention provides for both the detection of *H. capsulatum* infection, as well as the diagnosis of an active case of histoplasmosis. The methods and reagents of the present invention provide for the differentiation of *H. capsulatum* from other fungal pathogens such as *Blastomyces dermatititis, Aspergillus nidulans, Aspergillus fumigatus, Emericella nidulans, Neurospora crassa, Cryptococcus neoformans, Candida albicans* and *Coccidioides immitis*.

Thus, the present invention comprises methods and compositions to enable the specific detection of the *H. capsulatum* catalase A gene (CATA) intron sequences as a means to detect infection with the pathogen *H. capsulatum*.

In one aspect, the present invention comprises an isolated nucleic acid for detection of *H. capsulatum* comprising SEQ ID NO: 7 or the complement of SEQ ID NO: 7, or a fragment of SEQ ID NO: 7 or the complement of SEQ ID NO: 7 that hybridizes under highly stringent conditions to intron 1 of the *H. capsulatum* catalase A gene.

In another aspect, the present invention comprises an isolated nucleic acid for detection of *H. capsulatum* comprising SEQ ID NO: 8 or the complement of SEQ ID NO: 8, or a fragment of SEQ ID NO: 8 or the complement of SEQ ID NO: 8 that hybridizes under highly stringent conditions to intron 2 of the *H. capsulatum* catalase A gene.

In still another aspect, the present invention comprises an isolated nucleic acid for detection of *H. capsulatum* comprising: (a) the nucleotide sequences set forth in SEQ ID NO: 7 or SEQ ID NO: 8 or any complements thereof; (b) a nucleotide sequence having at least 70% sequence identity to any one of the sequences in (a); and (c) a fragment of any one of (a) or (b).

The present invention also comprises a method for detecting *H. capsulatum* in a sample, comprising the steps of: (a) providing a sample; and (b) assaying for the presence of DNA comprising intron 1 or intron 2 of the *H. capsulatum* catalase A gene (CATA) or a combination of intron 1 and intron 2 of the *H. capsulatum* catalase A gene in the sample, wherein the presence of said CATA intron DNA indicates that the sample contains *H. capsulatum*. In an embodiment, the method may comprise detection of *H. capsulatum* CATA intron 1 or CATA intron 2 by hybridization or PCR.

The present invention also comprises methods and compositions to enable the specific detection of the *H. capsulatum* catalase P gene (CATP) intron sequences as a means to detect infection with the pathogen *H. capsulatum*.

Thus, in one aspect, the present invention comprises an isolated nucleic acid for detection of *H. capsulatum* comprising SEQ ID NO: 9 or the complement of SEQ ID NO: 9, or a fragment of SEQ ID NO: 9 or the complement of SEQ ID NO: 9 that hybridizes under highly stringent conditions to intron 1 of the *H. capsulatum* catalase P gene.

In another aspect, the present invention comprises an isolated nucleic acid for detection of *H. capsulatum* comprising SEQ ID NO: 10 or the complement of SEQ ID NO: 10, or a fragment of SEQ ID NO: 10 or the complement of SEQ ID NO: 10 that hybridizes under highly stringent conditions to intron 2 of the *H. capsulatum* catalase P gene.

In yet another aspect, the present invention comprises an isolated nucleic acid for detection of *H. capsulatum* comprising SEQ ID NO: 11 or the complement of SEQ ID NO: 11, or a fragment of SEQ ID NO: 11 or the complement of SEQ ID NO: 11 that hybridizes under highly stringent conditions to intron 3 of the *H. capsulatum* catalase P gene.

The present invention also comprises an isolated nucleic acid for detection of *H. capsulatum* comprising: (a) the nucleotide sequences set forth in SEQ ID NO: 9, SEQ ID NO: 10, or SEQ ID NO: 11, or any complements thereof; (b) a nucleotide sequence having at least 70% sequence identity to any one of the sequences in (a); and (c) a fragment of any one of (a) or (b).

The present invention also comprises a method for detecting *H. capsulatum* in a sample, comprising the steps of: (a) providing a sample; and (b) assaying for the presence of DNA comprising intron 1, intron 2, or intron 3 of the *H. capsulatum* catalase P gene (CATP) or a combination thereof in the sample, wherein the presence of said CATP intron DNA indicates that the sample contains *H. capsulatum*. In an embodiment, the method may comprise detection of *H. capsulatum* CATP introns 1, 2 or 3 by hybridization or PCR.

Because of the high specificity of *H. capsulatum* intron sequences, the present invention also comprises a method to distinguish *H. capsulatum* from other fungal pathogens, or combinations of other fungal pathogens such as, but not limited to, *Blastomyces dermatititis, Aspergillus nidulans, Aspergillus fumigates, Emericella nidulans, Neurospora crassa, Cryptococcus neoformans, Candida albicans* and *Coccidioides immitis*. Thus, in yet another aspect, the present invention comprises a method for distinguishing whether a patient has been exposed to *H. capsulatum* or at least one second pathogen comprising: (a) obtaining a sample from a subject; (b) exposing the sample under high stringency hybridization conditions to at least one isolated nucleic acid that hybridizes to at least one intron from the *H. capsulatum* catalase A (CATA) or catalase P (CATP) genes; (c) exposing the sample under high stringency hybridization conditions to at least one isolated nucleic acid that hybridizes to sequences from a second pathogen; (d) determining whether there is hybridization of the *H. capsulatum* catalase A or catalase P intron sequences to the sample; (e) determining whether there is hybridization of the sequences from the second pathogen to the sample; (f) assessing the presence of *H. capsulatum* in the sample, wherein a sample comprising *H. capsulatum* exhibits detectable hybridization to the *H. capsulatum* catalase A or catalase P intron sequences and a sample lacking *H. capsulatum* does not exhibit hybridization; and (g) assessing the presence of the second pathogen in the sample, wherein a sample comprising the second pathogen exhibits detectable hybridization to the sequences derived from the second pathogen and a sample lacking the second pathogen does not exhibit hybridization. In an embodiment, the method may comprise detection of *H. capsulatum* CATA or CATP introns by hybridization or PCR.

The present invention also employs catalase A and P polypeptides for detection of *H. capsulatum*. In one aspect, the present invention comprises a method for detecting *H. capsulatum* in a sample, comprising the steps of: (a) providing a sample; and (b) assaying for the presence *H. capsulatum* catalase P polypeptide or *H. capsulatum* catalase A polypeptide in said sample, wherein a sample comprising *H. capsulatum* catalase P or catalase A polypeptide contains *H. capsulatum*. In an embodiment the method employs an immunoassay for catalase A or catalase P polypeptides.

In anther aspect, the present invention comprises a protein-based assay for distinguishing whether a subject has been exposed to *H. capsulatum* or at least one second pathogen comprising the steps of: (a) obtaining a sample from the subject; (b) preparing the sample for immunoassay; (c) conducting an immunoassay with an antibody preparation which specifically recognizes *H. capsulatum* catalase P or catalase A polypeptide; (d) conducting an immunoassay with an antibody preparation which specifically recognizes at least one polypeptide from the second pathogen; (e) detecting the presence or absence of an immune complex in steps (c) and (d); and (f) determining exposure to *H. capsulatum* or the second pathogen, wherein an immune complex comprising *H. capsulatum* catalase P polypeptide or catalase A polypeptide is detected in subjects who have been infected with *H. capsulatum,* and wherein an immune complex comprising polypeptides from the second pathogen is detected in subjects who have been infected with the second pathogen.

The present invention also comprises a method for the diagnosis of histoplasmosis in a subject, comprising the steps of: (a) assaying for the presence of *H. capsulatum* catatlase P polypeptide in a sample obtained from the subject; (b) if *H. capsulatum* catatlase P polypeptide is detected, assaying for the presence of *H. capsulatum* catalase A polypeptide in the sample; and (c) determining whether the patient has histoplasmosis, wherein the presence of both *H. capsulatum* catalase P polypeptide and catalase A polypeptide indicates a diagnosis of histoplasmosis.

The present invention also comprises a method for the diagnosis of histoplasmosis in a subject, comprising the steps of: (a) assaying for the presence of *H. capsulatum* catalaseP polypeptide in a sample obtained from the subject; (b) if *H. capsulatum* catalaseP polypeptide is detected, assaying for the presence of *H. capsulatum* catalaseA polypeptide in the sample; and (c) determining whether the patient has histoplasmosis, wherein the presence of both *H. capsulatum* catalase P polypeptide and catalase A polypeptide indicates a diagnosis of histoplasmosis.

In another aspect, the present invention comprises a method for the purification of cytosolic catalase enzyme from a sample comprising: (a) preparing a clarified cellular supernatant from a sample; (b) applying the clarified cellular supernatant to a sepharose column; and (c) eluting proteins from the column with a decreasing concentration of ammonium sulfate/sodium phosphate buffer, wherein fractions comprising catalase are capable of degrading hydrogen peroxide.

The present invention also comprises kits for detection of *H. capsulatum*. Thus, in one aspect the present invention comprises a kit for detection of *H. capsulatum* comprising: (a) one or more containers comprising oligonucleotide primers or DNA probes comprising sequences which hybridize to introns 1 or 2 of the *H. capsulatum* catalase A gene or introns 1, 2 or 3 of the *H. capsulatum* catalase P gene, or any combinations thereof; and (b) at least one separate container comprising *H. capsulatum* DNA comprising catalase A and or catalase P intron DNA individually or in combination. The present invention also comprises a kit for detection of *H. capsulatum* comprising: (a) one or more containers comprising an antibody preparation that recognizes *H. capsulatum* catalase A polypeptide or *H. capsulatum* catalase P polypeptide; and (b) at least one separate container comprising *H. capsulatum* catalase A and or catalase P protein.

The foregoing focuses on the more important features of the invention in order that the detailed description which follows may be better understood and in order that the present contribution to the art may be better appreciated. There are, of course, additional features of the invention which will be described hereinafter and which will form the subject matter of the claims appended hereto. It is to be understood that the invention is not limited in its application to the specific details as set forth in the following description and figures. The invention is capable of other embodiments and of being practiced or carried out in various ways.

From the foregoing summary, it is apparent that an object of the present invention is to provide methods and compositions for detection of *Histoplasma capsulatum* and histoplasmosis. These, together with other objects of the present invention, along with various features of novelty which characterize the invention, are pointed out with particularity in the claims and description provided herein.

BRIEF DESCRIPTION OF THE FIGURES

FIG. 1 shows the nucleotide and protein sequence for a full-length *Histoplasma capsulatum* cDNA clone encoding the catalase A homologue enzyme in accordance with an embodiment of the present invention, wherein the CATA cDNA nucleotide sequence (SEQ ID NO: 1) is shown above the catalase protein sequence (SEQ ID NO: 2), the numbering for each is indicated to the left of their sequences, and the location of two introns are indicated by the vertical arrowheads I1 and I2.

FIG. 2 shows the nucleotide sequence of the *Histoplasma capsulatum* genomic DNA (SEQ ID NO: 3) including the entire CATA transcribed region as well as approximately 1000 bp of 5' UTR (untranscribed region) and 500 bp 3' UTR of the CATA gene in accordance with an embodiment of the present invention. Intron sequences are underlined, the location and orientation of assay primers are indicated in bold italicized lettering with open arrows showing the position and direction of the primers, and transcriptional start and stop sites are indicated using vertical arrowheads.

FIG. 3 shows the nucleotide and deduced protein sequences of a full-length *Histoplasma capsulatum* CATP gene, in accordance with an embodiment of the present invention, wherein the nucleotide sequence (SEQ ID NO: 4) is shown above the catalase P protein sequence (SEQ ID NO: 5) and the numbering for each is indicated to the left of their sequences, and the locations of three introns within the CATP gene in genomic DNA are indicated by arrowheads (I1, I2, and I3).

FIG. 4 shows the nucleotide sequence of the *Histoplasma capsulatum* genomic DNA (SEQ ID NO: 6) including the entire CATP transcribed region as well as approximately 1000 bp of 5' UTR (untranscribed region) and 500 bp 3' UTR of the CATP gene in accordance with an embodiment of the present invention. Intron sequences are underlined, the location and orientation of assay primers are indicated in bold italicized lettering with open arrows showing the position and direction of the primers, and transcriptional start and stop sites are indicated using vertical arrowheads.

FIG. 5 illustrates the sequence of the introns of the CATA and the CATP genes in accordance with an embodiment of the present invention, wherein SEQ ID NO: 7 is the sequence (5' to 3') of intron 1 of the CATA gene, SEQ ID NO: 8 is the sequence of intron 2 of the CATA gene, SEQ ID NO: 9 is the sequence of intron 1 of the CATP gene, SEQ ID NO: 10 is the sequence of intron 2 of the CATP gene, and SEQ ID NO: 11 is the sequence of intron 3 of the CATP gene.

FIG. 6 shows an alignment of the *H. capsulatum* catalase A enzyme (Hc CatA) (SEQ ID NO: 39) with the known protein sequences of the *Aspergillus fumigatus* catalase A (Af catA) (SEQ ID NO: 40), *Emericella (Aspergillus) nidulans* catalase A (En catA) (SEQ ID NO: 41), and *Aspergillus niger* catalase R (An catR) (SEQ ID NO: 42) enzymes, where the sequence of the *H. capsulatum* catalase A protein is predicted by the cDNA sequence given in FIG. 1, and sequences were aligned using BOXSHADE 3.1 on a local server located at www.ch.embnet.org., with exact identities between the three proteins indicated by black shaded boxes, conserved residues indicated by gray boxes, and numbering of the residues for each protein is indicated to the left of the protein sequences.

FIG. 7 illustrates a multiple alignment of the *H. capsulatum* catalase (Hc) P enzyme with other small subunit catalases from *Emericella (Aspergillus) nidulans* (En), *Saccharomyces cerevisiae* (Sc), *Candida albicans* (Ca), *Hansenula polymorpha* (Hp), *S. pombe* (Sp), and using Clustal W and BOXSHADE 3.1 (available on the internet), wherein exact identities between the three proteins are indicated by inclusion of the residues within the black shaded boxes, conserved residues are shaded in gray, and numbering of the residues for each protein is indicated to the left of the protein sequences.

FIG. 9 shows the sequences of the primers used to amplify CATA and CATP introns in accordance with an embodiment of the present invention.

FIG. 10 shows the results of PCR amplification using intron specific primers for *H. capsulatum* catalase A (CATA) (upper panel) and *H. capsulatum* catalase P (CATP) (lower panel) using the primers shown in FIGS. 2 and 4, respectively, in accordance with an embodiment of the present invention.

DETAILED DESCRIPTION

Figure 8A:
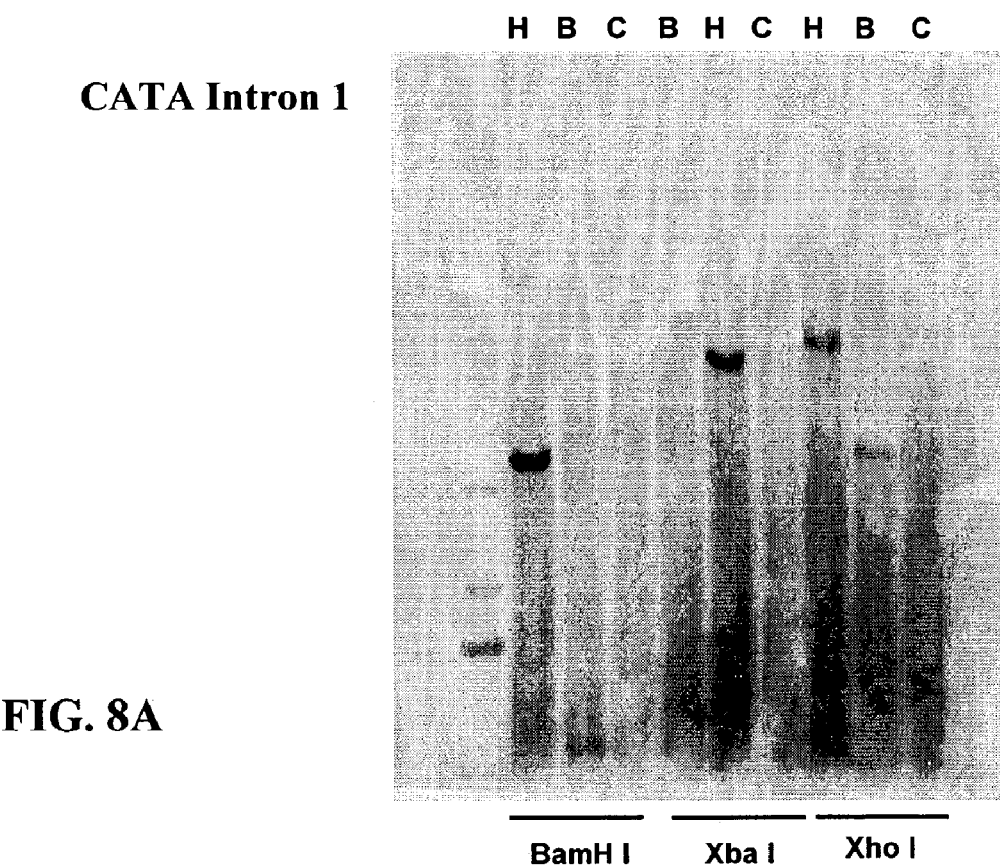
FIG. 8 shows the results of Southern hybridizations of genomic DNA from *H. capsulatum* (H), *B. dermatititis* (B), and *C. neoformans* (C) digested with BamH I, Xba I, and Xho I and probed with radiolabeled PCR products derived either from *H. capsulatum* catalase A (CATA) intron 1 (Panel A) or *H. capsulatum* catalase P (CATP) introns 1 and 2 (top), or CATP intron 3 (bottom) as indicated (Panel B) in accordance with an embodiment of the present invention.

The present invention takes advantage of several unique aspects of *H. capsulatum* biology, and in particular, the biology of the *H. capsulatum* catalase genes. Catalase, which converts hydrogen peroxide to water and oxygen, is a significant component of the *H. capsulatum* response to oxidative stress such as that encountered during macrophage infection (Marchler, G. et al., 1993, *EMBO Journal*, 12:1997–2003, Storz, G., et al., 1992, *J. Nutr.* 122: 627–30; Storz, G., et al., 1990, *Antonie Van Leeuwenhoek*, 58:157–61; Storz, G., et al., 1990, *Science*, 248:189–94; Storz, G., et al., 1990, *Trends Genet.*, 6:363–8).

The present invention relies on the discovery that intron sequences for the *H. capsulatum* catalase A (CATA) and catalase P (CATP) genes comprise highly specific domains, which lack significant identity with counterpart genes in other infectious pathogens and, therefore, can function as specific markers for *H. capsulatum*. These sequences may be useful as reagents for hybridization or polymerase chain reaction (PCR) assays for *H. capsulatum*. For example, it is usually very difficult to distinguish *H. capsulatum* and *Blastornyces dermatititis*. However, using the primers of the present invention, *H. capsulatum* can be distinguished from *B. dermatititis* and other closely related pathogens. Also, the invention provides methods to distinguish patients who have been previously exposed to *H. capsulatum* from those patients who have an active case of histoplasmosis. Furthermore, the present invention describes antibodies to the *H. capsulatum* CATA and CATP proteins.

A. Definitions

In accordance with the present invention, conventional molecular biology, microbiology, and recombinant DNA techniques may be used that will be apparent to those skilled in the relevant art. Such techniques are explained fully in the literature (see, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells And Enzymes" (IRL Press, (1986)); and B. Perbal, "A Practical Guide To Molecular Cloning" (1984)).

Therefore, if appearing herein, the following terms shall have the definitions set out below.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

DNA molecules may be identified by their nucleic acid sequences which are generally presented in the 5' to 3' direction (as the sense strand), wherein 5' and 3' indicate the linkages formed between the 5'-hydroxy group of one nucleotide and the 3'-hydroxyl group of the next. For a sense-strand sequence presented in the 5'-3' direction, its complement (or antisense strand) is the DNA strand which hybridizes to that sequence.

As used herein, the term "gene" shall mean a region of DNA encoding a polypeptide chain.

"Messenger RNA" or "mRNA" shall mean an RNA molecule that encodes for one or more polypeptides.

"DNA polymerase" shall mean an enzyme which catalyzes the polymerization of deoxyribonucleotide triphosphates to make DNA chains using a DNA template.

"Reverse transcriptase" shall mean an enzyme which catalyzes the polymerization of deoxy- or ribonucleotide triphosphates to make DNA or RNA chains using an RNA or DNA template.

"Complementary DNA" or "cDNA" shall mean the DNA molecule synthesized by polymerization of deoxyribonucleotides by an enzyme with reverse transcriptase activity.

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

"Oligonucleotide", as used herein in referring to the probes or primers of the present invention, is defined as a molecule comprised of two or more deoxy- or ribonucleotides, preferably more than ten. Its exact size will depend upon many factors which, in turn, depend upon the ultimate function and use of the oligonucleotide.

"DNA fragment" includes polynucleotides and/or oligonucleotides and refers to a plurality of joined nucleotide units formed from naturally-occurring bases and cyclofuranosyl groups joined by native phosphodiester bonds. This term effectively refers to naturally-occurring species or synthetic species formed from naturally-occurring subunits. "DNA fragment" also refers to purine and pyrimidine groups and moieties which function similarly but which have non naturally-occurring portions. Thus, DNA fragments may have altered sugar moieties or inter-sugar linkages. Exemplary among these are the phosphorothioate and other sulfur containing species. They may also contain altered base units or other modifications, provided that biological activity is retained. DNA fragments may also include species which include at least some modified base forms. Thus, purines and pyrimidines other than those normally found in nature may be so employed. Similarly, modifications on the cyclofuranose portions of the nucleotide subunits may also occur as long as biological function is not eliminated by such modifications.

"Primer" shall refer to an oligonucleotide, whether occurring naturally or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, the source of primer and the method used. For example, for diagnostic applications, depending on the complexity of the target sequence, the oligonucleotide primer typically contains 10–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the term "hybridization" refers generally to a technique wherein denatured RNA or DNA is combined with complementary nucleic acid sequence which is either free in solution or bound to a solid phase. As recognized by one skilled in the art, complete complementarity between the two nucleic acid sequences is not a pre-requisite for hybridization to occur. The technique is ubiquitous in molecular genetics and its use centers around the identification of particular DNA or RNA sequences within complex mixtures of nucleic acids.

As used herein, "restriction endonucleases" and "restriction enzymes" shall refer to bacterial enzymes which cut double-stranded DNA at or near a specific nucleotide sequence.

A polypeptide refers to any peptide generated from a protein either by proteolytic cleavage or chemical cleavage.

B. Detection of Catalase A and Catalase P Intron Sequences

The present invention is directed to nucleic acid sequences that hybridize to the first and second introns of the *H. capsulatum* catalase A gene and the use of these sequences for the detection of *H. capsulatum*.

In one aspect, the present invention comprises an isolated nucleic acid for detection of *H. capsulatum* comprising SEQ ID NO: 7 or the complement of SEQ ID NO: 7, or a fragment of SEQ ID NO: 7 or the complement of SEQ ID NO: 7 that hybridizes under highly stringent conditions to intron 1 of the *H. capsulatum* catalase A gene. Preferably, the isolated nucleic acid fragment comprises at least 8 consecutive nucleotides of SEQ ID NO: 7 or its complement. In an embodiment, the isolated nucleic acid comprises an oligonucleotide having the nucleic acid sequence SEQ ID NO: 12 or SEQ ID NO: 13. In another aspect, the present invention comprises an isolated nucleic acid for detection of *H. capsulatum* comprising SEQ ID NO: 8 or the complement of SEQ ID NO: 8, or a fragment of SEQ ID NO: 8 or the complement of SEQ ID NO: 8 that hybridizes under highly stringent conditions to intron 2 of the *H. capsulatum* catalase A gene. Preferably, the isolated nucleic acid fragment comprises at least 8 consecutive nucleotides of SEQ ID NO: 8. In an embodiment, the isolated nucleic acid comprises an oligonucleotide having the nucleic acid sequence SEQ ID NO: 15 or SEQ ID NO: 16. In another aspect, the present invention comprises an isolated nucleic acid for detection of *H. capsulatum* comprising: (a) the nucleotide sequences set forth in SEQ ID NO: 7 or SEQ ID NO: 8 or any complements thereof; (b) a nucleotide sequence having at least 70% sequence identity to any one of the sequences in (a); and (c) a fragment of any one of (a) or (b).

The highly specific *H. capsulatum* catalase A probes of the present invention can be used for detection of the pathogen in a patient. Thus, in one aspect, the present invention comprises a method for detecting *H. capsulatum* in a sample, comprising the steps of: (a) providing a sample; and (b) assaying for the presence of DNA comprising intron 1 or intron 2 of the *H. capsulatum* catalase A gene (CATA) or a combination of intron 1 and intron 2 of the *H. capsulatum* catalase A gene in the sample, wherein the presence of said CATA intron DNA indicates that the sample contains *H. capsulatum*. In an embodiment, the sample is obtained from a human. Preferably, the method comprises the steps of: (a) exposing the sample under high stringency hybridization conditions to at least one isolated nucleic acid that hybridizes to intron 1 or intron 2 of the *H. capsulatum* catalase A gene (CATA); and (b) determining whether there is hybridization of the isolated nucleic acid to the sample, wherein a sample comprising *H. capsulatum* exhibits detectable hybridization and a sample lacking *H. capsulatum* does not exhibit hybridization. More preferably, the isolated nucleic acid used for hybridization comprises: (a) the nucleotide sequences set forth in SEQ ID NO: 7 or SEQ ID NO: 8 or any complements thereof; (b) a nucleotide sequence having at least 70% sequence identity to any one of the sequences in (a); and (c) a fragment of any one of (a) or (b).

In an embodiment, the method is a PCR based method. Thus, the method may comprise the steps of: (a) conducting polymerase chain reaction (PCR) amplification using at least one nucleic acid primer that hybridizes to intron 1 or intron 2 of the *H. capsulatum* catalase A gene (CATA); and (b) determining the presence or absence of the PCR product resulting from the amplification. More preferably, the PCR primers comprise at least one oligonucleotide having the sequence SEQ ID NO: 12, SEQ ID NO: 13, SEQ ID NO: 15, or SEQ ID NO: 16. Also more preferably, the conditions for PCR amplification are chosen so that the PCR product of interest is generated in samples comprising *H. capsulatum* but not in samples that do not contain *H. capsulatum*.

The invention also utilizes unique aspects of *H. capsulatum* catalase P biology. Thus, the present invention describes nucleic acid sequences derived from introns 1, 2, or 3 of the catalase P gene to detect *H. capsulatum*, and the use of such sequences to distinguish *H. capsulatum* from closely related pathogens. Thus, in one aspect, the present invention comprises an isolated nucleic acid for detection of *H. capsulatum* comprising SEQ ID NO: 9 or the complement of SEQ ID NO: 9, or a fragment of SEQ ID NO: 9 or the complement of SEQ ID NO: 9 that hybridizes under highly stringent conditions to intron 1 of the *H. capsulatum* catalase P gene. Preferably, the isolated nucleic acid fragment comprises at least 8 consecutive nucleotides of SEQ ID NO: 9 or its complement. In an embodiment, the isolated nucleic acid comprises an oligonucleotide having the nucleic acid sequence SEQ ID NO: 18 or SEQ ID NO: 19. In another aspect, the present invention comprises an isolated nucleic acid for detection of *H. capsulatum* comprising SEQ ID NO: 10 or the complement of SEQ ID NO: 10, or a fragment of SEQ ID NO: 10 or the complement of SEQ ID NO: 10 that hybridizes under highly stringent conditions to intron 2 of the *H. capsulatum* catalase P gene. Preferably, the isolated nucleic acid fragment comprises at least 8 consecutive nucleotides of SEQ ID NO: 10 or its complement. In an embodiment, the isolated nucleic acid comprises an oligonucleotide having the nucleic acid sequence SEQ ID NO: 20 or SEQ ID NO: 23. In yet another aspect, the present invention comprises an isolated nucleic acid for detection of *H. capsulatum* comprising SEQ ID NO: 11 or the complement of SEQ ID NO: 11, or a fragment of SEQ ID NO: 11 or the complement of SEQ ID NO: 11 that hybridizes under highly stringent conditions to intron 3 of the *H. capsulatum* catalase P gene. Preferably, the isolated nucleic acid fragment comprises at least 8 consecutive nucleotides of SEQ ID NO: 11 or its complement. In an embodiment, the isolated nucleic acid comprises an oligonucleotide having the nucleic acid sequence SEQ ID NO: 21 or SEQ ID NO: 22. In yet another aspect, the present invention comprises an isolated nucleic acid for detection of *H. capsulatum* comprising: (a) the nucleotide sequences set forth in SEQ ID NO: 9, SEQ ID NO: 10, or SEQ ID NO: 11, or any complements thereof; (b) a nucleotide sequence having at least 70% sequence identity to any one of the sequences in (a); and (c) a fragment of any one of (a) or (b).

The invention also employs catalase P sequences for the specific detection of *H. capsulatum* exposure in a patient or patient population. Thus, in another aspect, the present invention comprises a method for detecting *H. capsulatum* in a sample, comprising the steps of: (a) providing a sample; and (b) assaying for the presence of DNA comprising intron 1, intron 2, or intron 3 of the *H. capsulatum* catalase P gene (CATP) or a combination thereof in said sample, wherein the presence of said CATP intron DNA indicates that the sample contains *H. capsulatum*. In an embodiment, the sample is obtained from a human. Preferably, the method is a hybridization method. In an embodiment, the method comprises the steps of (a) exposing the sample to at least one isolated nucleic acid that hybridizes to intron 1, intron 2, or intron 3 of the *H. capsulatum* catalase P gene (CATP); and (b) determining whether there is hybridization of the isolated nucleic acid to the sample, wherein a sample comprising *H. capsulatum* exhibits detectable hybridization. More preferably, the isolated nucleic acid used for hybridization comprises: (a) the nucleotide sequences set forth in SEQ ID NO: 9, SEQ ID NO: 10, or SEQ ID NO: 11, or any complements thereof; (b) a nucleotide sequence having at least 70% sequence identity to any one of the sequences in (a); and (c) a fragment of any one of (a) or (b). Also preferably, the method comprises a PCR-based assay. In an embodiment, the method comprises the steps of (a) conducting polymerase chain reaction (PCR) amplification using at least one nucleic acid primer that hybridizes to intron 1, intron 2, or intron 3 of the *H. capsulatum* catalase P gene (CATP); and (b) determining the presence or absence of the PCR product resulting from the amplification. More preferably, the primers comprise at least one oligonucleotide having the sequence SEQ ID NO: 18, SEQ ID NO: 19, SEQ ID NO: 20, SEQ ID NO: 21, SEQ ID NO: 22 or SEQ ID NO: 23. Also more preferably, the conditions for PCR amplification are chosen so that the PCR product of interest is generated in samples comprising *H. capsulatum* but a PCR product is not generated in samples that do not contain *H. capsulatum*.

The present invention also comprises a kit for detection of *H. capsulatum* using hybridization probes and/or PCR primers. Thus, in another aspect, the present invention comprises a kit for detecting *H. capsulatum* comprising (a) one or more containers comprising oligonucleotide primers or DNA probes comprising sequences which hybridize to introns 1 or 2 of the *H. capsulatum* catalase A gene or introns 1, 2 or 3 of the *H. capsulatum* catalase P gene, or any combinations thereof; and (b) at least one separate container comprising *H. capsulatum* DNA comprising catalase A and or catalase P intron DNA individually or in combination.

Thus, the present invention describes the use of introns from the *H. capsulatum* catalase A (CATA) and catalase P (CATP) genes for detection of *H. capsulatum*. The sequences of the cDNA and genomic DNA sequences for the *H. capsulatum* catalase A and catalase P genes are shown in FIGS. 1–4. The presence and locations of introns within the coding regions of the *H. capsulatum* CATA and CATP genes has been determined by automated DNA sequencing of *H. capsulatum* genomic DNA clones (Johnson et al., 2002, Microbiology, in press). The sequence of the *H. capsulatum* catalase A cDNA and genomic DNA are shown in FIGS. 1 and 2, respectively. The coding region of the CATA gene is interrupted by 2 introns, I1 and I2, which are 84 and 73 bp, respectively. The sequence of the CATA introns 1 and 2 are shown in FIG. 5 as SEQ ID NO: 7 and SEQ ID NO: 8, respectively.

The present invention also comprises isolated nucleic acids that hybridize under highly stringent conditions to introns of the CATP gene. The sequence of the *H. capsulatum* catalase P cDNA and genomic DNA are shown in FIGS. 3 and 4, respectively. The coding region of the CATP gene is interrupted by 3 introns, I1, I2 and I3, which are 137 bp, 136 bp, and 98 bp in length, respectively. The sequence of the CATP introns 1, 2 and 3 are also shown in FIG. 5 as SEQ ID NO: 9, SEQ ID NO: 10 and SEQ ID NO: 11, respectively.

There is a high level of homology for the coding region of proteins from *H. capsulatum* as compared to proteins from other fungi. The high homology found between *H. capsulatum* catalase A and catalase P proteins and catalase homologues found in other fungi is shown in FIGS. 6 and 7, respectively. In contrast to the conservation seen in coding regions, the nucleotide sequence for the catalase introns are not highly conserved among related fungi (Johnson et al., *Microbioogy,* 2002, in press). Thus, intron sequences provide a unique tool by which to identify the presence of *H. capsulatum* DNA in a sample.

In an embodiment, the intron sequences (FIG. 5) are used as hybridization probes. Because of the high specificity of *H. capsulatum* intron sequences, the present invention comprises a method to distinguish *H. capsulatum* from other fungal pathogens, or combinations of other fungal pathogens such as, but not limited to, *Blastomyces dermatititis, Aspergillus nidulans, Aspergillus fumigates, Emericella nidulans, Neurospora crassa, Cryptococcus neoformans, Candida albicans,* and *Coccidioides immitis*. Preferably, there is little to no cross-reactivity with DNA from other organisms. For example, in an embodiment, intron probes from *H. capsulatum* catalase A detect DNA from *H. capsulatum* but not from *B. dermatitis* or *C. neoformans* (FIG. 8).

Thus, the invention comprises a method for detecting *H. capsulatum* in a patient, comprising the step of detecting nucleic acid sequences comprising intron 1 of the *H. capsulatum* catalase A gene, or intron 2 of the *H. capsulatum* catalase A gene, or a combination of intron 1 and intron 2 of the *H. capsulatum* catalase A gene. For example, the method may include the steps of (a) obtaining a sample from a patient; (b) exposing the sample under high stringency hybridization conditions to at least one isolated nucleic acid that hybridizes to intron 1 or intron 2, or both introns 1 and 2 of the *H. capsulatum* catalase A gene; (c) determining whether there is hybridization of the isolated nucleic acid to the patient sample; and (d) assessing the presence of *H. capsulatum* DNA in the sample, wherein a sample comprising *H. capsulatum* DNA will exhibit detectable hybridization and a sample lacking *H. capsulatum* DNA will not exhibit hybridization (FIG. 8A). Alternatively, the present invention also comprises a method for detecting *H. capsulatum* in a patient, comprising the step of detecting nucleic acid sequences comprising intron 1, intron 2, intron 3, or a combination thereof from the *H. capsulatum* catalase P gene (FIG. 8B).

Hybridizations may be performed according to standard methods. *H. capsulatum* genomic DNA may be isolated by methods known to those in the art such as the protocols described by Woods et al., (Woods, J. P., et al., 1992, *Molecular Microbiology,* 6: 3603–10). DNA may be denatured and spotted on membranes or digested with restriction enzymes and electrophoresed in agarose gels for transfer by capillary blotting to a solid support (e.g. Hybond-N membrane; Amersham Pharmacia Biotech, Inc.) and hybridized to probes. For dot blotting (slot blotting) DNA is denatured and spotted onto a solid support membrane.

Hybridization conditions can be described as ranging from low to high stringency. Generally, highly stringent conditions refer to washing hybrids in low salt buffer at high temperatures. Hybridization may be to filter bound DNA using hybridization solutions standard in the art such as 0.5M $NaHPO_4$, 7% sodium dodecyl sulfate (SDS), at 65° C., and washing in 0.25 M $NaHPO_4$, 3.5% SDS followed by washing 0.1×SSC/0.1% SDS at a temperature ranging from room temperature to 68° C. depending on the length of the probe (see e.g. Ausubel, F. M. et al., *Short Protocols in Molecular Biology,* $4^{th}$ Ed., Chapter 2, John Wiley & Sons, N.Y). For example, a high stringency wash comprises washing in 6×SSC/0.05% sodium pyrophosphate at 37° C. for a 14 base oligonucleotide, or at 48° C. for a 17 base oligonucleotide, or at 55° C. for a 20 base oligonucleotide, or at 60° C. for a 25 base oligonucleotide, or at 65° C. for a nucleotide probe about 250 nucleotides in length such as SEQ ID NO: 10. Nucleic acid probes may be labeled with radionucleotides by end-labeling with, for example, [$\gamma$-$^{32}$P] ATP, or incorporation of radiolabeled nucleotides such as [$\alpha$-$^{32}$P]dCTP by random primer labeling. Alternatively, probes may be labeled by incorporation of biotinylated or fluorescein labeled nucleotides, and the probe detected using antibodies to the label.

Intron sequences may also be used as primers for PCR amplification of intervening *H. capsulatum* genomic DNA. In one embodiment, the CATA intron sequences are amplified using intron specific primers (FIG. 9; see also FIG. 2, wherein primer sequences are shown in bold, with open arrows indicating the 5'-3' direction for the primer). Thus, primer Aassay5'-1 (5'-tgcgggcaacatatgataac-3') (SEQ ID NO: 12) and Aassay5'-2 (5'-gataaccatcgagttagatcc-3') (SEQ ID NO: 13) hybridize to CATA intron 1, whereas primer Aassay5'-3 (5'-cgtccgctggtgttctaac-3') (SEQ ID NO: 14) hybridizes to exon 2. Primer Aassay3'-1 (5'cgatcaacacgaaaatatcc-3') (SEQ ID NO: 15) and Aassay3'-2 (5'-tatcaatcaatacttac-3') (SEQ ID NO: 16) both hybridize to CATA intron 2, whereas primer Aassay3'-3 (5'-gacatcacggactgtatcg-3') (SEQ ID NO: 17) hybridizes to exon 2 (FIG. 2). Thus, in an embodiment, and referring now to FIG. 10, amplification with primers comprising CATA intron sequences results in detection of products from *H. capsulatum* DNA, but not from *B. dermatititis* and *C. neoformans.* Interestingly, using primer Aassay3'-3 from *H. capsulatum* CATA exon 2, there is significant cross-reactivity with *B. dermatititis* DNA, indicating that at the exon level, the catalases from these two organisms are similar, whereas intron sequences provide a means to distinguish the two organisms.

In an embodiment, the CATP intron sequences are amplified using intron specific primers (FIGS. 9 and 10; see also FIG. 4, wherein primer sequences are shown in bold, with arrows indicating the 5'-3' direction for the primer). Thus, primer Passay5'-1 (5'-gagcttcgatacttaatctag-3') (SEQ ID NO: 18) and Passay5'-2 (5'-gacggacgtgtctaaaacg-3') (SEQ ID NO: 19) hybridize to CATP intron 1. Primer Passay5'-3 (5'-gctatcattagagaacagatc-3') (SEQ ID NO: 20) and Passay3'-3 (5'-gatctagtggggacaatacg-3') (SEQ ID NO: 23) hybridize to CATP intron 2, and primer Passay3'-1 (5'-cagggttctgggtatgtct-3') (SEQ ID NO: 21) and Passay3'-2 (5'-gtgccgcagctgatggttg-3') (SEQ ID NO: 22) hybridize to CATP intron 3. Thus, in an embodiment, amplification with primers comprising CATP intron sequences results in detection of products from *H. capsulatum* DNA, but not from *B. dermatititis* and *C. neoformans* (FIG. 10).

Techniques for detection of amplified sequences include gel electrophoresis of the amplified DNA and visualization of the amplified product by ethidium bromide staining. Alternatively, the amplified DNA may be labeled by incorporation of oligonucleotide primers, which have been radiolabeled and products visualized by comparison to radiolabeled size markers by gel electrophoresis. Finally, unlabeled PCR products may be separated by gel electrophoresis, transferred to a solid matrix and products identified by hybridization of a radiolabeled probe which recognizes (i e. is homologous to) the amplified DNA.

The amplified DNA may also be labeled by incorporation of oligonucleotide primers which have been end-labeled with a detectable chemical moiety such as, for example, biotin or fluorescein, or by incorporation of nucleotides labeled with a detectable chemical moiety such as, for example, fluorescein-dUTP, and the like. The chemically labeled products are then detected using reagents specific for that moiety. For example, PCR may be performed using primers comprising biotinylated primers specific to intron sequences from *H. capsulatum* CATA or CATP. The amplified DNA may then be blotted to a solid support, and detected using streptavidin labeled IgG and a secondary anti-IgG antibody labeled with an enzyme, such as alkaline phosphatase, which comprises a colorimetric reaction product. Thus, the presence of the colored product provides a quantitative assay for the presence of *H. capsulatum* CATA or CATP DNA.

In another embodiment, the nucleic acid that hybridizes to CATA or CATP intron DNA is arranged as a microchip or an array. In this manner, hybridization of CATA or CATP specific PCR products may be detected by hybridization of the PCR product to the array, as for example by labeling the PCR product with a moiety which comprises an electrochemical, luminescent or fluorescent signal.

In yet another embodiment, the method comprises using real-time PCR wherein the PCR product is detected by the use of fluorescent dyes to detect the biosynthesis of products (Leutenegger, C. M., et al., 2001, *AIDS Res. Hum. Retroviruses*, 17: 243–251, Nadkarni, M. A., et al., 2002, *Microbiology*, 148: 257–266; S. J. Wall and D. R. Edwards, 2002, *Anal., Biochem.*, 300: 269–273). Real-time PCR uses incorporation of a fluorescent label as a means to monitor the amplification of PCR product via fluorescence resonance energy transfer (FRET). Commercially available thermocyclers and probes are the LightCycler and probes from Roche Applied Science, the SmartCycler from Cepheid (Sunnyvale, Calif.), the GeneAmp 5700 and Prism 7700 cyclers from Applied Biosystems (Foster City, Calif.), the iCycler iQ from BioRad (Hercules, Calif.) and probes from Molecular beacons (available on the internet) (Cockerill, F. R., et al. 2002, *ASM News*, 68: 77–83). The methodology is adaptable to both PCR and RT-PCR techniques, and in many cases, results are obtained in less than 1 hour.

C. Use of Intron Sequences to Distinguish *H. capsulatum* from Closely Related Pathogens The present invention also provides reagents which allow for distinguishing *H. capsulatum* from closely related pathogens such as *Blastomyces dermatitis, Aspergillus nidulans, Aspergillus fumigatus, Neurospora crassa, Cryptococcus neoformans, Candida albicans* and *Coccidioides immitis*. The assay may comprise the unique catalase A or P intron sequences as reagents in either a hybridization assay or a PCR assay. Thus, in one aspect the present invention comprises a method for distinguishing whether a subject has been exposed to *H. capsulatum* or at least one second pathogen comprising: (a) obtaining a sample from a subject; (b) exposing the sample under high stringency hybridization conditions to at least one isolated nucleic acid that hybridizes to at least one intron from the *H. capsulatum* catalase A or catalase P genes; (c) exposing the sample under high stringency hybridization conditions to at least one isolated nucleic acid that hybridizes to sequences from a second pathogen; (d) determining whether there is hybridization of the *H. capsulatum* catalase A or catalase P intron sequences to the sample; (e) determining whether there is hybridization of the sequences from the second pathogen to the sample; (f) assessing the presence of *H. capsulatum* in the sample, wherein a sample comprising *H. capsulatum* exhibits detectable hybridization to the *H. capsulatum* catalase A or catalase P intron sequences and a sample lacking *H. capsulatum* does not exhibit hybridization; and (g) assessing the presence of the second pathogen in the sample, wherein a sample comprising the second pathogen exhibits detectable hybridization to the sequences derived from the second pathogen and a sample lacking the second pathogen does not exhibit hybridization.

In an embodiment, the assay distinguishes *H. capsulatum* from *Blastomyces dermatitis*. In another embodiment, the assay distinguishes *H. capsulatum* from *Aspergillus nidulans, Aspergillus fumigatus, Emericella nidulans, Neurospora crassa, Cryptococcus neoformans, Candida albicans, Coccidioides immitis* or combinations thereof.

In an embodiment, the method further comprises a PCR based assay comprising the steps of: (a) performing PCR using at least one isolated oligonucleotide which specifically hybridizes to intron 1, intron 2, or intron 3 of the *H. capsulatum* catalase P gene or intron 1 or intron 2 of the *H. capsulatum* catalase A gene under conditions such that a predetermined PCR product is generated in samples comprising *H. capsulatum* but not in samples that do not contain *H. capsulatum* and determining the presence or absence of the PCR product; and (b) performing PCR using least one isolated oligonucleotide which specifically hybridizes to DNA from the second pathogen under conditions such that a second predetermined PCR product is generated in samples comprising the second pathogen but not in samples that do not contain the second pathogen and determining the presence or absence of the PCR product. Thus, the formation of a PCR product indicates that hybridization occurred between the intron probe and the target DNA.

In an embodiment, the assay distinguishes *H. capsulatum* from *Blastomyces dermatitis*. In another embodiment, the assay distinguishes *H. capsulatum* from *Aspergillus nidulans, Aspergillus fumigates, Emericella nidulans, Neurospora crassa, Cryptococcus neoformans, Candida albicans, Coccidioides immitis* or combinations thereof.

D. Catalase A and P Polypeptides for Detection of *H. capsulatum*

The present invention also employs *H. capsulatum* catalase A polypeptide sequences and/or *H. capsulatum* catalase P polypeptide sequences for detection of *H. capsulatum*. Thus, in another aspect, the present invention comprises a method for detecting *H. capsulatum* in a sample, comprising the steps of: (a) providing a sample; and (b) assaying for the presence *H. capsulatum* catalase P polypeptide or *H. capsulatum* catalase A polypeptide in said sample, wherein a sample comprising *H. capsulatum* catalase P or catalase A polypeptide contains *H. capsulatum*. In an embodiment, the method includes the steps of: (a) preparing the sample for immunoassay; (b) conducting an immunoassay with an antibody preparation which specifically recognizes *H. capsulatum* catalase P polypeptide or catalase A polypeptide to form an immune complex; (c) detecting the presence or absence of the immune complex; and (d) determining exposure to *H. capsulatum*, wherein the immune complex comprising the *H. capsulatum* catalase P polypeptide or the *H. capsulatum* catalase A polypeptide is detected in samples have been infected with *H. capsulatum* but not in samples who have not been infected with *H. capsulatum*. In an embodiment, the sample is from a human subject.

Figure 12:
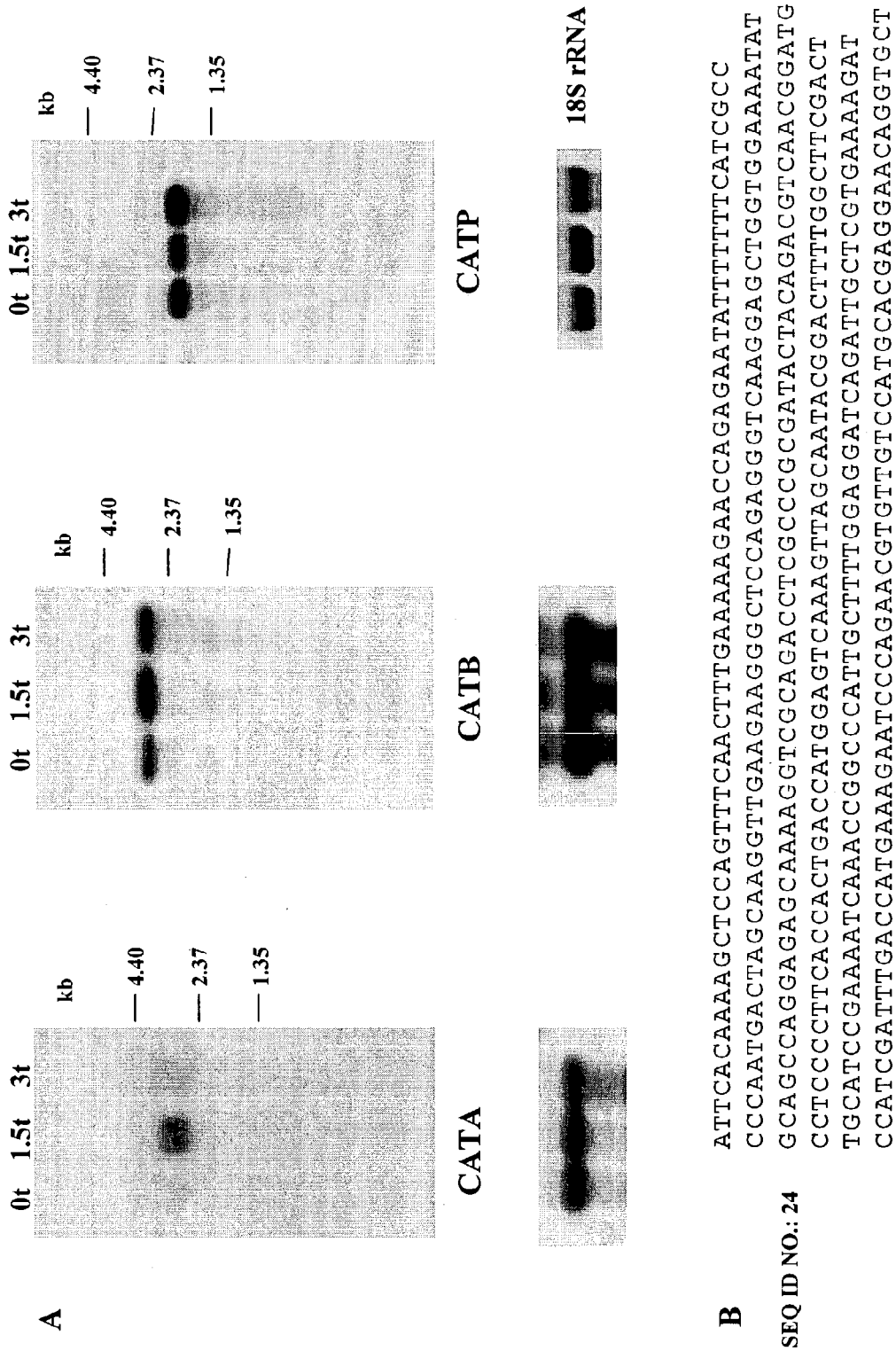
FIG. 12 illustrates expression of catalases in accordance with an embodiment of the present invention, wherein panel A shows the *Histoplasma capsulatum* catalase A (CATA), catalase B (CATB), and catalase P (CATP) genes after challenge with $H_2O_2$ for the times indicated above each lane (in hours) as shown by Northern analysis using CATA, CATB, or CATP probes as indicated below each blot, and panel B shows the 5' end of the CATA gene which is detected upon $H_2O_2$ induction (SEQ ID NO: 24).

Also, in another aspect, the present invention comprises a kit for detection of *H. capsulatum* via detection of catalase A and P polypeptides. Thus, in yet another aspect, the present invention comprises a kit for *H. capsulatum* detection comprising: (a) one or more containers comprising an antibody preparation that recognizes *H. capsulatum* catalase A polypeptide or *H. capsulatum* catalase P polypeptide; and (b) at least one separate container comprising *H. capsulatum* catalase A and or catalase P protein.

The present invention also provides an immunoassay for distinguishing *H. capsulatum* from closely related pathogens such as *C. neoformans, A. nidulans,* and *A. niger*. Thus, in another aspect, the present invention comprises a method for distinguishing whether a subject has been exposed to *H. capsulatum* or at least one second pathogen comprising the steps of: (a) obtaining a sample from the subject; (b) preparing the sample for immunoassay; (c) conducting an immunoassay with an antibody preparation which specifically recognizes *H. capsulatum* catalase P or catalase A polypeptide; (d) conducting an immunoassay with an antibody preparation which specifically recognizes at least one polypeptide from the second pathogen; (e) detecting the presence or absence of an immune complex in steps (c) and (d); and (f) determining exposure to *H. capsulatum* or the second pathogen, wherein an immune complex comprising *H. capsulatum* catalase P polypeptide or catalase A polypeptide is detected in subjects who have been infected with *H. capsulatum,* and wherein an immune complex comprising polypeptides from the second pathogen is detected in subjects who have been infected with the second pathogen. In an embodiment, and referring now to FIG. 11, the assay distinguishes patients who have been exposed to *H. capsulatum* from patients who have been exposed to *Cryptococcus neoformans* (Cn), *Asperfillus nidulans* (Ani), and *Aspergillus niger* (Ang). In another embodiment, the assay distinguishes patients who have been exposed to *H. capsulatum* from patients who have been exposed to *Aspergillus fumigates, Emericella nidulans, Neurospora crassa, Coccidioides immitis* or combinations thereof.

As described herein, the formation of an immune complex involves allowing catalase A or catalase P polypeptides to interact with a binding partner and then measuring the formation, or lack of formation, of such a complex. For example, antibodies to catalase A or catalase P polypeptides may be used to complex the polypeptide as an antigen-antibody complex. Complex formation may be measured in solution, or by allowing the complex to bind to a solid surface. In this aspect, catalase A and catalase P proteins may be identified and quantified by methods known in the art such as, but not limited to, staining of thin sections, immunoblot analysis, sandwich assays, solution enzyme-linked immunoassay (ELISA), radioimmunoassay (RIA), and the like.

As used herein, a carrier, solid surface, or solid phase support is a surface which is capable of immobilizing cells, cell particles or soluble proteins. The support can be washed with suitable buffers to remove non-bound components, and can be incubated with protein solutions to block non-specific binding sites. Well-known solid phase supports include glass, polypropylene, dextran, nylon, modified celluloses, polyacrylamides, and the like. Included as solid surfaces for binding reactions are microtiter wells, filter arrays, beads, dip-sticks and other suitable agents for binding assays.

Both catalase A and catalase P may be detected by immunoblotting. Immunoblotting generally comprises separation of proteins primarily by molecular weight by sodium dodecyl sulfate polyacrylamide gel electrophoresis (SDS-PAGE) and transfer of the separated proteins to a membrane. Proteins of interest can then be detected by exposing the membrane to an antibody to the protein(s), and detecting the formation of immune complexes by methods standard in the art. For example, an assay suitable for the methods of the present invention is the enzyme linked immunoassay (ELISA or EIA) where an enzyme bound to an antibody reacts with a chromogenic substrate to produce a product which can be detected, as for example by spectroscopic, fluorometric, or visual means. Enzymes which can be used to label the antibody for production of a detectable signal include alkaline phosphatase, horseradish peroxidase, glucose oxidase, catalase, glucose-6-phosphate dehydrogenases, and the like.

Alternatively, binding may be measured using microtiter wells or other types of reaction vessels. For example, microtiter wells may be pre-coated with antibody to *H. capsulatum* catalase A or catalase P and a mixture comprising radiolabeled *H. capsulatum* catalase A (or catalase P, respectively) and a homogenate from the sample of interest added. In this approach, binding of radiolabeled catalase A (or catalase P) to the microtiter wells is displaced in a quantitative manner by increasing amounts of catalase A or catalase P in the sample.

Antibodies may be commercially available or may be prepared by methods standard in the art. Thus, antibodies may include, but are not limited to, polyclonal antibodies, monoclonal antibodies (mAbs), single chain antibodies, Fab fragments, chimeric antibodies, epitope-binding fragments and the like. For example, polyclonal antibodies are a heterogeneous population of antibody molecules derived from the sera of animals immunized with the antigen of interest. Adjuvants such as Freund's (complete and incomplete), peptides, oil emulsions, lysolecithin, polyols, polyanions and the like may be used to increase the immune response.

Monoclonal antibodies are homogeneous populations of antibodies to a particular antigen, and are generally obtained by any technique which provides for production of antibody by continuous cell lines in culture. Monoclonal antibodies may be humanized, to thereby reduce interaction with unrelated epitopes by the technique of single chain antibodies (see e.g. U.S. Pat. No. 4,946,777 and Bird, *Science* 242: 423–426 (1988)).

E. Detection of Histoplasmosis

Only a small percentage of people with antibodies to *H. capsulatum* actually have an active case of histoplasmosis. In some cases, however, histoplasmosis can be fatal. Thus, it is important to develop a method to determine whether a patient who has been exposed to *H. capsulatum* actually has an active case of histoplasmosis. Patients having an active case of histoplasmosis mount a cellular defense against the pathogen, which includes the production of increased levels of peroxides and other oxidative agents. The *H. capsulatum* catalases, which convert hydrogen peroxide to water and oxygen, contribute to the ability of the pathogen to tolerate environmental and host-induced oxidative stress tolerance.

Thus, the present invention also comprises methods to distinguish a latent *H. capsulatum* infection from active histoplasmosis. In this aspect, the present invention relies on the discovery that expression of the *H. capsulatum* catalase A is markedly increased by oxidative stress. Thus, in an embodiment, detecting increased *H. capsulatum* catalase A gene activity enables detection of organisms that are actively combating the body's defense mechanisms. For example, Northern analysis using different cDNA probes show that the *H. capsulatum* catalase genes (CATA, CATB, and CATP)

are differentially expressed during yeast phase growth. While the CATB and CATP genes are constitutively expressed during yeast phase growth, the expression of the CATA gene is significantly upregulated only after the pathogen experiences an oxidative stress (FIG. 12A).

The present invention also relies on the discovery that full-length CATA transcripts are preferentially detected upon induction with $H_2O_2$, and that in non-induced cultures, only transcripts which are missing the 5'-end are detected. Thus, the difficulty in isolating full length CATA clones from *H. capsulatum* libraries which have not been induced by oxidative stress indicates that even if present, the CATA transcripts may not be translated (Johnson et al, Microbiology, 2002, in press).

Figure 13:
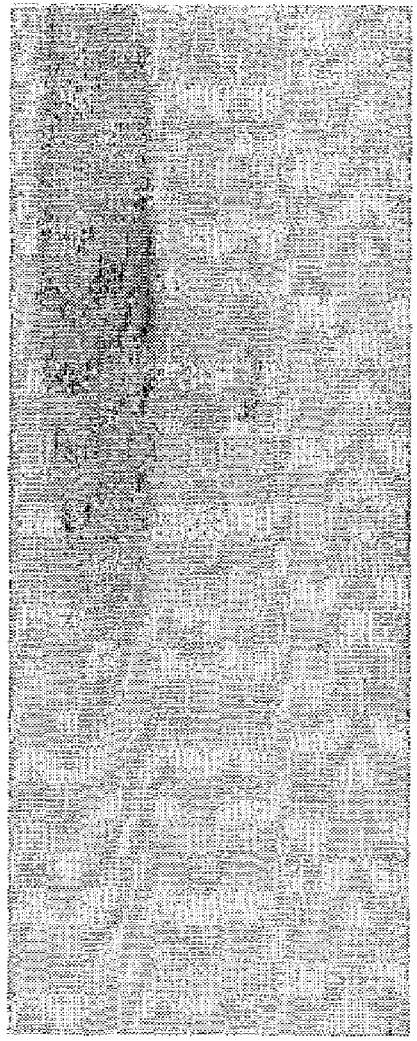
FIG. 13 illustrates a Western blot of fractions from a lysate of *H. capsulatum* yeast culture induced with 30 mM $H_2O_2$ in accordance with an embodiment of the present invention.
Figure 14:
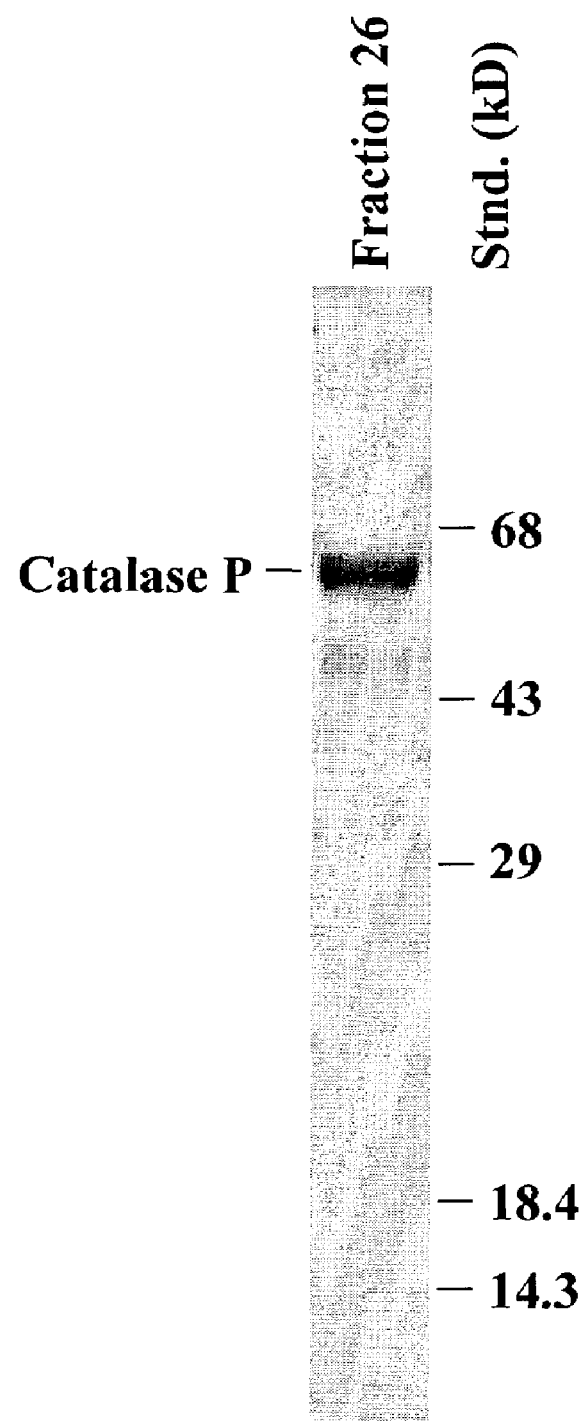
FIG. 14 shows catalase P eluted from a hydroxyapatite column in accordance with an embodiment of the present invention.

In another aspect, the present invention includes a method for detecting an active case of histoplasmosis in a patient, comprising detecting the presence of *H. capsulatum* catalase A polypeptide (FIG. 13). Thus, in one aspect, the present invention comprises a method for detecting an active case of histoplasmosis in a subject, comprising the steps of: (a) providing a sample from a subject; and (b) assaying for the presence *H. capsulatum* catalase A (CATA) polypeptide in said sample, wherein detection of *H. capsulatum* catalase A polypeptide is associated with an active case of histoplasmosis. In an embodiment, the method also includes the step of assaying for the presence *H. capsulatum* catalase P (CATP) polypeptide in said sample. Preferably, the method includes the steps of (a) preparing the sample for immunoassay; (b) conducting the immunoassay with an antibody preparation which specifically recognizes *H. capsulatum* catalase A polypeptide to form an immune complex; (c) detecting the presence or absence of the immune complex; and (d) determining whether the subject has an active case of histoplasmosis, wherein detection of the immune complex is associated with an active case of histoplasmosis. In an embodiment, the sample is obtained from a human.

The present invention also includes a method for detecting an active case of histoplasmosis in a patient comprising detecting the presence of *H. capsulatum* catalase A mRNA or any fragments thereof. Thus, in one aspect, the present invention comprises a method for detecting an active case of histoplasmosis in a sample, comprising the steps of: (a) providing a sample; and (b) assaying the sample for the presence of *H. capsulatum* catalase A mRNA or any fragment thereof wherein detection of *H. capsulatum* catalase A mRNA is associated with an active case of histoplasmosis.

In an embodiment, the method may be a hybridization based assay. Thus, the method may include the steps of: (a) exposing the sample under high stringency conditions to at least one isolated nucleic acid that hybridizes to *H. capsulatum* catalase A mRNA or any fragment thereof; and (b) determining the levels of *H. capsulatum* catalase A mRNA based on the amount of hybridization. Preferably, the nucleic acid probe hybridizes to the nucleotide sequences set forth in SEQ ID NO: 24 or any fragment thereof.

In an embodiment, the method may be a PCR based assay. Thus, in an embodiment, the method includes the steps of: (a) preparing *H. capsulatum* catalase A cDNA using mRNA from the sample as a template; (b) conducting PCR using primers that hybridize to the *H. capsulatum* catalase A cDNA; and (c) ascertaining the presence or absence of product, wherein detection of the amplification product is associated with an active case of histoplasmosis. Preferably, the PCR primers hybridize to the 5' most sequences of the *H. capsulatum* catalase A gene comprising the sequence set forth in SEQ ID NO:24 or any fragment thereof (FIG. 12B).

In yet another aspect, the present invention comprises a composition for the specific detection of an active case of histoplasmosis in a subject comprising an isolated nucleic acid that hybridizes to the 5' most sequences of the *H. capsulatum* catalase A gene comprising the sequence set forth in SEQ ID NO:24.

In an embodiment, the present invention comprises the use of *H. capsulatum* catalase P reagents and catalase A reagents in a sequential assay, wherein the presence of *H. capsulatum* in a sample is determined by the detection of *H. capsulatum* catalase P introns or polypeptide, and a diagnosis of histoplasmosis is determined by the detection of *H. capsulatum* catalase A introns or polypeptide. For example, in one aspect, the present invention comprises a method for the diagnosis of histoplasmosis in a subject, comprising the steps of: (a) assaying for the presence of *H. capsulatum* catalase P polypeptide in a sample obtained from the subject; (b) if *H. capsulatum* catalase P polypeptide is detected, assaying for the presence of *H. capsulatum* catalase A polypeptide in the sample; and (c) determining whether the patient has histoplasmosis, wherein the presence of both *H. capsulatum* catalase P polypeptide and catalase A polypeptide indicates a diagnosis of histoplasmosis. In this embodiment, the present invention takes advantage of the finding that CATP is constitutively expressed, whereas CATA is expressed in response to oxidative stress (FIG. 12A).

Alternatively, the assay may employ hybridization or PCR screening for CATP (or CATA) intron sequences to detect the presence of *H. capsulatum* genomic DNA followed by an RNA based screening for the detection of CATA transcripts. For example, in an embodiment, the method may employ nucleic acid probes which are specific to the 5' end of the *H. capsulatum* catalase A gene for detection of CATA transcripts. For example, RNA from a patient can be hybridized under highly stringent conditions to an isolated nucleic acid comprising the 5' region of CATA mRNA. In an embodiment, the isolated nucleic acid hybridizes to SEQ ID NO: 24, or any fragments thereof. The presence of CATA transcripts can then be measured by the detection of hybrids using standard blotting methods or by amplification of the hybrids using PCR.

For RNA based assays, total RNA may be used. For example, total RNA may be extracted from cultures of *H. capsulatum* yeast or mycelia according to a modification of the acid guanidinium thiocyanate extraction procedure of Chomczynski & Sacchi (1987) and treated using RNase-free reagents as known to those of skill in the art. For certain applications, mRNA is used as a template to generate CATA (or CATP) cDNA. For example, for quantitation of mRNA by RT-PCR, total or poly-$A^+$ RNA is reverse transcribed using oligo-dT primers, wherein dT is defined as deoxythymidylate. For increased specificity, the primer may be designed with 3' end which specifically hybridizes to CATA mRNA. In yet another embodiment, real-time PCR employing either total RNA or mRNA may be used.

F. Purification of Catalase P

The redundancy of catalase genes in *H. capsulatum* indicates that these genes play a role in fungal virulence. As the peroxisomal catalase, and thus the catalase primarily responsible for the majority of peroxide decomposition, catalase P presents a target for therapeutic reagents designed to reduce pathogenicity of *H. capsulatum*. Thus, the present invention also provides a method for the purification of cytosolic catalase enzymes, such as *H. capsulatum* catalase P, comprising the steps of: (a) preparing a clarified cellular supernatant from a sample; (b) applying the clarified cellular supernatant to a sepharose column; and (c) eluting proteins from the column with a decreasing concentration of ammonium sulfate/sodium phosphate buffer, wherein fractions comprising catalase are capable of degrading hydrogen peroxide. In an embodiment, step (a) further comprises the substeps of: (i) using mechanical means to lyse cells comprising the catalase of interest; (ii) centrifuging the lysed cells at low speed to remove cellular debris; (iii) adjusting the clarified supernatant to 1.5 M ammonium sulfate; and (iv) clarifying the cellular supernatant by centrifugation at 100,000×g to provide an S100 supernatant.

EXAMPLES

Features and advantages of the inventive concept covered by the present invention are further illustrated by the examples which follow.

Example 1

Strains

The *H. capsulatum* virulent strain G-217B (ATCC # 26032; generously provided by W. E. Goldman, Washington University) was used in all experiments. *H. capsulatum* yeast cultures were grown with gentle shaking at 37° in 3% glycerol (v/v) or 2% dextrose (w/v) HMM medium (Worsham, P. L. et al., *J. Med. & Veterinary Mycology*, 26:137–43). YPD (1% yeast extract, 1% bacto-peptone, and 2% glucose) was used as rich medium for growth overnight at 37° C. of H99, a virulent clinical isolate of *C. neoformans* serotype A (generously provided by J. K. Lodge of St. Louis University). *Aspergillus nidulans* (strain: FGSC A4 Glasgow wild type VeA+) and *Aspergillus niger* (strain: FGSC A732 *A. niger* wild type) were obtained from the University of Kansas Fungal Genetics stock center and grown in Sabouraud's media (4% Dextrose, 1% Bacto-Peptone) for 3 days in a shaking incubator at 37° C. The *E. coli* DH5α strain or SOLAR strain (Stratagene, Inc.) were used for plasmid transformations.

Example 2

Isolation and Characterization of the Catalase A and P cDNA Clones and Introns

A *H. capsulatum* cDNA library was screened for catalase A sequences by probing plaque lifts with PCR fragments generated using degenerate primers designed from three highly conserved regions dispersed along the length of the known *Aspergillus fumigatis* and *Emericella nidulans* catalase A enzymes. An initial PCR amplification was done with genomic DNA as template with the primers #1 (CatA 5') and #2 (CatA 3') (FIG. 1). This resulted in a primary product of 600 bp. The products of this initial PCR reaction were used as template for a nested reaction, with the #1 (CatA 5') and #3 (CatA 3'B) primers to generate a secondary 400 bp product, which was the predicted size based on the *Aspergillus* CATA homologue. The sequence of the 5' primer (#1—CatA 5') was 5'-CNATHGAYAAYAARGCNTAYC-3' (SEQ ID NO: 25); the sequence of the most 3' complementary strand primer (#2—CatA 3') was 5'-TCRTCRCARTGRTC-NARYTCR-3' (SEQ ID NO: 26); and the sequence of a nested complementary primer (#3—CatA 3'B) was 5'-CYT-CRAANCKRTTNGGCCART-3' (SEQ ID NO: 27), where the mixed base codes are N=A+C+G+T, R=A+G, Y=C+T, M=A+C, K=T+G, S=C+G, W=A+T, H=A+C+T, B=C+G+T, D=A+G+T, and V=A+C+G.

PCR amplification conditions for the CATA gene followed a step down procedure of one "hot-start" cycle at 94° C. for 5 minutes followed by holding the temperature at 80° C. in order to add the Taq polymerase. After addition of polymerase, the reaction was continued with six stages of cycling as follows: a melting step of 94° C. for 20 seconds; an annealing step at 65° C., 60° C., 58° C., 56° C., 55° C., and 52° C. for 20 seconds for each of the six stages, respectively; and an extension step of 72° C. for 20 seconds. Each of the stages described above was repeated twice. Subsequently, 15 cycles of 94° C. for 20 seconds, 50° C. for 20 seconds, and 72° C. for 20 seconds, followed by a final cycle of 94° C. for 1 minute, 50° C. for 1 minute, and 72° C. for 3 minutes, were performed. The reaction buffer (160 mM $(NH_4)_2SO_4$, 670 mM Tris-HCl, pH 8.8 at 25° C., 0.1% Tween-20) was adjusted to 2 mM $MgCl_2$.

As described above, the initial PCR amplification used genomic DNA as template with the primers #1 (CatA 5') and #2 (CatA 3') to generate a primary product of about 600 bp. The primary product of this initial PCR reaction was used as template for a nested reaction, with the #1 (CatA 5') and #3 (CatA 3'B) primers, using the same conditions as those in the first reaction. This reaction consistently resulted in amplification of a 400 bp product that was similar to the predicted size expected from a product derived from a CATA gene, based on the *Aspergillus* sequences. This final PCR product was gel purified and ligated with the pCR 2.1 TOPO vector from Invitrogen Life Technologies, Inc., (Carlsbad, Calif.). The sequence of the inserts coded for a peptide that showed significant similarity to a number of catalases, however, all of the clones proved to be truncated at the 5' end.

To construct a full length cDNA clone for CATA, a 5' RACE product was generated and ligated with the 3' clones (i. e. the 5' truncated cDNA) using commercially available reagents and protocols (5' RACE System for Rapid Amplification of cDNA Ends, Ver. 2.0; Invitrogen Life Technologies, Inc.). RNA for the 5'RACE amplification was isolated from *H. capsulatum* cultures challenged with 50 mM $H_2O_2$, which as shown below induces accumulation of CATA mRNA. The sequence of the gene specific primers used in the reverse transcription step of the 5'RACE reaction were 5'-CTTGATCCAACTAAGATATGG-3' (SEQ ID NO: 28) and 5'-CAACGTCGATGAGTTTTTCC-3' (SEQ ID NO: 29). The final product, containing the missing 5' sequence of the CATA mRNA was cloned in the pCR 2.1 TOPO vector. Automated DNA sequencing showed this fragment contained all of the previously missing 5' CATA mRNA sequence (based on homology to CATA sequences in other fungi) as well as an overlap with the 5' end of the sequence contained in the originally-isolated truncated clones.

The sequence of the resulting full-length cDNA clone (GenBank accession # AF 189368), with an insert of 2537 bp, is shown in FIG. 1, where the bold portion of the sequence shows the 361 bases that were lacking from the original 5' truncated cDNA clone. The full-length CATA cDNA clones for a primary translation product of 749 residues with a predicted molecular mass of 84,643 Daltons. The presence of a single CATA gene in the *H. capsulatum* genome was confirmed by Southern analysis.

Lambda clones with large genomic fragments containing either the CATA or CATP genes, were isolated from a *H. capsulatum* genomic library. The library was constructed by Lofstrand Labs Limited (Gaithersburg, Md.) from Sau 3A partial digestion of *H. capsulatum* genomic DNA using the Lambda FIX II/Xho I partial Fill-in Vector Kit (Stratagene of La Jolla, Calif.). The library was screened using the XL1-Blue WRA (P2) strain (Stratagene, La Jolla, Calif.). *H.*

*capsulatum* CATA and CATP cDNA clones (described below) were used for radiolabeled probe construction and library screening. Analysis of the genomic clones was performed the same as described for the CATA and CATP cDNA libraries and confirmed both the locations and the sequences of the introns for both genes.

Pairwise comparisons of the *H. capsulatum* CATA amino acid sequence with CATA sequences of *Aspergillus fumigatus,* and *Emericella nidulans* using BOXSHADE 3.1 demonstrated a high level of identity with each (70.2% and 65.6%, respectively; FIG. 6). Boxshade is an algorithm that allows for a comparison of two sequences, with a general alignment followed by a residue by residue analysis. Thus, in the first step, the program checks each column of an alignment if there are enough similar residues to form a threshold consensus, where the limits used are determined by the user or set at 0.5 by default. In the second step, the program checks every residue to determine whether it is identical or similar to the consensus of the corresponding alignment column. If there is not a consensus, or the residue is neither identical nor similar to the consensus, the residue is not highlighted in any manner. Residues identical to the consensus or similar to the consensus (conservative substitutions) are indicated as black and gray, respectively. Residue similarity is defined by a variable parameter file set by the user (available on the internet).

The intracellular catalase P protein was purified as a single peptide from an SDS gel after transfer to a PVDF membrane followed by cyanogen bromide fragmentation and elution. Three of the internal peptide fragments were purified and subjected to amino acid sequencing, and the peptide sequences used to design degenerate primers CATP5' (5'-ATHCAYCARGTNATGCAYYT-3') (SEQ ID NO: 30), CATP3' (5'-TCYTTRTTNACNCKDATRAA-3') (SEQ ID NO: 31), and CATP3'B (5'-AANGCNGCYTGYTCCAT-3') (SEQ ID NO: 32). The CATP primers were used in PCR reactions with genomic DNA employing nested PCR using "hot-start" PCR with amplification using the two outer primers (CATP5' and CATP3') as described for CATA amplification, followed by amplification using the CATP5' and CATP3'B primers. The resulting PCR product was used to screen a *H. capsulatum* cDNA library. A full-length CATP cDNA clone with an insert of 2014 bp was isolated and upon sequencing, found to contain the full length cDNA (GenBank accession # AF189369).

The full-length cDNA clone for CATP (SEQ ID NO: 4) is shown in FIG. 3. Southern analysis demonstrated that, like the CATA gene, there is only a single CATP gene in *H. capsulatum.* The sequence for the CATP gene, including introns, and upstream and downstream untranslated regions (SEQ ID NO: 6), was determined by automated sequencing of clones isolated from the genomic library is shown in FIG. 4. The open reading frame encodes a protein of 503 residues with a predicted molecular mass of 57,247. A multiple sequence alignment of the *H. capsulatum* catalase P with known fungal catalases, as well as peroxisomal catalases of several *Hemiascomycetes* is shown in FIG. 7.

Intron locations and sequences for the CATA and CATP genes were determined by comparison of the sequences of PCR amplification products generated using cDNA vs. genomic DNA as the template. It was found that the coding region of the CATA gene is interrupted by 2 introns: the two splice sites are shown in FIG. 1, labeled I1 and I2. The sizes of the CATA introns 1 and 2 are 84 bp and 73 bp, respectively (FIGS. 1 and 2). It was found that the coding region of the CATP gene is interrupted by 3 introns: the splice sites are shown in FIG. 3, labeled I1, I2 and I3. The sizes of introns 1, 2 and 3 are 137 bp, 136 bp, and 98 bp, respectively (FIGS. 3 and 4). Sequences for the introns are shown in FIG. 5

Example 3

DNA Purification and Southern Analysis

*H. capsulatum* genomic DNA used for the construction of a genomic library was prepared by a modification of the protocol described by Woods et al. (Woods et al., 1992, *Mol. Microbiol.,* 6: 3603–3610) adapted to a 50 ml culture size. Genomic DNA used for Southern blot analysis was isolated by a modification of the Pitkin et al. (Pitkin et al., 1996, *Microbiology,* 142: 1557–1565). Briefly, mycelial cultures were pelleted and the fungi lysed by vortexing and extraction with CTAB extraction buffer (100 mM Tris-HCl, pH 7.5, 700 mM NaCl, 10 mM EDTA, 1% CTAB (Hexadecyltrimethylammonium bromide), 1% β-mercaptoethanol) by incubation at 65° C. (30 min) followed by extraction with an equal volume of chloroform, and the DNA pelleted from the aqueous supernatant by adding an equal volume of isopropanol. Upon precipitation (5000 g, 10 min) the DNA is resuspended in a small volume of water, digested with Rnase A, extracted with phenol/chloroform and ethanol precipitated.

Southern blotting was performed as described by Sambrook et al., (Sambrook, et al., Molecular Cloning: A Laboratory Manual, Cold Spring Harbor Laboratory Press, 1989, Chapter 9). Digested DNA (10 μg/lane) was separated by electrophoresis through 1% agarose gels, transferred by capillary blotting to Hybond-N membrane (Amersham) and hybridized to radiolabeled probes (Sambrook et al., Chapter 9). Radiolabeled probes were constructed from PCR products containing the entire transcribed region or smaller intronic regions using the procedures described in the Random Priming Labeling Kit (Invitrogen, Carlsbad, Calif.).

For the Southern hybridization shown as FIG. 8, hybridizations were performed in Church's buffer (Church, G. M. & Gilbert, W., 1984, *Proc. Natl. Acad. Sci., USA* 81: 1991–1995) at 60° C. overnight and washed once at room temperature on a shaking platform for 30 min, in a 1:1 dilution of Church's hybridization buffer (Church, G. M. & Gilbert, W., 1984, *Proc. Natl. Acad. Sci, USA* 81: 1991–1995). DNA digests from *H. capsulatum* (H), *B. dermititidis* (B), and *C. neoformans* (C) digested with BamH I, Xba I, and Xho I were resolved by electrophoresis through 1% agarose and blotted to Hybond as described above. Blots were probed with radiolabeled PCR products derived either from CATA intron 1 (FIG. 8A) or CATP introns 1 and 2, or intron 3 (FIG. 8B).

Radiolabeled probes were constructed from PCR products containing the intronic regions of both the CATA and CATP genes as follows. Primers 5'-attcacaaaagctccagtttc-3' (SEQ ID NO: 33) and 5'-ggattctttcatggtcaaaatcg-3 (SEQ ID NO: 34) were used to construct a PCR product of the region containing intron 1 of the CATA gene. Primers 5'-atgggtgccgatgatacc-3' (SEQ ID NO: 35) and 5'-ccgctcgcggtcaaaatgc-3' (SEQ ID NO: 36) were used to construct a PCR product of the region containing the first 2 introns (intron 1 and intron 2) of the CATP gene. Primers 5'-gaagtgctggacgacatcag-3'(SEQ ID NO: 37) and 5'-gggaagtcgtacaattacc-3' (SEQ ID NO: 38) were used to construct a PCR product of the region containing intron 3 of the CATP gene. PCR reaction conditions were as follows: denaturation at 94° C. for 1 minute followed by 20 three-step amplification cycles of 94° C. for 20 seconds, 50° C. for 20 seconds, and 74° C. for 20 seconds with a final extension at 74° C. for 1.5 minutes. The components of the PCR reactions were as described in Example 4. The results of these Southerns show these regions of these 2 genes specifically hybridize with DNA from *H. capsulatum* (H) and not with DNA from *B. dermatititis* (B) or *C. neoformans* (C).

Example 4

Figure 11:
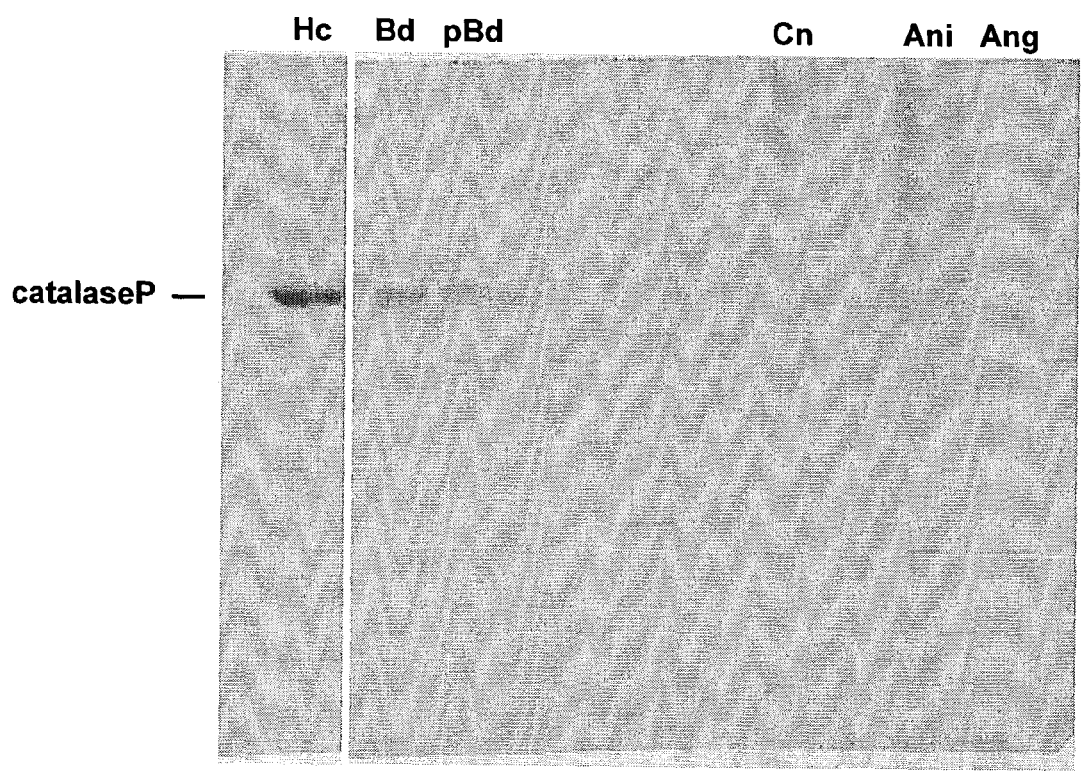
FIG. 11 shows a Western blot of soluble extracts from *H. capsulatum* (Hc), *B. dermatititis* (Bd), purified *B. dermatititis* catalase P (pBd), *C. neoformans* (Cn), *A. nidulans* (Ani), and *A. niger* (Ang) developed using antiserum to *H. capsulatum* catalase P. The marker to the left of the blot indicates the position for *H. capsulatum* catalase P.

PCR Assay Using CATA and CATP Primers

For amplification of CATA sequences, PCR was conducted using primers corresponding to 5'-Aassay primers 1, 2 and 3 and 3'-Aassay primers 1, 2, and 3 as shown in FIG. 2. Thus, primer Aassay5'-1 (5'-tgcgggcaacatatgataac-3') (SEQ ID NO: 12) and Aassay5'-2 (5'-gataaccatcgagttagatcc-3') (SEQ ID NO: 13) hybridize to CATA intron 1, whereas primer Aassay5'-3 (5'-cgtccgctggtgttctaac-3') (SEQ ID NO: 14) hybridizes to exon 2. Primer Aassay3'-1 (5'cgatcaacacgaaaatatcc-3') (SEQ ID NO: 15) and Aassay3'-2 (5'-tatcaatcaatacttac-3') (SEQ ID NO: 16) both hybridize to CATA intron 2, whereas primer Aassay3'-3 (5'-gacatcacggactgtatcg-3') (SEQ ID NO: 17) hybridizes to exon 2. Interestingly, using primer Aassay3'-3 from *H. capsulatum* CATA exon 2, there is significant cross-reactivity with *B. dermatititis* DNA, indicating that at the exon level, the catalases from these two organisms are similar, whereas intron sequences provide a means to distinguish the two organisms.

For amplification of CATP sequences, PCR was conducted using primers corresponding to 5'-Passay primers 1, 2 and 3 and 3'-Passay primers 1, 2, and 3 as shown in FIG. 4. Thus, primer Passay5'-1 (5'-gagcttcgatacttaatctag-3') (SEQ ID NO: 18) and Passay5'-2 (5'-gacggacgtgtctaaaacg-3') (SEQ ID NO: 19) hybridize to CATP intron 1. Primer Passay5'-3 (5'-gctatcattagagaacagatc-3') (SEQ ID NO: 20) and Passay3'-3 (5'-gatctagtggggacaatacg-3') (SEQ ID NO: 23) hybridize to CATP intron 2, and primer Passay3'-1 (cagggttctgggtatgtct-3') (SEQ ID NO: 21) and Passay3'-2 (5'-gtgccgcagctgatggttg-3') (SEQ ID NO: 22) hybridize to CATP intron 3.

Samples included 1 ug of *H. capsulatum*, *B. dermatititis* or *C. neoformans* genomic DNA. Amplifications were performed in the presence 0.5 mM $MgCl_2$, 16 mM $(NH_4)_2SO_4$, 67 mM Tris-HCl, pH 8.8, 0.1% Tween 20, and were performed with a denaturation step at 95° C. for 1 min, followed by 15 cycles of 20 sec at 95° C., annealing at 55° C. for 20 sec, and extension at 74° C. for 20 sec, with a final extension at 74° C. for 90 sec. Results are shown in FIG. 10. Both excess high molecular weight template and low molecular weight primers or primer complexes are seen in some of the lanes.

Example 5

Purification of *H. Capsulatum* Catalase P

The cellular catalase P enzyme was purified from a soluble S-100 cellular extract. *H. capsulatum* cells were suspended at 0.5 g $ml^{-1}$ in lysis buffer (50 mM $NaPO_4$pH 7, 250 mM mannitol, 50 mM sucrose, and 50 μM PMSF) and mechanically broken with glass beads (0.5 mm diameter Zirconium beads; Biospec Products, Bartlesville, Okla.) in a Bead-Beater (Biospec Products) for five pulses of 30 seconds, with 10 min of cooling on ice between pulses. The cellular debris was removed by centrifugation at 12,000×g at 4° C. and the supernatant clarified by centrifugation at 100,000×g. The S-100 supernatant was adjusted to 1.5 M ammonium sulfate and the supernatant clarified by centrifugation at 10,000×g. The clarified supernatant was applied to a cyclohexyl-sepharose column and washed with buffer A (1.5 M ammonium sulfate, 0.025 M sodium phosphate, pH 7). Proteins bound to the column were eluted with a linear gradient between buffer A and buffer B (0.025 M sodium phosphate pH 7). Fractions containing catalase activity are identified by their ability to degrade hydrogen peroxide (followed spectrophotometrically as a decrease in absorbance at 240 nm) and were pooled and dialyzed against column equilibration buffer (2 mM sodium phosphate buffer pH 6.8). The dialyzed eluate was applied to a column of hydoxyapatite and bound proteins were eluted with a linear gradient of 2 to 400 mM sodium phosphate. Fractions containing catalase activity were identified as described above. The pooled catalase fractions were purified further by SDS gel electrophoresis and transferred to PVDF membrane (Waters Corp.) (FIG. 14).

The purified catalase protein (57 kDa) was fragmented by cyanogen bromide and four peptide fragments were purified by C18 reverse phase HPLC chromatography. Sequencing of the purified peptide fragments from their N-termini was performed with an Applied Biosystems pulsed-liquid phase sequencer (model 477A) equipped with a model 120A PTH-amino acid analyzer.

Example 6

Preparation of Antibody to *H. Capsulatum* Catalase P and Catalase A

Antibodies to Catalase A and P have been generated and used to study the cellular localization of these enzymes. Immunoblots confirm that catalase P is a soluble enzyme that is likely to be peroxisomal. Catalase A immunoblots indicate this enzyme is extremely insoluble and localized at the cellular surface.

The Qiagen Expressionist System (QIAexpress System by Qiagen Inc., Valencia Calif.) was used to express and purify recombinant forms of the catalase A and P proteins. Both the over-expression and purification of the protein was performed according to the denaturing protocol described in the Expressionist catalog. Briefly, an insert of the cDNA coding region for catalase A was constructed by PCR using BamH I tagged primers of the most 5' and 3' sequence of the ORF (open reading frame) and ligated into the pQE70 vector. The final purified expressed protein contained six histidine residues at the carboxyl terminus of the protein. For catalase P, BCII tagged primers were used to construct an insert of the cDNA coding region and generate a purified recombinant catalase P for antibody production. The purified recombinant CATA and CATP proteins (as well as the de novo purified CATP protein) was used to raise antibodies in rabbits by Animal Pharm Services Inc., (Healdsburg, Calif.).

Example 7

Western Blots Using CATA and CATP

Catalase P

Western blots were used to study the interaction of catalase P antibodies with catalase enzymes from other fungi. Referring now to FIG. 11, proteins (30 ug/lane for cell extracts and 5 ug/lane for purified proteins) were separated by gel electrophoresis in a 12% SDS polyacrylamide gel. The gels were blotted to Millipore Immobilon-P PVDF membrane (Immobilon, Bedford, Mass.) according to the procedure as described by the manufacturer (Immobilon Protein Blotting Protocols, 1991). The blots were first blocked in PBS (10 mM NaPO$_4$pH 7.2, 100 mM NaCl) with 3% BSA (bovine serum albumin) and then probed with catalase P antiserum. The westerns were incubated with primary antiserum at a 1:200 dilution in PBS/3% BSA overnight at room temperature, rinsed once with PBS and then probed for 5 hours at room temperature with a horse-radish peroxidase conjugated anti-rabbit IgG (Jackson Immunologicals, West Grove, Pa.) at a 1:1000 dilution in PBS/3% BSA. The blots were developed by exposure to 4-chlornapthol (30 mg dissolved in 10 ml of methanol) followed by H$_2$O$_2$ (75 ul of H$_2$O$_2$ in 50 ml of PBS). Color development was terminated by rinsing in PBS. As shown in FIG. 11, the catalase P antibodies recognize a protein the size of catalase P from *H. capsulatum*, as well as a similarly sized protein from *B. dermatititis*. The last three lanes, containing cell extracts from *C. neoformans* (Cn), *A. nidulans* (Ani), and *A. niger* (Ang), show no specific cross-reactivity with the catalase P antiserum.

Catalase A

To study expression of CATA in *H. capsulatum,* a western blot of proteins isolated from *H. capsulatum* grown in the presence of $H_2O_2$ was probed with a rabbit antiserum raised against the catalase A recombinant protein (dil. 1:500). Proteins were blotted to Millipore Immobilon membrane by standard protocols, and immunostaining performed as described by Evrard et al., (Evrard et al., 1990, *Nucleic Acid Res.,* 18: 1115–1119). Bound antibody was detected using a goat anti-rabbit purified IgG coupled with horseradish peroxidase (dil. 1:2000 from Jackson Immunologicals, West Grove, Pa.) with the substrate 4-chloro-1-napthol as described above.

Referring to FIG. 13, Lane 1 contains proteins precipitated by 70% ethanol from the *H. capsulatum* culture growth medium after clarification by centrifugation and filtration (0.45 micron filter). Lane 2 contains proteins recovered from the pellets resulting from both a 15,000 and 100,000×g centrifugation and after acetone extraction (primarily membrane proteins). Lane 3 contains proteins recovered from the soluble cytosolic supernatant after 70% ammonium sulfate precipitation. Cells were lysed using glass beads in a Braun bead beater in lysis buffer (0.5 M sucrose, 10 mM Na $PO_4$, 100 mM NaCl). The pre-immune serum showed no reaction to any proteins in the serum. The final serum reacted strongly with the recombinant catalase A protein and a smear of proteins in the membrane and extracellular protein fractions, but did not react with any of the proteins of the soluble cytosolic cellular fraction (FIG. 13) indicating that CATA is a membrane protein.

Example 8

Regulation of *H. capsulatum* Catalase Genes in Response to Oxidative Stress To determine if the *H. capsulatum* catalase genes are differentially regulated during oxidative stress and development, the abundance of transcripts for each of the *H. capsulatum* catalase genes, CATA, CATB, and CATP, in response to $H_2O_2$ challenge and in two developmental stages (mycelia or yeast) was examined. Total RNA was extracted from cultures of strain G-217B yeast or mycelia according to a modification of the acid guanidinium thiocyanate extraction procedure of Chomczynski & Sacchi (1987). RNA samples (25 μg/lane) were electrophoresed in formaldehyde-1% (w/v) agarose gel (Sambrook, J., et al., *Molecular Cloning: A Laboratory Manual,* 1989, Cold Spring Harbor Laboratory Press, Plainview, N.Y.) transferred by capillary blotting to Hybond-N membrane (Amersham Pharmacia Biotech Inc.) and hybridized to radiolabeled probes in the hybridization solution of Church and Gilbert (Church, G. M. & Gilbert, W., 1984, *Proc. Natl. Acad. Sci., USA* 81: 1991–1995) according to the procedure described by Johnson and Schmidt (Johnson, C. H. & Schmidt, G. W., 1993, *Plant Mol. Biol.,* 22: 645–658). Results were obtained both by autoradiography and phosphorimaging (Molecular Dynamics Storm Phosphorimager, Amersham Pharmacia Biotech Inc., Piscataway, N.J.). Band intensities were determined from the Phosphorimager data and normalized to the band intensity of the small subunit rRNA in the same lane. Imagequant 5.1 software (Molecular Dynamics) was used for these measurements.

As shown in FIG. 12, CATA mRNA abundance showed a marked increase after $H_2O_2$challenge. The effect was most pronounced within 1.5 hours and nearly abated by 3 hours after $H_2O_2$ challenge. CATA mRNA amount was restored to basal levels within 4–6 hours after challenge. In contrast, challenge with $H_2O_2$ has little or no effect on the abundance of CATB and CATP transcripts from either of these genes during yeast phase growth.

Example 9

Phylogenetic and Intron-Residence Analyses of Catalase A and Catalase P

Alignments of the amino acid sequences for catalase A and P homologues were created with the multiple-alignment algorithm of ClustalW (available on the internet) with Kimura correction and maximum fixed-gap and gap extension penalties to reduce the influence of gaps in the subsequent analyses (Thompson, J. D., et al., 1994, *Nucleic Acids Res* 22: 4673–4680). Evolutionary relationships of the sequences were determined with both parsimony and distance methods using programs contained in the PHYLIP package (PHYLIP Version 3.5; J. Felsenstein at University of Washington, Seattle, Wash.) as described previously (Klotz, M. G., 2001, *American Society for Microbiology, 101st annual meeting, Abstract H*-18) A recent analysis of the core amino acid sequences from 129 monofunctional catalases, which produced a tree with three separate clades of the catalase gene family (Loewen, P. C., et al., *ASM News* 66: 76–82) was extended by newly available sequences including the *H. capsulatum* CATA, CATB and CATP proteins. In addition, intron residence was mapped on the aligned amino acid sequences from eukaryotic organisms, which generated a positional matrix. This matrix was processed by heuristic parsimonial analysis using PAUP version 3.1.1 (Smithsonian Institute, Washington D.C.). In order to minimize the possibility that the algorithm would detect a local parsimony (potential monophyly of clusterings comprised of more than one species), 1000 bootstrap replicates were generated. A 50% majority-rule consensus tree was constructed from parsimony replicates by using tree bisection-reconnection and nearest-neighbor branch-swapping methods with stepwise addition of the closest sequence.

Phylogenetically, all of the plant catalases cluster in clade 1. Clade 3 contains only small-subunit monofunctional catalases from diverse phylogenetic groups including bacteria, animals and fungi (FIG. 15A). Clade 2 contains large-subunit monofunctional catalases from bacteria and fungi.

A detailed catalase gene intron analysis was performed to clarify the relationships between the subgroups of clade 2. While the intron positions and sequences for *H. capsulatum* CATB were obtainable from the Genbank deposit of the gene encoding the M-antigen (GenBank accession number AF026268), intron locations and sequences for the *H. capsulatum* CATA and CATP genes were determined as described herein by comparison of PCR products from amplification of intron-bearing regions of the cDNA and genomic DNA. Thus, it was found that the coding region of the CATA gene is interrupted by introns 1, and 2, which are 84 bp and 73 bp, respectively, in size (FIGS. 1 and 2). It was found that the coding region of the CATP gene is interrupted by introns 1, 2, and 3, which are 137 bp, 136 bp, and 98 bp, respectively in size (FIGS. 3 and 4). Intron positions and sequences of other eukaryotic catalase genes were obtained from pertinent Genbank deposits, and were mapped on the amino acid sequences in the ClustalW-aligned sequences. The derived intron matrix was processed with PAUP and the results used to construct a parsimonial tree (FIG. 15B).

Figure 15A:
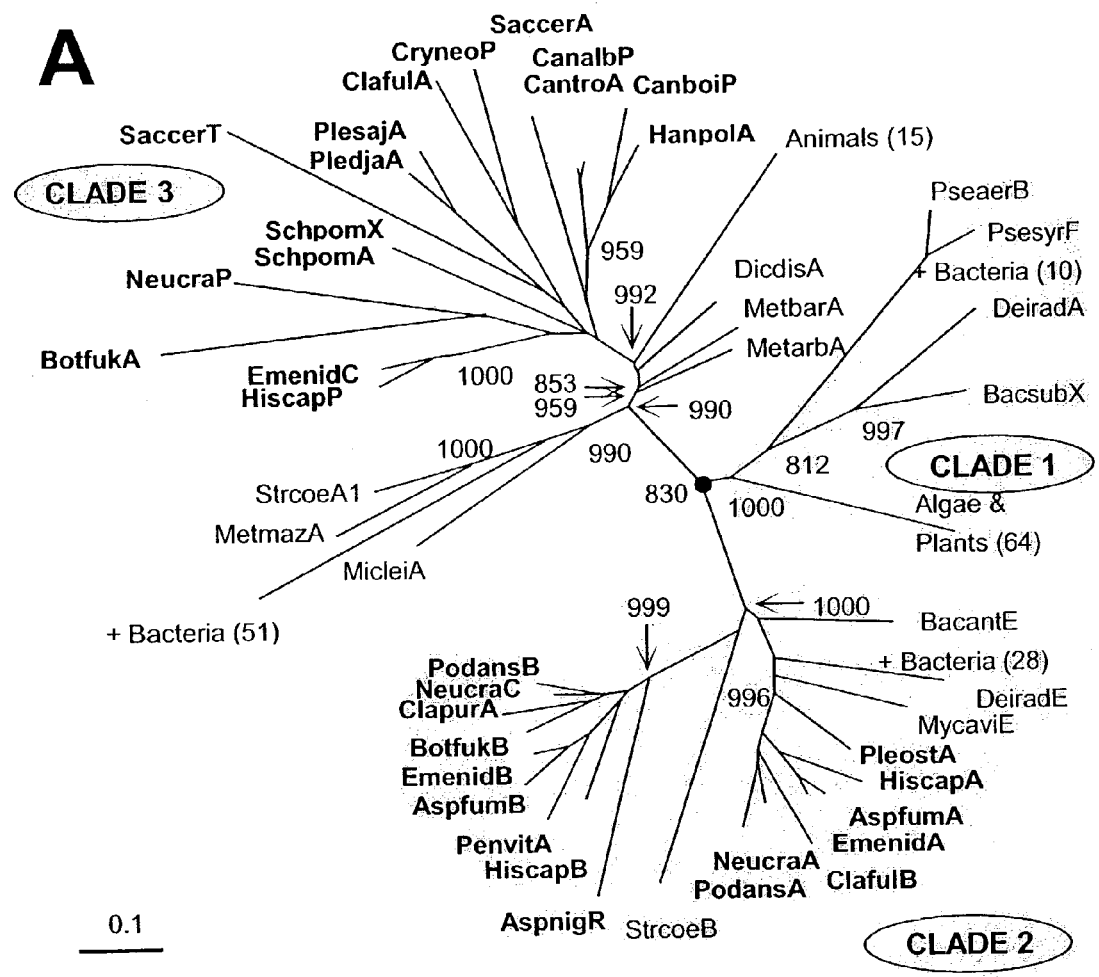
FIG. 15 shows phylogenetic and intron analyses of the monofunctional catalase gene family using *Histoplasma capsulatum* catalase amino acid sequences and intron positions in accordance with an embodiment of the present invention. Panel A shows a distance-neighbor joining tree derived from a ClustalW-alignment of 210 catalase amino acid sequences. Panel B shows a maximum parsimony tree constructed from analyses of intron positions mapped onto the alignments of the catalase amino acid sequences. The resulting clades reflect the acquisition (light shades) and loss (dark shades) of introns in an individual intron lineage. The individual intron lineages were grouped according to catalase family structure established by the phylogenetic analysis (see panel A).
Figure 15B:
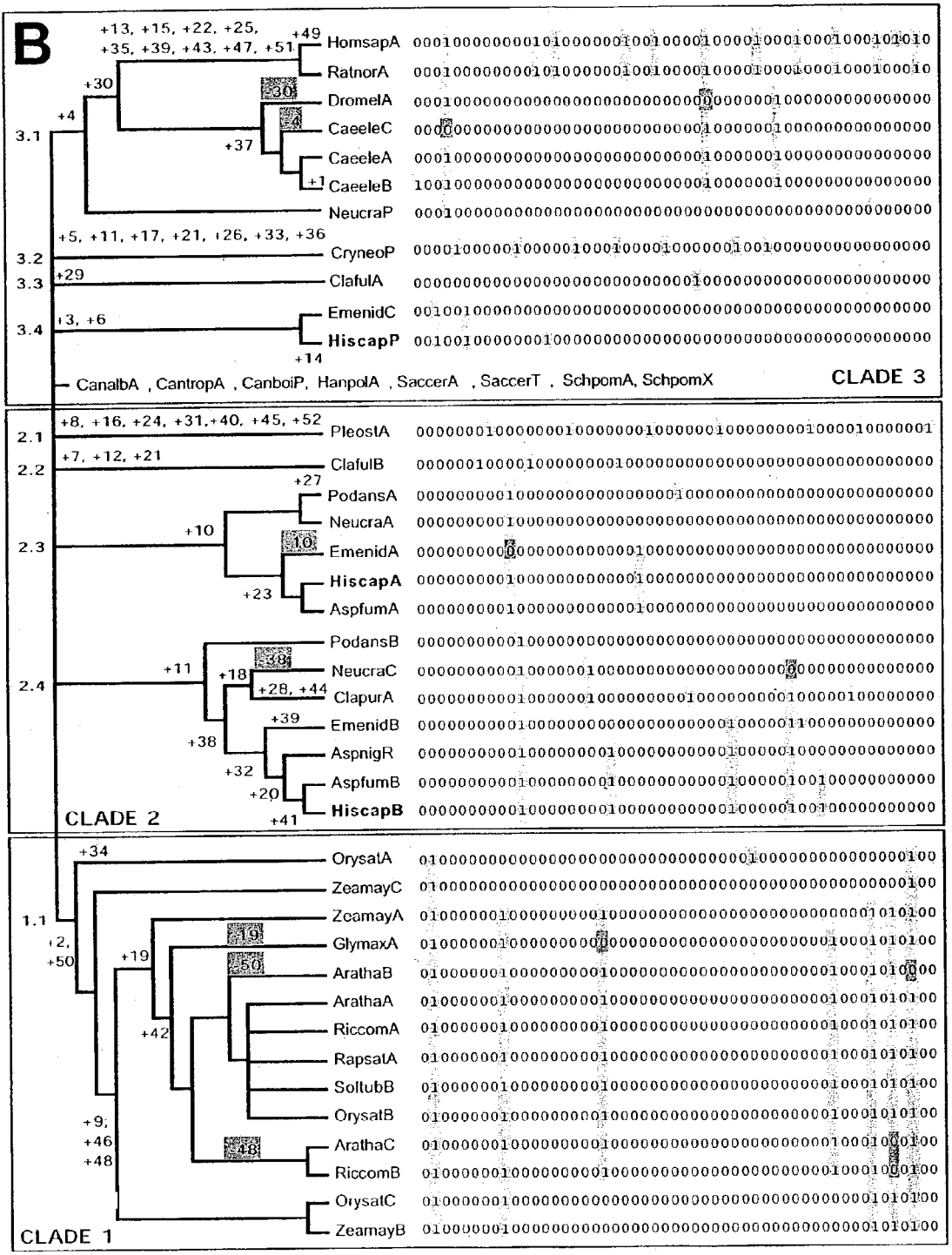

While the grouping of plant (clade 1) and animal catalases (clade 3) implies the existence of single-rooted intron lineages, multiple independent intron lineages are evident for fungal catalase genes in clades 2 and 3 (FIGS. 15A and B). Intron lineage 2.4 is congruent with the respective branch of large-subunit fungal catalases in clade 2. The three other fungal intron lineages in clade 2 represent catalases that sub-group within the branch of large-subunit bacterial catalases. Analysis of introns of the catalases in clade 3 allowed the definition of two main subgroups of fungal small subunit catalases. One contains only intronless peroxisomal catalases from *Saccharomycotina* yeasts (*Saccharomyces, Hansenula, Candida*) and the other subgroup contains intronless catalases (*Schizosaccharomyces, Saccharomyces*) and catalases from diverse fungi (*Cladosprium, Botryotina, Cryptococcus, Emericella, Histoplasma,* and *Neurospora*) whose catalase genes have introns. The *Cryptococcus* catalase gene has 7 unique introns, whereas the *H. capsulatum* CATP and *E. nidulans* CATC catalase genes, with 3 and 2 introns respectively, belong to the same intron lineage (FIG. 15B). The intron in the *Neurospora crassa* CATP gene is incorporated at position 4 as found in animal catalases, and the *Cladosporium fulvum* CAT1 catalase gene (Bussink & Oliver (2001) contains a single intron in a unique position (FIG. 15B).

Abbreviations used for FIG. 15, followed by GenBank accession numbers in parentheses, indicate the source organism of the sequences, as follows: Fungi: AjecapA (AF189368), AjecapB (AF139985, AF026268), AjecapP (AF189369) are from *Ajellomyces (Histoplasma) capsulatum;* AspfumA (AFU87630) and AspfumB (AFU87850) are from *Aspergillus fumigatus;* AspnigR (Z23138)—*A. niger;* CanalbA1 (AB006327)—*Candida albicans;* CantroA (M18832)—*Candida tropicalis;* ClafulA (AF222055), ClafulB (AF222056)—*Cladosporium fulvum;* ClapurA (AJ001386)—*Claviceps purpurea;* CryneoP (available on the internet), *Crytococcus (Filobasidiella) neoformans;* EmenidA (U37803), EmenidB (U80672), EmenidC (AF316033)—*Emericella (Aspergillus) nidulans;* HanpolA (X56501)—*Hansenula polymorpha;* NeucraB (AY027545), NeucraC (AY027544), NeucraP (available on the internet)—*Neurospora crassa;* PleostA (U75451)—*Pleurotus ostreatus;* PodansA (AJ011298), PodansB (AJ011309)—*Podospora anserine;* SaccerA (X13028), SaccerT (X04625)—*Saccharomyces cerevisiae;* SchpomA (D89126)—*Schizosaccharomyces pombe;* Bacteria: BacfirA (M74194)—*Bacillus firmus;* BacsubE (X85182)—*B. subtilis;* DeiradE (AE001825)—*Deinococcus radiodurans;* EcoliE (M55161)—*Escherichia coli;* MycaviE (L41246)—*Mycobacterium avium;* PseaerC (available on the internet)—*Pseudomonas aeruginosa;* PseputC (U82622)—*P. putida;* RhimeC (AF121348)—*Rhizobium meliloti;* StrcoeB (AF000419)—*Streptymyces coelicolor;* XanoryX (AF170449)—*Xanthomonas orizae;* Plants: ArathaA (AF021937), ArathaB (AL022023), ArathaC (AF021937)—*Arabidopsis thaliana;* GlymaxA (AF035252), GlymaxB (AF035253)—*Glycine max;* OrysatA (X61626), OrysatB (D26484), OrysatC (AB0205021)—*Oryza sativum;* RiccomA (D21161), RiccomB (D21162)—*Ricinus communis;* SoltubB (U27082)—*Solanum tuberosum;* ZeamayA (X12538), ZeamayB (X54819), ZeamayC (L05934)—*Zea mays;* Animals: CaeeleA (AL034488), CaeeleB (AL034488), CaeeleC (AL034488)—*Caenorhabditis elegans;* DromelA (U00145)—*Drosophila melanogaster;* HomsapA (AL035079)—*Homo sapiens;* RatnorA (AH004967)—*Rattus norvegicus.*

Publications referred to throughout this patent application are hereby incorporated by reference in their entirety in order to more fully describe the state of the art as known to those skilled in the art in the relevant fields as of the date of the invention described and claimed herein.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. An isolated nucleic acid molecule for detection of *H. capsulatum* selected from the group consisting of:
   (a) a nucleic acid molecule comprising the sequence of SEQ ID NO: 7 or the complement of SEQ ID NO: 7;
   (b) a fragment of SEQ ID NO: 7 consisting of 20 or more consecutive nucleotides of SEQ ID NO. 7, or the complement thereof; and
   (c) a nucleic acid molecule of up to 25 nucleotides in length that comprises 20 or more consecutive nucleotides of SEQ ID NO: 7 or the complement thereof;

wherein the isolated nucleic acid molecule hybridizes to intron 1 of the *H. capsulatum* catalase A gene.

2. The isolated nucleic acid molecule of claim 1, wherein the fragment consists of SEQ ID NO: 12 or SEQ ID NO: 13.

3. An isolated nucleic acid molecule for detection of *H. capsulatum* selected from the group consisting of:
   (a) a nucleic acid molecule comprising the sequence of SEQ ID NO: 8 or the complement of SEQ ID NO: 8;
   (b) a fragment of SEQ ID NO: 8 consisting of 20 or more consecutive nucleotides of SEQ ID NO: 8 or the complement thereof; and (c) a nucleic acid molecule of up to 25 nucleotides in length that comprises 20 or more consecutive nucleotides of SEQ ID NO: 8 or the complement thereof;
wherein the isolated nucleic acid molecule hybridizes to intron 2 of the *H. capsulatum* catalase A gene.

4. The isolated nucleic acid molecule of claim 3, wherein the fragment consists of SEQ ID NO: 15.

5. An isolated nucleic acid molecule for detection of *H. capsulatum* selected from the group consisting of:
   (a) a nucleic acid molecule comprising the sequence of SEQ ID NO: 7 or the complement thereof or SEQ ID NO: 8 or the complement thereof;
   (b) a fragment of SEQ ID NO: 7 consisting of 20 or more consecutive nucleotides of SEQ ID NO. 7 or the complement thereof;
   (c) a fragment of SEQ ID NO: 8 consisting of 20 or more consecutive nucleotides of SEQ ID NO: 8 or the complement thereof; and
   (d) an oligonucleotide selected from the group consisting of SEQ ID NO: 12, SEQ ID NO: 13, and SEQ ID NO: 15.

6. A method for detecting *H. capsulatum* in a sample comprising the steps of:
   (a) exposing the sample to at least one isolated nucleic acid molecule that hybridizes to *H. capsulatum* intron 1 comprising SEQ ID NO: 7 or the complement thereof, or to *H. capsulatum* intron 2 comprising SEQ ID NO: 8 or the complement thereof of the *H. capsulatum* catalase A gene (CATA); and
   (b) determining whether there is hybridization of the isolated nucleic acid molecule to the sample, wherein a sample comprising *H. capsulatum* exhibits detectable hybridization and a sample lacking *H. capsulatum* does not exhibit hybridization, and wherein the isolated nucleic acid molecule is selected from the group consisting of: (i) a nucleic acid molecule comprising the sequence of SEQ ID NO: 7 or the complement thereof, SEQ ID NO: 8 or the complement thereof; (ii) a fragment of SEQ ID NO: 7 consisting of 20 or more consecutive nucleotides of SEQ ID NO. 7 or the complement thereof, a fragment of SEQ ID NO: 8 consisting of 20 or more consecutive nucleotides of SEQ ID NO: 8 or the complement thereof; (iii) a nucleic acid molecule of up to 25 nucleotides in length that comprises 20 or more consecutive nucleotides of SEQ ID NO: 7 or the complement thereof, a nucleic acid molecule of up to 25 nucleotides in length that comprises 20 or more consecutive nucleotides of SEQ ID NO: 8 or the complement thereof; and (iv) an oligonucleotide selected from the group consisting of SEQ ID NO: 12, SEQ ID NO: 13, SEQ ID NO: 15 and SEQ ID NO: 16.

7. The method of claim 6, wherein the sample is obtained from a human.

8. The method of claim 7, further comprising the steps of:
   (a) conducting polymerase chain reaction (PCR) amplification using the at least one nucleic acid molecule that hybridizes to intron 1 or intron 2 of the *H. capsulatum* catalase A gene (CATA) as an amplification primer; and
   (b) determining the presence or absence of the PCR product resulting from the amplification.

9. The method of claim 8, wherein the primers comprise at least one oligonucleotide molecule selected from the group consisting of SEQ ID NO: 12, SEQ ID NO: 13, SEQ ID NO: 15 and SEQ ID NO: 16.

10. The method of claim 8, further comprising PCR amplification conditions that result in detection of a PCR product comprising a *H. capulatum* intron DNA sequence in a sample comprising *H. capsulatum* but not in a sample that does not contain *H. capsulatum*.

11. An isolated nucleic acid molecule for detection of *H. capsulatum* selected from the group consisting of:
   (a) a nucleic acid molecule comprising the sequence of SEQ ID NO: 9 or the complement of SEQ ID NO: 9;
   (b) a fragment of SEQ ID NO: 9 consisting of 19 or more consecutive nucleotides of SEQ ID NO. 9, or the complement thereof; and
   (c) a nucleic acid molecule of up to 25 nucleotides in length that comprises 19 or more consecutive nucleotides of SEQ ID NO: 9 or the complement thereof;
   wherein the isolated nucleic acid molecule hybridizes to intron 1 of the *H. capsulatum* catalase P gene.

12. The isolated nucleic acid molecule of claim 11, wherein the fragment consists of SEQ ID NO: 18 or SEQ ID NO: 19.

13. An isolated nucleic acid molecule for detection of *H. capsulatum* selected from the group consisting of:
   (a) a nucleic acid molecule comprising the sequence of SEQ ID NO: 10 or the complement of SEQ ID NO: 10;
   (b) a fragment of SEQ ID NO: 10 consisting of 20 or more consecutive nucleotides of SEQ ID NO. 10, or the complement thereof;
   (c) a nucleic acid molecule of up to 25 nucleotides in length that comprises 20 or more consecutive nucleotides of SEQ ID NO: 10 or the complement thereof;
   wherein the isolated nucleic acid molecule hybridizes to intron 2 of the *H. capsulatum* catalase P gene.

14. The isolated nucleic acid molecule of claim 13, wherein the fragment consists of SEQ ID NO: 20 or SEQ ID NO: 23.

15. An isolated nucleic acid molecule for detection of *H. capsulatum* selected from the group consisting of:
   (a) a nucleic acid molecule comprising the sequence of SEQ ID NO: 11 or the complement of SEQ ID NO: 11;
   (b) a fragment of SEQ ID NO: 11, consisting of 19 or more consecutive nucleotides of SEQ ID NO: 11 or the complement thereof; and
   (c) a nucleic acid molecule of up to 25 nucleotides in length that comprises 19 or more consecutive nucleotides of SEQ ID NO: 11 or the complement thereof;
   wherein the isolated nucleic acid hybridizes to intron 3 of the *H. capsulatum* catalase P gene.

16. The isolated nucleic acid molecule of claim 15, wherein the fragment consists of SEQ ID NO: 21 or SEQ ID NO: 22.

17. An isolated nucleic acid molecule for detection of *H. capsulatum* selected from the group consisting of:
   (a) a nucleic acid molecule comprising the sequence of SEQ ID NO: 9, SEQ ID NO: 10, or SEQ ID NO: 11, or the complement of SEQ ID NO: 9, SEQ ID NO: 10, or SEQ ID NO: 11;
   (b) a fragment of SEQ ID NO: 9 consisting of 19 or more consecutive nucleotides of SEQ ID NO. 9 or the complement thereof, a fragment of SEQ ID NO: 10 consisting of 20 or more consecutive nucleotides of SEQ ID NO. 10 or the complement thereof, a fragment of SEQ ID NO: 11 consisting of 19 or more consecutive nucleotides of SEQ ID NO: 11 or the complement thereof; and
   (c) an oligonucleotide selected from the group consisting of SEQ ID NO: 18, SEQ ID NO: 19, SEQ ID NO: 20, SEQ ID NO: 21, SEQ ID NO: 22, and SEQ ID NO: 23.

18. A method for detecting *H. capsulatum* in a sample comprising the steps of:

(a) exposing the sample to at least one isolated nucleic acid molecule that hybridizes to *H. capsulatum* intron 1 DNA comprising SEQ ID NO: 9 or the complement thereof, *H. capsulatum* intron 2 comprising SEQ ID NO: 10 or the complement thereof, or *H. capsulatum* intron 3 comprising SEQ ID NO: 11 or the complement thereof of the *H. capsulatum* catalase P gene (CATP); and (b) determining whether there is hybridization of the isolated nucleic acid molecule to the sample, wherein a sample comprising *H. capsulatum* exhibits detectable hybridization, and wherein the isolated nucleic acid molecule is selected from the group consisting of: (i) a nucleic acid molecule comprising the sequence of SEQ ID NO: 9, SEQ ID NO: 10, or SEQ ID NO: 11, or the complements of SEQ ID NO: 9, SEQ ID NO: 10, or SEQ ID NO: 11; (ii) a fragment of SEQ ID NO: 9 consisting of 19 or more consecutive nucleotides of SEQ ID NO. 9 or the complement thereof, a fragment of SEQ ID NO: 10 consisting of 20 or more consecutive nucleotides of SEQ ID NO. 10 or the complement thereof, a fragment of SEQ ID NO: 11 consisting of 19 or more consecutive nucleotides of SEQ ID NO: 11 or the complement thereof; (iii) a nucleic acid molecule of up to 25 nucleotides in length that comprises 19 or more consecutive nucleotides of SEQ ID NO: 9 or the complement thereof, a nucleic acid molecule of up to 25 nucleotides in length that comprises 20 or more consecutive nucleotides of SEQ ID NO: 10 or the complement thereof, a nucleic acid molecule of up to 25 nucleotides in length that comprises 19 or more consecutive nucleotides of SEQ ID NO: 11 or the complement thereof; and (iv) an oligonucleotide selected from the group consisting of SEQ ID NO: 18, SEQ ID NO: 19, SEQ ID NO: 20, SEQ ID NO: 21, SEQ ID NO: 22, and SEQ ID NO: 23.

19. The method of claim 18, wherein the sample is obtained from a human.

20. The method of claim 18, further comprising the steps of:

(a) conducting polymerase chain reaction (PCR) amplification using the at least one nucleic acid molecule that hybridizes to intron 1, intron 2, or intron 3 of the *H. capsulatum* catalase P gene (CATP) as an amplification primer; and (b) determining the presence or absence of the PCR product resulting from said amplification.

21. The method of claim 20, wherein the primers comprise at least one oligonucleotide molecule selected from the group consisting of SEQ ID NO: 18, SEQ ID NO: 19, SEQ ID NO: 20, SEQ ID NO: 21, SEQ ID NO: 22 and SEQ ID NO: 23.

22. The method of claim 20, further comprising PCR amplification conditions that result in detection of a PCR product in a sample comprising *H. capsulatum* but not in a sample that does not contain *H. capsulatum*.

23. A composition for the specific detection of an active case of histoplasmosis in a subject comprising an isolated nucleic acid molecule selected from the group consisting of:

(a) a nucleic acid molecule comprising the sequence of SEQ ID NO: 24 or the complement of SEQ ID NO: 24; and (b) a fragment of SEQ ID NO: 24 consisting of 19 or more consecutive nucleotides of SEQ ID NO. 24 or the complement thereof.

24. A kit for detection of *H. capsulatum* comprising:

(a) a container comprising an isolated nucleic acid molecule selected from the group consisting of: (i) a fragment of SEQ ID NO. 7 consisting of 20 or more consecutive nucleotides of SEQ ID NO. 7 or the complement thereof; (ii) a fragment of SEQ ID NO. 8 consisting of 20 or more consecutive nucleotides of SEQ ID NO. 8 or the complement thereof; (iii) a fragment of SEQ ID NO. 9 consisting of 19 or more consecutive nucleotides of SEQ ID NO. 9 or the complement thereof; (iv) a fragment of SEQ ID NO. 10 consisting of 20 or more consecutive nucleotides of SEQ ID NO. 10 or the complement thereof; (v) a fragment of SEQ ID NO. 11 consisting of 19 or more consecutive nucleotides of SEQ ID NO. 11 or the complement thereof; and (vi) at least one oligonucleotide selected from the group consisting of SEQ ID NO: 12, SEQ ID NO: 13, SEQ ID NO: 15, SEQ ID NO: 16, SEQ ID NO: 18, SEQ ID NO: 19, SEQ ID NO: 20, SEQ ID NO: 21, SEQ ID NO: 22, and SEQ ID NO: 23; wherein the isolated nucleic acid hybridizes to introns 1 or 2 of the *H. capsulatum* catalase A gene or introns 1, 2 or 3 of the *H. capsulatum* catalase P gene; and (b) at least one separate container comprising *H. capsulatum* DNA comprising at least one of catalase intron A or catalase P intron DNA individually or in combination, wherein the catalase A intron DNA comprises at least one of SEQ ID NO: 7 or the complement of SEQ ID NO: 7, or SEQ ID NO: 8 or the complement of SEQ ID NO: 8, and wherein the catalase P intron DNA comprises SEQ ID NO: 9 or the complement of SEQ ID NO: 9, SEQ ID NO: 10 or the complement of SEQ ID NO: 10, or SEQ ID NO: 11 or the complement of SEQ ID NO: 11.

25. The isolated nucleic acid molecule of claim 1, comprising SEQ ID NO: 7 or the complement of SEQ ID NO: 7.

26. The isolated nucleic acid molecule of claim 3, comprising SEQ ID NO: 8 or the complement of SEQ ID NO: 8.

27. The isolated nucleic acid molecule of claim 11, comprising SEQ ID NO: 9 or the complement of SEQ ID NO: 9.

28. The isolated nucleic acid molecule of claim 13, comprising SEQ ID NO: 10 or the complement of SEQ ID NO: 10.

29. The isolated nucleic acid molecule of claim 15, comprising SEQ ID NO: 11 or the complement of SEQ ID NO: 11.

* * * * *

UNITED STATES PATENT AND TRADEMARK OFFICE
CERTIFICATE OF CORRECTION

PATENT NO.         : 7,052,837 B2
APPLICATION NO. : 10/099352
DATED                  : May 30, 2006
INVENTOR(S)       : Clayton H. Johnson, Joan E. McEwen and J. Lyndal York It is certified that error appears in the above-identified patent and that said Letters Patent is hereby corrected as shown below:

Column 4, Line 56, insert the following paragraph-- The present invention also allows for the detection of an active case of histoplasmosis. In this embodiment, the present invention relies on the discovery that *H. capsulatum* catalase A is expressed during oxidative stress. Thus, in one aspect, the present invention comprises a method for detecting an active case of histoplasmosis in a subject, comprising the steps of : (a) providing a sample from a subject; and (b) assaying for the presence *H. capsulatum* catalase A (*CATA*) polypeptide in said sample, wherein detection of *H. capsulatum* catalase A polypeptide is associated with an active case of histoplasmosis. In another aspect, the present invention comprises a method for detecting an active case of histoplasmosis in a sample, comprising the steps of (a) providing a sample; and (b) assaying the sample for the presence of *H. capsulatum* catalase A mRNA or any fragment thereof wherein detection of *H. capsulatum* catalase A mRNA is associated with an active case of histoplasmosis. In an embodiment, sequences from the 5' most end of the *H. capsulatum* catalase A gene are detected. Thus, in another aspect, the present invention comprises a composition for the specific detection of an active case of histoplasmosis in a subject comprising an isolated nucleic acid that hybridizes to the 5' most sequences of the *H. capsulatum* catalase A gene comprising the sequence set forth in SEQ ID NO:24.--

UNITED STATES PATENT AND TRADEMARK OFFICE
CERTIFICATE OF CORRECTION

| | |
|---|---|
| PATENT NO. | : 7,052,837 B2 |
| APPLICATION NO. | : 10/099352 |
| DATED | : May 30, 2006 |
| INVENTOR(S) | : Clayton H. Johnson, Joan E. McEwen and J. Lyndal York |

It is certified that error appears in the above-identified patent and that said Letters Patent is hereby corrected as shown below:

Column 4, Line 66, delete the whole paragraph starting "The present invention also comprises a method for the diagnosis of histoplasmosi in a subject" it is a duplicate paragraph.

Column 6, Lines 49-59 should read--FIG. 7 illustrates a multiple alignment of the *H. capsulatum* catalase (Hc) P enzyme (SEQ ID NO: 43) with other small subunit catalases from *Emericella (Aspergillus) nidulans* (En) (SEQ ID NO: 44), *Saccharomyces cerevisiae* (Sc) (SEQ ID NO: 45), *Candida albicans* (Ca) (SEQ ID NO: 46), *Hansenula polymorpha* (Hp) (SEQ ID NO: 47), *S. pombe* (Sp) (SEQ ID NO: 48), and using Clustal W and BOXSHADE 3.1 (www.ch.embnet.org), wherein exact identities between the three residues are shaded in gray, and numbering of the residues for each protein is indicated to the left of the protein sequences.--

Column 96, line 60, delete the words "or SEQ. ID No:13"

Column 97, lines 7-21 should read--An isolated nucleic acid molecule for detection of H. Capsulatum selected from the group consisting of:
    (a) a nucleic acid molecule comprising the sequence of SEQ ID NO: 7 or the complement thereof;
    (b) a nucleic acid molecule comprising the sequence of SEQ ID NO: 8 or the complement thereof;
    (c) a fragment of SEQ ID NO: 7 consisting of 20 or more consecutive nucleotides of SEQ ID NO: 7 or the complement thereof;
    (d) a fragment of SEQ ID NO: 8 consisting of 20 or more consecutive nucleotides of SEQ ID NO: 8 or the complement thereof;
    (e) an oligonucleotide selected from the group consisting of SEQ ID NO:12, SEQ ID NO: 13, and SEQ ID NO: 15.--

UNITED STATES PATENT AND TRADEMARK OFFICE
CERTIFICATE OF CORRECTION

PATENT NO. : 7,052,837 B2
APPLICATION NO. : 10/099352
DATED : May 30, 2006
INVENTOR(S) : Clayton H. Johnson, Joan E. McEwen and J. Lyndal York It is certified that error appears in the above-identified patent and that said Letters Patent is hereby corrected as shown below:

Column 97, line 30 should read--(b) determining whether there is hybridization of the isolated nucleic acid molecule to the sample, wherein a sample comprising H. capsulatum exhibits detectable hybridization and a sample lacking H. capsulatum does not exhibit hybridization, and wherein the isolated nucleic acid molecule is selected from the group consisting of:
    (i) a nucleic acid molecule comprising the sequence of SEQ ID NO: 7 or the complement thereof;
    (ii) a nucleic acid molecule comprising the sequence of SEQ ID NO: 8 or the complement thereof;
    (iii) a fragment of SEQ ID NO: 7 consisting of 20 or more consecutive nucleotides of SEQ ID NO: 7 or the complement thereof;
    (iv) a fragment of SEQ ID NO: 8 consisting of 20 or more consecutive nucleotides of SEQ ID NO: 8 or the complement thereof;
    (v) a nucleic acid molecule of up to 25 nucleotides in length that comprises 20 or more consecutive nucleotides of SEQ ID NO: 7 or the complement thereof;
    (vi) a nucleic acid molecule of up to 25 nucleotides in length that comprises 20 or more consecutive nucleotides of SEQ ID NO: 8 or the complement thereof;
    (vii) an oligonucleotide selected from the group consisting of SEQ ID NO: 12, SEQ ID NO: 13, or SEQ ID NO: 15.--

Column 97, line 55 should read--(a) conducting a polymerase chain reaction (PCR) amplification using the nucleic acid molecule that hybridizes to intron 1 or intron 2 of the H. capsulatum catalase A gene (CATA) as an amplification primer; and--

Column 97, line 62 should read--The method of claim 8, wherein the primers comprise at least one oligonucleotide molecule selected from the group consisting of SEQ ID NO: 12, SEQ ID NO: 13, and SEQ ID NO: 15.--

Column 99, line 9 should read--(b) determining whether there is hybridization of the isolated nucleic acid molecule to the sample, wherein a sample comprising H. capsulatum exhibits detectable hybridization, and wherein the isolated nucleic acid molecule is selected from the group consisting of:
    (i) a nucleic acid molecule comprising the sequence of SEQ ID NO: 9, SEQ ID NO: 10, or SEQ ID NO:11, or the complements of SEQ ID NO: 9, SEQ ID NO: 10, or SEQ ID NO:11.
    (ii) a fragment of SEQ ID NO:9 consisting of 19 or more consecutive nucleotides of SEQ ID NO:9 or the complement thereof;
    (iii) a fragment of SEQ ID NO: 10 consisting of 20 or more consecutive nucleotides of SEQ ID NO: 10 or the complement thereof;

UNITED STATES PATENT AND TRADEMARK OFFICE
CERTIFICATE OF CORRECTION

PATENT NO. : 7,052,837 B2
APPLICATION NO. : 10/099352
DATED : May 30, 2006
INVENTOR(S) : Clayton H. Johnson, Joan E. McEwen and J. Lyndal York It is certified that error appears in the above-identified patent and that said Letters Patent is hereby corrected as shown below:

Column 99, line 9 (cont'd)
    (iv) a fragment of SEQ ID NO: 11 consisting of 19 or more consecutive nucleotides of SEQ ID NO: 11 or the complement thereof;
    (v) a nucleic acid molecule of up to 25 nucleotides in length that comprises 19 or more consecutive nucleotides of SEQ ID NO: 9 or the complement thereof;
    (vi) a nucleic acid molecule of up to 25 nucleotides in length that comprises 20 or more consecutive nucleotides of SEQ ID NO: 10 or the complement thereof;
    (vii) a nucleic acid molecule of up to 25 nucleotides in length that comprises 19 or more consecutive nucleotides of SEQ ID NO: 11 or the complement thereof; and
    (viii) an oligonucleotide selected from the group consisting of SEQ ID NO: 18, SEQ ID NO: 19, SEQ ID NO: 20, SEQ ID NO: 21, SEQ ID NO: 22, and SEQ ID NO: 23.--

Column 99, line 39 should read--The method of claim 18, further comprising the steps of:
    (a) conducting polymerase chain reaction (PRC) amplification using the nucleic acid molecule that hybridizes to intron 1, intron 2, or intron 3 of the H. capsulatum catalase P gene (CATP) as an amplification primer; and
    (b) determining the presence or absence of the PCR product resulting from said amplification.--

Signed and Sealed this

Sixteenth Day of October, 2007

JON W. DUDAS
*Director of the United States Patent and Trademark Office*